(12) United States Patent
Couto

(10) Patent No.: US 8,846,632 B2
(45) Date of Patent: Sep. 30, 2014

(54) NUCLEIC ACIDS FOR TARGETING MULTIPLE REGIONS OF THE HCV GENOME

(75) Inventor: Linda B. Couto, Pleasonton, CA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 13/602,886

(22) Filed: Sep. 4, 2012

(65) Prior Publication Data

US 2013/0030042 A1    Jan. 31, 2013

Related U.S. Application Data

(63) Continuation-in-part of application No. PCT/US2011/026666, filed on Mar. 1, 2011.

(60) Provisional application No. 61/309,157, filed on Mar. 1, 2010, provisional application No. 61/408,047, filed on Oct. 29, 2010.

(51) Int. Cl.
  *C12N 15/11* (2006.01)
  *C07H 21/04* (2006.01)

(52) U.S. Cl.
  USPC ........................................ 514/44 A; 536/24.5

(58) Field of Classification Search
  USPC ........................................ 536/24.5; 514/44 A
  See application file for complete search history.

(56) References Cited

U.S. PATENT DOCUMENTS

| 2005/0043266 | A1* | 2/2005 | Jayasena et al. ................ 514/44 |
| 2005/0276787 | A1 | 12/2005 | Couto et al. |
| 2006/0104954 | A1* | 5/2006 | Podsakoff et al. ............ 424/93.2 |
| 2006/0188482 | A1* | 8/2006 | Kay et al. .................... 424/93.2 |
| 2006/0211642 | A1* | 9/2006 | McSwiggen et al. .......... 514/44 |
| 2007/0025969 | A1 | 2/2007 | Roelvink et al. |
| 2008/0070854 | A1 | 3/2008 | Pachuk et al. |
| 2009/0099124 | A1 | 4/2009 | Jayasena et al. |
| 2009/0306184 | A1 | 12/2009 | McSwiggen et al. |

OTHER PUBLICATIONS

Hu, T., et al. "Construction of an artificial MicroRNA expression vector for simultaneous inhibition of multiple genes in mammalian cells." Int J Mol Sci. May 14, 2009;10(5):2158-68.
Yang, X., et al. "Inhibition of hepatitis C virus replication using adeno-associated virus vector delivery of an exogenous anti-hepatitis C virus microRNA cluster." Hepatology. Dec. 2010;52(6):1877-87. Epub Oct. 7, 2010.

\* cited by examiner

*Primary Examiner* — Jon E Angell
(74) *Attorney, Agent, or Firm* — Dann, Dorfman, Herrell & Skillman; Kathleen D. Rigaut; Robert C. Netter, Jr.

(57) ABSTRACT

Compositions and methods effective for modulating Hepatitis C viral infection are provided.

20 Claims, 22 Drawing Sheets

Figure 5
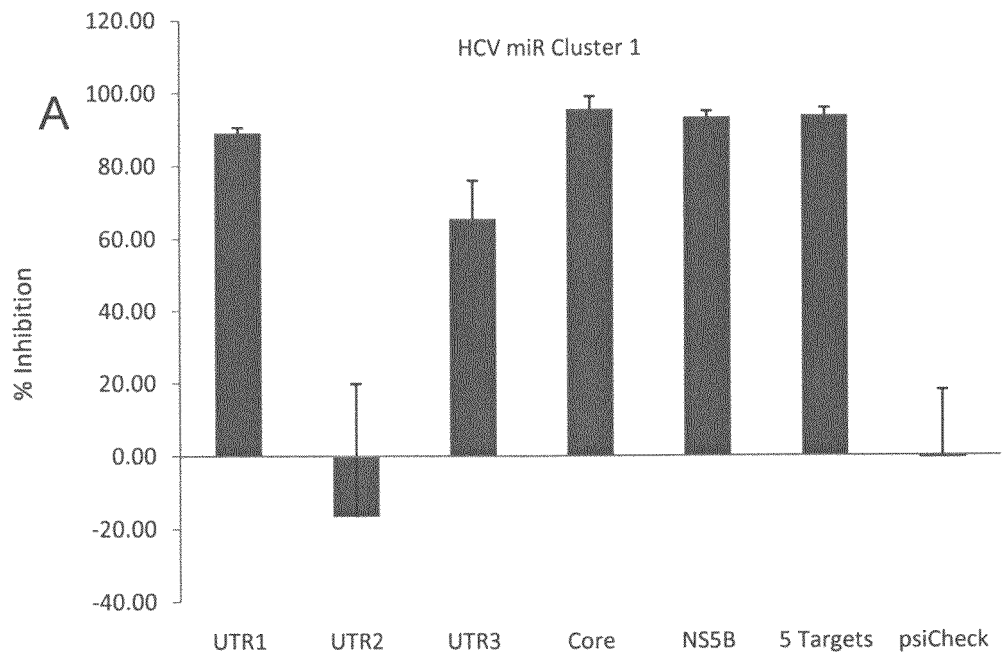
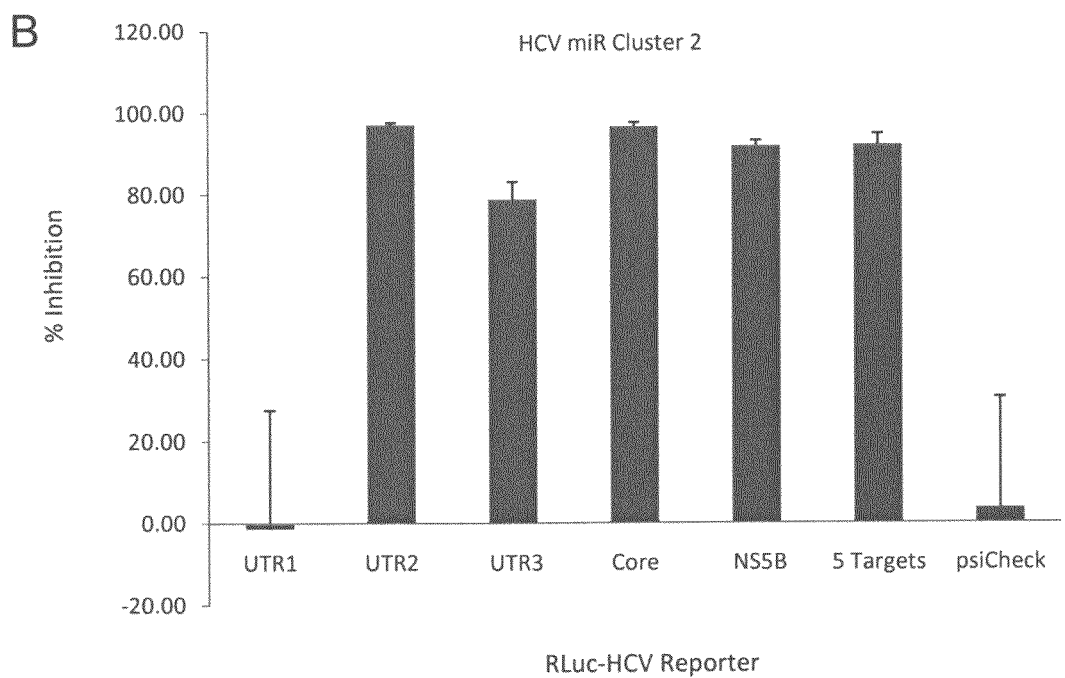

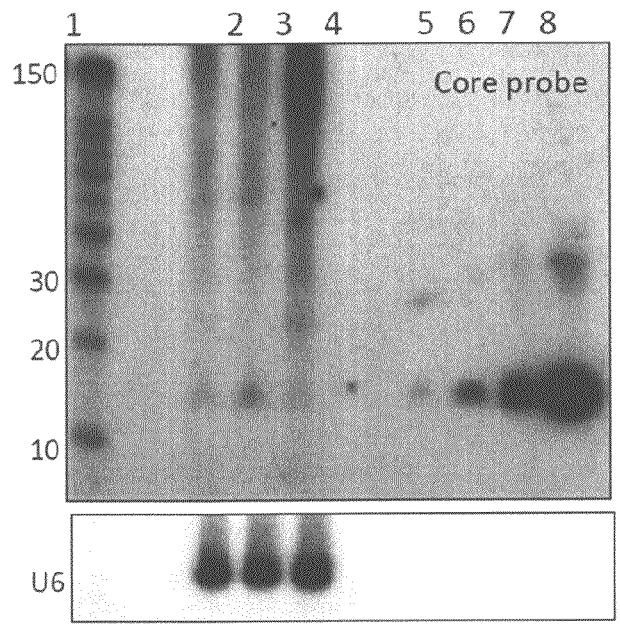
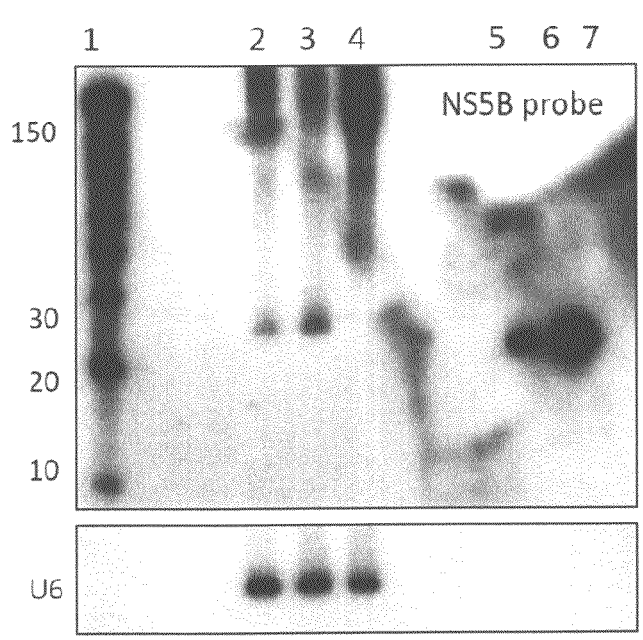
Figure 6

ApoE/hAAT-HCV miRNA Cluster 1

GCTGTTTGTGTGCTGCCTCTGAAGTCCACACTGAACAAACTTCAGCCTACTCATGTCCCTAAAATGGGCAAACATTG
CAAGCAGCAAACAGCAAACACACAGCCCTCCCTGCCTGCTGACCTTGGAGCTGGGGCAGAGGTCAGAGACCTCTC
TGGGCCCATGCCACCTCCAACATCCACTCGACCCCTTGGAATTTCGGTGGAGAGGAGCAGAGGTTGTCCTGGCGT
GGTTTAGGTAGTGTGAGAGGGGTACCCGGGGATCTTGCTACCAGTGGAACAGCCACTAAGGATTCTGCAGTGAG
AGCAGAGGGCCAGCTAAGTGGTACTCTCCCAGAGACTGTCTGACTCACGCCACCCCCTCCACCTTGGACACAGGA
CGCTGTGGTTTCTGAGCCAGGTACAATGACTCCTTTCGGTAAGTGCAGTGGAAGCTGTACACTGCCCAGGCAAAG
CGTCCGGGCAGCGTAGGCGGGCGACTCAGATCCCAGCCAGTGGACTTAGCCCCTGTTTGCTCCTCCGATAACTGG
GGTGACCTTGGTTAATATTCACCAGCAGCCTCCCCCGTTGCCCCTCTGGATCCACTGCTTAAATACGGACGAGGAC
AGGGCCCTGTCTCCTCAGCTTCAGGCACCACCACTGACCTGGGACAGTGCATGCGTTAGAGTTTGAGGTGTTAATT
CTAATTATCTATTTCAAATTTAGCAGGAAAAAAGAGAACATCACCGGTTAAAACTGAAGATTGTGACCAGTCAGAA
TAATGTGTTCCGCAGACCACTATGGGTAGTGATATGTGCATCTACCATACTGCTTTGCGGATTGGCATTATGGTGA
CAGCTGCCTCGGGAAGCCAAGTTGGATCCTAAAGTGCAGGGCCTGCTGATGTTGAGTGCTTTTTGTTCAGGCAGT
ACCACAAGGCCTTTAGTGAAGTAGATTAGCATCTAAGGCGTTGCAGTAGTGTCCTGGCATAAGAAGTTATGTATTC
ATCCAATAATCGATGCCAAGCAAGTATATAGGTGTTTTAATAGTTTTTGTTTGCAGTCCTCTGTTAGAGGTCTCGTA
CCGTGTTACAAGAAGAATGTAGTTGCACGGTCTACGAGACCTCTGATGGTGGCCTGCTATTTCCTTCAAATGAATG
ATTTTTACTAATTTTGTGTACTTTTATTGATCAGATGTAGAATCTGCCTGGTCTATCTGATGTGACAGCTTCTGTAGC
ACGTTTGGTTTTTCTTTGAGGTTAGTGTTTAGTTATCTACCTCAGAGAGAAACTAATTCGTACTGCTAGCTGTAGAA
CTCCAGCTTCGGCCGGTCGCCCAATCAAACTGTCCTGTTACTGAACACTGTTCTATGGTTGACACTGAGCACAATTG
TCATGCTGTGTGATATTCTGCGTCAATGGTGTCTCAGTGTCGACTGTGGTAGTGAAAAGTCTGTAGAAAAGTGTT
TAAACTGTGCCTTCTAGTTGCCAGCCATCTGTTGTTTGCCCCTCCCCCGTGCCTTCCTTGACCCTGGAAGGTGCCACT
CCCACTGTCCTTTCCTAATAAAATGAGGAAATTGCATCGCATTGTCTGAGTAGGTGTCATTCTATTCTGGGGGGTG
GGGTGGGGCAGGACAGCAAGGGGGAGGATTGGGAAGACAATAGCAGGCATGCTGGGGATGCGGTGGGCTCTA
T

FIGURE 8A

ApoE/hAAT-HCV miRNA Cluster 2

```
GCTGTTTGTGTGCTGCCTCTGAAGTCCACACTGAACAAACTTCAGCCTACTCATGTCCCTAAAATGGGCAAACATTG
CAAGCAGCAAACAGCAAACACACAGCCCTCCCTGCCTGCTGACCTTGGAGCTGGGGCAGAGGTCAGAGACCTCTC
TGGGCCCATGCCACCTCCAACATCCACTCGACCCCTTGGAATTTCGGTGGAGAGGAGCAGAGGTTGTCCTGGCGT
GGTTTAGGTAGTGTGAGAGGGGTACCCGGGGATCTTGCTACCAGTGGAACAGCCACTAAGGATTCTGCAGTGAG
AGCAGAGGGCCAGCTAAGTGGTACTCTCCCAGAGACTGTCTGACTCACGCCACCCCCTCCACCTTGGACACAGGA
CGCTGTGGTTTCTGAGCCAGGTACAATGACTCCTTTCGGTAAGTGCAGTGGAAGCTGTACACTGCCCAGGCAAAG
CGTCCGGGCAGCGTAGGCGGGCGACTCAGATCCCAGCCAGTGGACTTAGCCCCTGTTTGCTCCTCCGATAACTGG
GGTGACCTTGGTTAATATTCACCAGCAGCCTCCCCCGTTGCCCCTCTGGATCCACTGCTTAAATACGGACGAGGAC
AGGGCCCTGTCTCCTCAGCTTCAGGCACCACCACTGACCTGGGACAGTGCATGCGTTAGAGTTTGAGGTGTTAATT
CTAATTATCTATTTCAAATTTAGCAGGAAAAAAGAGAACATCACCGGTTAAAACTGAAGATTGTGACCAGTCAGAA
TAATGTAGGCAGTACCACAAGGCCTTTAGTGATATGTGCATCTAAGGCCATGAGATACTGCGAAGCATTATGGTG
ACAGCTGCCTCGGGAAGCCAAGTTGGATCCTAAAGTGCAGGGCCTGCTGATGTTGAGTGCTTTTTGTTCGTTCCGC
AGACCACTATGGATAGTGAAGTAGATTAGCATCTACCATCGTGAGCTGGGGAAGTGGCATAAGAAGTTATGTATT
CATCCAATAATCGATGCCAAGCAAGTATATAGGTGTTTTAATAGTTTTTGTTTGCAGTCCTCTGTTAGAGGTCTCGT
ACCGTGTTACAAGAAGAATGTAGTTGCACGGTCTACGAGACCTCTGATGGTGGCCTGCTATTTCCTTCAAATGAAT
GATTTTTACTAATTTTGTGTACTTTTATTGATCAGATGTAGAATCTGCCTGGTCTATCTGATGTGACAGCTTCTGTAG
CACGTTTGGTTTTTCTTTGAGGTTAGTGTTTAGTTATCTACCTCAGAGAGAAACTAATTCGTACTGCTAGCTGTAGA
ACTCCAGCTTCGGCCGGTCGCCCAATCAAACTGTCCTGTTACTGAACACTGTTCTATGGTTGACACTGAGCACAATT
GTCATGCTGTGTGATATTCTGCGTCAATTGGTGTCTCAGTGTCGACTGTGGTAGTGAAAAGTCTGTAGAAAAGTGT
TTAAACCTGTGCCTTCTAGTTGCCAGCCATCTGTTGTTTGCCCCTCCCCCGTGCCTTCCTTGACCCTGGAAGGTGCCA
CTCCCACTGTCCTTTCCTAATAAAATGAGGAAATTGCATCGCATTGTCTGAGTAGGTGTCATTCTATTCTGGGGGGT
GGGGTGGGGCAGGACAGCAAGGGGGAGGATTGGGAAGACAATAGCAGGCATGCTGGGGATGCGGTGGGCTCT
AT
```

FIGURE 8B

```
                            Fig. 13A
              psCAAV-APOEhAAT-HCVmiRNAS-Cluster_5

LOCUS       pscAAV-ApoE/hAAT      9024 bp    DNA     circular    14-MAY-2010
SOURCE
  ORGANISM
COMMENT     http://www.informaxinc.com/
COMMENT     This file is created by Vector NTI
            http://www.invitrogen.com/
COMMENT     ORIGDB|GenBank
COMMENT     VNTDATE|554206959|
COMMENT     VNTDBDATE|554206959|
COMMENT     LSOWNER|
COMMENT     VNTNAME|pscAAV-ApoE/hAAT-HCVmiRNAs-Cluster 5|
COMMENT     VNTAUTHORNAME|Demo User|
FEATURES             Location/Qualifiers
     CDS             7336..8193
                     /vntifkey="4"
                     /label=Ampicillin\Resistance\\(9589-10446)
     misc_structure  complement(6502..6817)
                     /vntifkey="88"
                     /label=f1\origin\of\replication\(8755-9070)
     misc_feature    complement(8344..9011)
                     /vntifkey="21"
                     /label=pUC\origin\(10597-11264)
     misc_marker     2062..6422
                     /vntifkey="22"
                     /label=Lambda\DNA\HindIII\Stuffer\(4314-8675)
     misc_feature    166..815
                     /vntifkey="21"
                     /label=APOE-hAAT\promoter
     misc_feature    1927..2043
                     /vntifkey="21"
                     /label=Deleted\AAV4\ITR
     misc_feature    1695..1918
                     /vntifkey="21"
                     /label=bGH\pA
     misc_feature    16..157
                     /vntifkey="21"
                     /label=WT\AAV2\ITR
     misc_feature    892..1686
                     /vntifkey="21"
                     /label=miRNA-HCV
BASE COUNT     2283 a      2083 c      2237 g      2421 t
ORIGIN
        1 cctgcaggga gatctgccac tccctctctg cgcgctcgct cgctcactga ggccgggcga
       61 ccaaaggtcg cccgacgccc gggctttgcc cgggcggcct cagtgagcga gcgagcgcgc
      121 agagagggag tggccaactc catcactagg ggttcctgcg atcgcgctgt ttgtgtgctg
      181 cctctgaagt ccacactgaa caaacttcag cctactcatg tccctaaaat gggcaaacat
      241 tgcaagcagc aaacagcaaa cacacagccc tccctgcctg ctgaccttgg agctgggggca
      301 gaggtcagag acctctctgg gccatgccca ctccaacat ccactcgacc ccttggaatt
      361 tcggtggaga ggagcagagg ttgtcctggc gtggtttagg tagtgtgaga ggggtacccg
      421 gggatcttgc taccagtgga acagccacta aggattctgc agtgagagca gagggccagc
      481 taagtggtac tctcccagag actgtctgac tcacgccacc cctccacct tggacacagg
      541 acgctgtggt ttctgagcca ggtacaatga ctcctttcgg taagtgcagt ggaagctgta
      601 cactgcccag gcaaagcgtc cggcagcgt aggcgggcga ctcagatccc agccagtgga
      661 cttagcccct gtttgctcct ccgataactg gggtgacctt ggttaatatt caccagcagc
```

Fig. 13B

```
 721 ctcccccgtt gccctctgg atccactgct taaatacgga cgaggacagg gccctgtctc
 781 ctcagcttca ggcaccacca ctgacctggg acagtgcatg cgttagagtt tgaggtgtta
 841 attctaatta tctatttcaa atttagcagg aaaaaagaga acatcaccgg ttaaaactga
 901 agattgtgac cagtcagaat aatgtaggca gtaccacaag gcctttagtg atatgtgcat
 961 ctaaggccat gagatactgc gaagcattat ggtgacagct gcctcgggaa gccaagttgg
1021 atcctaaagt gcagggcctg ctgatgttga gtgctttta agaagttatg tattcatcca
1081 ataatcgatg ccaagcaagt ataggtgt tttaatagtt tttgtttgca gtcctctgtt
1141 agaggtctcg taccgtgtta caagaagaat gtagttgcac ggtctacgag acctctgatg
1201 gtggcctgct atttccttca aatgaatgat ttttactaat tttgtgtact tttattgatc
1261 agatgtagaa tctgcctggt ctatctgatg tgacagcttc tgtagcacgt ttggttttc
1321 tttgaggtta gtgtttagtt atctacctca gagagaaact aattcgtact gctagctgta
1381 gaactccagc ttcggccggt cgcccaatca aactgtcctg ttactgaaca ctgttctatg
1441 gttgacactg agcacaattg tcatgctgtg tgatattctg cgtcaattgg tgtctcagtg
1501 tcgactgtgg tagtgaaaag tctgtagaaa agtgtttaaa caagggaaac tcaaacccct
1561 ttctacacac catagtgact tgtcggaatc tgtgtttctg tatgggttcc gcagaccact
1621 atggtgttga gtttggtggg gattgtgacc agaagatttt gaaaattaaa tattactgaa
1681 gatttcgttt aaactgtgcc ttctagttgc cagccatctg ttgtttgccc ctcccccgtg
1741 ccttccttga ccctggaagg tgccactccc actgtccttt cctaataaaa tgaggaaatt
1801 gcatcgcatt gtctgagtag gtgtcattct attctggggg gtggggtggg gcaggacagc
1861 aaggggagg attgggaaga caatagcagg catgctgggg atgcggtggg ctctatgggg
1921 ccggccccac tccctctatg cgcgctcgct cactcactcg gccctgccgg ccagaggccg
1981 gcagtctgga gacctttggt ctccagggcc gagtgagtga gcgagcgcgc atagagggag
2041 tggcatatgt cctgcagggg cagcttgaag gaaatactaa ggcaaaggta ctgcaagtgc
2101 tcgcaacatt cgcttatgcg gattattgcc gtagtgccgc gacgccgggg gcaagatgca
2161 gagattgcca tggtacaggc cgtgcggttg atattgccaa aacagagctg tggggagag
2221 ttgtcgagaa agagtgcgga agatgcaaag gcgtcggcta ttcaaggatg ccagcaagcg
2281 cagcatatcg cgctgtgacg atgctaatcc caaaccttac ccaacccacc tggtcacgca
2341 ctgttaagcc gctgtatgac gctctggtgg tgcaatgcca caaagaagag tcaatcgcag
2401 acaacatttt gaatgcggtc acacgttagc agcatgattg ccacggatgg caacatatta
2461 acggcatgat attgacttat tgaataaaat tgggtaaatt tgactcaacg atgggttaat
2521 tcgctcgttg tggtagtgag atgaaaagag gcggcgctta ctaccgattc cgcctagttg
2581 gtcacttcga cgtatcgtct ggaactccaa ccatcgcagg cagagaggtc tgcaaaatgc
2641 aatcccgaaa cagttcgcag gtaatagtta gagcctgcat aacggtttcg ggattttta
2701 tatctgcaca acaggtaaga gcattgagtc gataatcgtg aagagtcggc gagcctggtt
2761 agccagtgct cttttccgttg tgctgaatta agcgaatacc ggaagcagaa ccggatcacc
2821 aaatgcgtac aggcgtcatc gccgcccagc aacagcacaa cccaaactga gccgtagcca
2881 ctgtctgtcc tgaattcatt agtaatagtt acgctgcggc cttttacaca tgaccttcgt
2941 gaaagcgggt ggcaggaggt cgcgctaaca acctcctgcc gttttgcccg tgcatatcgg
3001 tcacgaacaa atctgattac taaacacagt agcctggatt tgttctatca gtaatcgacc
3061 ttattcctaa ttaaatagag caaatcccct tatgggggt aagacatgaa gatgccagaa
3121 aaacatgacc tgttggccgc cattctcgcg gcaaaggaac aaggcatcgg ggcaatcctt
3181 gcgtttgcaa tggcgtacct tcgcggcaga tataatggcg gtgcgtttac aaaaacagta
3241 atcgacgcaa cgatgtgcgc cattatcgcc tggttcattc gtgaccttct cgacttcgcc
3301 ggactaagta gcaatctcgc ttatataacg agcgtgttta tcggctacat cggtactgac
3361 tcgattggtt cgcttatcaa acgcttcgct gctaaaaaag ccggagtaga agatggtaga
3421 aatcaataat caacgtaagg cgttcctcga tatgctggcg tggtcggagg gaactgataa
3481 cggacgtcag aaaaccagaa atcatggtta tgacgtcatt gtaggcggag agctatttac
3541 tgattactcc gatcaccctc gcaaacttgt cacgctaaac ccaaaactca atcaacagg
3601 cgccggacgc taccagcttc tttcccgttg gtgggatgcc taccgcaagc agcttggcct
3661 gaaagacttc tctccgaaaa gtcaggacgc tgtggcattg cagcagatta aggagcgtgg
3721 cgctttacct atgattgatc gtggtgatat ccgtcaggca atcgaccgtt gcagcaatat
3781 ctgggcttca ctgccgggcg ctggttatgg tcagttcgag cataaggctg acagcctgat
3841 tgcaaaattc aaagaagcgg cggaacggt cagagagatt gatgtatgag cagagtcacc
3901 gcgattatct ccgctctggt tatctgcatc atcgtctgcc tgtcatgggc tgttaatcat
3961 taccgtgata acgccattac ctacaaagcc cagcgcgaca aaaatgccag agaactgaag
4021 ctggcgaacg cggcaattac tgacatgcag atgcgtcagc gtgatgttgc tgcgctcgat
```

Fig. 13C

```
4081 gcaaaataca cgaaggagtt agctgatgct aaagctgaaa atgatgctct gcgtgatgat
4141 gttgccgctg gtcgtcgtcg gttgcacatc aaagcagtct gtcagtcagt gcgtgaagcc
4201 accaccgcct ccggcgtgga taatgcagcc tcccccgac tggcagacac cgctgaacgg
4261 gattatttca ccctcagaga gaggctgatc actatgcaaa acaactggaa aggaacccag
4321 aagtatatta atgagcagtg cagatagagt tgcccatatc gatgggcaac tcatgcaatt
4381 attgtgagca atacacacgc gcttccagcg gagtataaat gcctaaagta ataaaaccga
4441 gcaatccatt tacgaatgtt tgctgggttt ctgttttaac aacattttct gcgccgccac
4501 aaattttggc tgcatcgaca gttttcttct gcccaattcc agaaacgaag aaatgatggg
4561 tgatggtttc ctttggtgct actgctgccg gtttgttttg aacagtaaac gtctgttgag
4621 cacatcctgt aataagcagg gccagcgcag tagcgagtag cattttttc atggtgttat
4681 tcccgatgct ttttgaagtt cgcagaatcg tatgtgtaga aaattaaaca accctaaac
4741 aatgagttga aatttcatat tgttaatatt tattaatgta tgtcaggtgc gatgaatcgt
4801 cattgtattc ccggattaac tatgtccaca gccctgacgg ggaacttctc tgcgggagtg
4861 tccgggaata attaaaacga tgcacacagg gtttagcgcg tacacgtatt gcattatgcc
4921 aacgccccgg tgctgacacg gaagaaaccg gacgttatga tttagcgtgg aaagatttgt
4981 gtagtgttct gaatgctctc agtaaatagt aatgaattat caaaggtata gtaatatctt
5041 ttatgttcat ggatatttgt aacccatcgg aaaactcctg ctttagcaag attttccctg
5101 tattgctgaa atgtgatttc tcttgatttc aacctatcat aggacgtttc tataagatgc
5161 gtgtttcttg agaatttaac atttacaacc tttttaagtc cttttattaa cacggtgtta
5221 tcgttttcta acacgatgtg aatattatct gtggctagat agtaaatata atgtgagacg
5281 ttgtgacgtt ttagttcaga ataaacaat tcacagtcta aatcttttcg cacttgatcg
5341 aatatttctt taaaaatggc aacctgagcc attggtaaaa ccttccatgt gatacgaggg
5401 cgcgtagttt gcattatcgt ttttatcgtt tcaatctggt ctgacctcct tgtgttttgt
5461 tgatgattta tgtcaaatat taggaatgtt ttcacttaat agtattggtt gcgtaacaaa
5521 gtgcggtcct gctggcattc tggagggaaa tacaaccgac agatgtatgt aaggccaacg
5581 tgctcaaatc ttcatacaga aagatttgaa gtaatatttt aaccgctaga tgaagagcaa
5641 gcgcatggag cgacaaaatg aataaagaac aatctgctga tgatccctcc gtggatctga
5701 ttcgtgtaaa aaatatgctt aatagcacca tttctatgag ttaccctgat gttgtaattg
5761 catgtataga acataaggtg tctctggaag cattcagagc aattgaggca gcgttggtga
5821 agcacgataa taatatgaag gattattccc tggtggttga ctgatcacca taactgctaa
5881 tcattcaaac tatttagtct gtgacagagc caacacgcag tctgtcactg tcaggaaagt
5941 ggtaaaactg caactcaatt actgcaatgc cctcgtaatt aagtgaattt acaatatcgt
6001 cctgttcgga gggaagaacg cgggatgttc attcttcatc acttttaatt gatgtatatg
6061 ctctcttttc tgacgttagt ctccgacggc aggcttcaat gacccaggct gagaaattcc
6121 cggacccttt tgctcaaga gcgatgttaa tttgttcaat catttggtta ggaaagcgga
6181 tgttgcgggt tgttgttctg cgggttctgt tcttcgttga catgaggttg ccccgtattc
6241 agtgtcgctg atttgtattg tctgaagttg tttttacgtt aagttgatgc agatcaatta
6301 atacgatacc tgcgtcataa ttgattattt gacgtggttt gatggcctcc acgcacgttg
6361 tgatatgtag atgataatca ttatcacttt acgggtcctt tccggtgatc cgacaggtta
6421 cggcctgatg cggtattttc tccttacgca tctgtgcggt atttcacacc gcatacgtca
6481 aagcaaccat agtacgcgcc ctgtagcggc gcattaagcg cggcgggtgt ggtggttacg
6541 cgcagcgtga ccgctacact tgccagcgcc ctagcgcccg ctcctttcgc tttcttccct
6601 tcctttctcg ccacgttcgc cggctttccc cgtcaagctc taaatcgggg gctcccttta
6661 gggttccgat ttagtgcttt acggcacctc gaccccaaaa aacttgattt gggtgatggt
6721 tcacgtagtg ggccatcgcc ctgatagacg gttttcgcc ctttgacgtt ggagtccacg
6781 ttcttttaata gtggactctt gttccaaact ggaacaacac tcaaccctat ctcgggctat
6841 tcttttgatt tataagggat tttgccgatt tcggcctatt ggttaaaaaa tgagctgatt
6901 taacaaaaat taacgcgaa ttttaacaaa atattaacgt ttacaatttt atggtgcact
6961 ctcagtacaa tctgctctga tgccgcatag ttaagccagc cccgacaccc gccaacaccc
7021 gctgacgcgc cctgacgggc ttgtctgctc ccggcatccg cttacagaca agctgtgacc
7081 gtctccggga gctgcatgtg tcagaggttt tcaccgtcat caccgaaacg cgcgagacga
7141 aagggcctcg tgatacgcct atttttatag gttaatgtca tgataataat ggtttcttag
7201 acgtcaggtg gcacttttcg gggaaatgtg cgcggaaccc ctatttgttt attttctaa
7261 atacattcaa atatgtatcc gctcatgaga caataaccct gataaatgct tcaataatat
7321 tgaaaaagga agagtatgag tattcaacat ttccgtgtcg cccttattcc cttttttgcg
7381 gcattttgcc ttcctgtttt tgctcaccca gaaacgctgg tgaaagtaaa agatgctgaa
```

Fig. 13D

```
7441 gatcagttgg gtgcacgagt gggttacatc gaactggatc tcaacagcgg taagatcctt
7501 gagagttttc gccccgaaga acgttttcca atgatgagca cttttaaagt tctgctatgt
7561 ggcgcggtat tatcccgtat tgacgccggg caagagcaac tcggtcgccg catacactat
7621 tctcagaatg acttggttga gtactcacca gtcacagaaa agcatcttac ggatggcatg
7681 acagtaagag aattatgcag tgctgccata accatgagtg ataacactgc ggccaactta
7741 cttctgacaa cgatcggagg accgaaggag ctaaccgctt ttttgcacaa catgggggat
7801 catgtaactc gccttgatcg ttgggaaccg gagctgaatg aagccatacc aaacgacgag
7861 cgtgacacca cgatgcctgt agcaatggca acaacgttgc gcaaactatt aactggcgaa
7921 ctacttactc tagcttcccg gcaacaatta atagactgga tggaggcgga taaagttgca
7981 ggaccacttc tgcgctcggc ccttccggct ggctggttta ttgctgataa atctggagcc
8041 ggtgagcgtg ggtctcgcgg tatcattgca gcactggggc cagatggtaa gccctcccgt
8101 atcgtagtta tctacacgac ggggagtcag gcaactatgg atgaacgaaa tagacagatc
8161 gctgagatag gtgcctcact gattaagcat tggtaactgt cagaccaagt ttactcatat
8221 atactttaga ttgatttaaa acttcatttt taatttaaaa ggatctaggt gaagatcctt
8281 tttgataatc tcatgaccaa aatcccttaa cgtgagtttt cgttccactg agcgtcagac
8341 cccgtagaaa agatcaaagg atcttcttga gatccttttt ttctgcgcgt aatctgctgc
8401 ttgcaaacaa aaaaaccacc gctaccagcg gtggtttgtt tgccggatca agagctacca
8461 actcttttc cgaaggtaac tggcttcagc agagcgcaga taccaaatac tgtccttcta
8521 gtgtagccgt agttaggcca ccacttcaag aactctgtag caccgcctac atacctcgct
8581 ctgctaatcc tgttaccagt ggctgctgcc agtggcgata agtcgtgtct taccgggttg
8641 gactcaagac gatagttacc ggataaggcg cagcggtcgg gctgaacggg gggttcgtgc
8701 acacagccca gcttggagcg aacgacctac accgaactga gatacctaca gcgtgagcta
8761 tgagaaagcg ccacgcttcc cgaagggaga aaggcggaca ggtatccggt aagcggcagg
8821 gtcggaacag gagagcgcac gagggagctt ccaggggaa acgcctggta tctttatagt
8881 cctgtcgggt ttcgccacct ctgacttgag cgtcgatttt tgtgatgctc gtcaggggg
8941 cggagcctat ggaaaaacgc cagcaacgcg gcctttttac ggttcctggc cttttgctgg
9001 cctttttgctc acatgtcctg cagg
//
```

Fig. 13E

```
taaaactgaagattgtgaccagtcagaataatgtaggcagtaccacaaggcctttagtgatatgtgcatctaaggc
catgagatactgcgaagcattatggtgacagctgcctcgggaagccaagttggatcctaaagtgcagggcctgctg
atgttgagtgcttttttaagaagttatgtattcatccaataatcgatgccaagcaagtatataggtgttttaatagt
ttttgtttgcagtcctctgttagaggtctcgtaccgtgttacaagaagaatgtagttgcacggtctacgagacctc
tgatggtggcctgctatttccttcaaatgaatgattttactaattttgtgtacttttattgatcagatgtagaat
ctgcctggtctatctgatgtgacagcttctgtagcacgtttggtttttctttgaggttagtgtttagttatctacc
tcagagagaaactaattcgtactgctagctgtagaactccagcttcggccggtcgcccaatcaaactgtcctgtta
ctgaacactgttctatggttgacactgagcacaattgtcatgctgtgtgatattctgcgtcaattggtgtctcagt
gtcgactgtggtagtgaaaagtctgtagaaagtgtttaaacaagggaaactcaaaccccttctacacaccatag
tgacttgtcggaatctgtgtttctgtatgggttccgcagaccactatggtgttgagtttggtggggattgtgacca
gaagattttgaaaattaaatattactgaagatttc
```

NUCLEIC ACIDS FOR TARGETING MULTIPLE REGIONS OF THE HCV GENOME

This application is a continuation in part application of PCT/US2011/026666 filed Mar. 1, 2011 which in turn claims priority to U.S. Provisional Applications 61/309,157 and 61/408,047 filed Mar. 3, 2010 and Oct. 29, 2010 respectively, the entire contents of each being incorporated herein by reference.

FIELD OF THE INVENTION

This invention relates to the fields of medicine, molecular biology and treatment of disease. More specifically, the present invention features compositions and methods useful for the treatment of Hepatitis C infection.

BACKGROUND OF THE INVENTION

Several publications and patent documents are cited throughout this application in order to more fully describe the state of the art to which this invention pertains. The disclosure of each of these citations is incorporated by reference herein. It is estimated that approximately 3% of the world population, or 170 million people, are chronically infected with the hepatitis C virus (HCV); with 3.2 million affected individuals in the United States alone. Most acute HCV infections are asymptomatic, but the infection resolves spontaneously in only about 15-30% of subjects. For the remaining 70-85% of individuals, a chronic infection persists, and decades can elapse before symptoms appear. Chronic HCV infection can lead to serious liver disease, including steatosis, fibrosis, cirrhosis and hepatocellular carcinoma (HCC). Approximately 20% of chronically infected individuals will develop cirrhosis, and 1.2-4% of all those chronically infected will develop HCC.

The current therapy for HCV infection is a year long treatment with a combination of pegylated interferon-α (INF-α) and ribavirin. This treatment is approximately 80% effective against HCV genotypes 2 and 3, but against the major genotype found in the United States and the world (genotype 1), it is less than 50% effective. In addition, there are numerous serious side effects from these drugs including neutropenia, anemia, nausea, and depression. A number of specific small molecule antiviral therapies are currently under development, and although some have shown good antiviral properties, they are not broadly applicable to all HCV genotypes and drug resistance develops quickly.

RNA interference (RNAi) based-technology is being developed to treat a wide range of diseases (1), and is a particularly good strategy for treating RNA virus-mediated diseases, such as HIV, HCV, and polio virus infections. RNAi is mediated by a variety of small regulatory RNAs, which differ in their biogenesis (2). Short interfering RNAs (siRNAs) are small double-stranded RNAs of 21-23 nt that are generated in the cytoplasm from longer RNAs (e.g., viral) following enzymatic cleavage by the RNase III enzyme Dicer. In contrast, microRNAs (miRNAs) are derived from long primary RNAs (pri-miRNA) that are transcribed in the nucleus and cleaved by the microprocessor complex, composed of the nuclear enzyme Drosha and its cofactor DGCR8, into ~70 nt precursor stem-loop RNAs (pre-miRNAs). Pre-miRNAs are exported to the cytoplasm by Exportin 5, where they are further processed by Dicer into mature miRNAs. Short hairpin RNAs (shRNAs) (3) are not naturally found in cells, but they are designed to be expressed from plasmids or viral vectors in the nucleus and have a stem-loop structure similar to pre-miRNAs. The shRNAs are also cleaved by Drosha/DGCR8 in the nucleus and are transported to the cytoplasm where they are cleaved into siRNAs by Dicer. The products of these pathways (siRNAs and miRNAs) induce gene silencing after the antisense (AS) or guide strand of the RNA duplex is loaded into the RNA induced silencing complex (RISC), and guides the endonucleolytic cleavage or translational repression of a cognate mRNA. The RNA strand of the siRNA duplex that has the lowest free energy at the 5' end will be loaded into the RISC and will mediate post-transcriptional silencing (4;5) Using this feature, as well as other characteristics that have been identified empirically (6), it is possible to design synthetic siRNAs that are highly effective in silencing cellular and viral genes.

As such, RNAi has become a standard tool to inhibit gene expression, and a variety of nucleic acid species are capable of modifying gene expression. These include antisense RNA, siRNA, shRNA, microRNA (miRNAs). Other approaches to down modulate target gene expression include use of RNA and DNA aptamers. Each of these nucleic acid species have been shown to inhibit target nucleic acid activity, including gene expression, but a need exists to selectively down-regulate the expression of viral genes.

In the case of Hepatitis C virus (HCV), siRNAs targeting the 5' untranslated region (UTR), core, and several non-structural proteins (NS3, NS4B, NS5A, and NS5B) have all been shown to inhibit HCV RNA and protein levels by up to 95% when tested in cells containing autonomously replicating full genomic or subgenomic HCV replicons (7;8). Likewise, shRNAs targeting the 5' UTR, E2, NS3, and NS5B were also capable of inhibiting virus replication in replicon-containing cells (7;8). However, RNAi-based technologies suffer from the same problems that plague traditional anti-viral drugs; that is, sustained use of single RNAi effectors results in the emergence of RNAi-resistant viral variants, which contain nucleotide substitutions or deletions in the areas targeted by the RNAi effectors. It is now generally agreed that for viruses that are replicated by low fidelity RNA polymerases, such as HCV, antiviral drug therapy involving RNAi should be used in a combined fashion to prevent the emergence of resistant viruses (7;10;11).

Many groups are now developing new approaches to simultaneously deliver multiple RNAi effectors to target HCV and HIV, including the use of pools of siRNAs (12) and the expression of multiple shRNAs (13;14). For example, expression cassettes with four shRNAs have been shown to prevent the emergence of HIV viral escape mutants (14). One important finding from these studies is the importance of avoiding the use of repetitive elements in the expression constructs (e.g., identical promoters) when using lentiviral vectors for delivery, in order to prevent the deletion of one or multiple shRNA cassettes by recombination.

The first group to show that a human microRNA stem-loop RNA precursor (miR-30) could be used as a scaffold to shuttle siRNA sequences also developed design rules for the construction of these so-called artificial miRNAs (15). In addition to a large terminal loop, efficient Drosha processing of a pri-miRNA transcript requires single stranded RNA sequences flanking the 70-80 nt stem-loop structure. Since then many other investigators have utilized artificial miRNAs based on miR-30 and other endogenous miRNAs to express individual RNAi effectors from either Pol II (16-18)or Pol III (19-21) promoters. Artificial miRNA hairpins have also been multimerized in order to express a combination of miRNAs in a single vector (22-27). However, like some of the multiple shRNA constructs, most of these miRNA complexes use repetitive elements, and thus may be genetically unstable in vectors employed for therapeutic use.

Over the past several years, distinct differences have been observed between the use of shRNAs and miRNAs. Recent studies using Pol III-driven shRNAs and miRNAs, that have been carefully designed such that they each generate similar processed siRNAs with the equivalent strand biasing, indicate that shRNAs are more potent than miRNAs (28). This is likely due to the higher levels of siRNAs that are generated from equivalent amounts of expression plasmids. However, there is also a high level of precursor RNA produced using shRNAs, while there is minimal build-up of pre-miRNAs when using artificial miRNAs (28;29). Furthermore, using a CMV promoter to express miRNAs, no precursors were observed, suggesting that complete processing of Pol II transcripts occurs more efficiently than that of Pol III-expressed miRNAs (17). High levels of precursor RNAs are an indication that the endogenous RNAi machinery is being saturated. Interfering with miRNA biogenesis can have serious consequences since this pathway is involved in critical cellular processes. There is now general agreement from in vitro studies that artificial miRNAs are less likely to lead to this problem, as non-related shRNAs compete with each other and with exogenous and endogenous miRNAs, whereas miRNAs expressed from pol II promoters do not (20;30).

Several in vivo studies have highlighted the problems encountered with the use of shRNAs, and have confirmed that interfering with the miRNA pathway leads to toxicity. Expression of several individual shRNAs from an AAV vector caused severe liver damage and fatality at high doses of vector (31). Toxicity was also observed in mouse brain using an AAV vector expressing shRNAs targeting the Huntington or spinocerebellar ataxia type 1 genes (29;32).

It is clear that a need exists for other safe and effective compositions and methods for treatment of HCV and other viral infections, since viruses represent one of the many circumstances where down-regulation of gene target expression is desirable. The present invention satisfies this need and provides related advantages that overcome the deficiencies of the prior art.

SUMMARY OF THE INVENTION

In accordance with the present invention, a composition comprising a miRNA expression cassette comprising at least two isolated nucleotide sequences selected from the group consisting of sequences complementary to SEQ ID NOs: 1-5, in a pharmaceutically acceptable carrier is provided. In a preferred embodiment, the cassette comprises at least four isolated sequences. In a particularly preferred embodiment, the cassette comprises all five isolated sequences. In another aspect, the cassette is cloned within a vector. Such vectors include without limitation, AAV vectors, lentiviral vectors, retroviral vectors and AV vectors. Particularly preferred are AAV vectors, selected from the group consisting of serotypes 1-9. Exemplary cassettes cloned within the AAV vectors contain cluster 1, cluster 2 or cluster 5 respectively.

In yet another embodiment of the invention, a method of reducing HCV viral load in a patient is provided. An exemplary method entails administering to the liver of said patient a therapeutically effective amount of a cluster comprising vector which directs cleavage of target HCV mRNA sequences present in said patient, thereby reducing HCV viral load. In one aspect, the vector may be directly introduced into the liver of said patient. Alternatively, the vector may be introduced via intravenous infusion.

BRIEF DESCRIPTION OF THE FIGURES

FIG. 5: In vivo inhibition of RLuc reporters by miRNAs targeting HCV. HDTV injections of Balb/c mice were performed using HCV-miR Cluster1+Intron (12 µg), HCV-miR Cluster 2 plasmid (12 µg), or pUC19 (12 µg), and one of the RLuc-HCV fusion reporter plasmids (12 µg) or psiCheck plasmid (12 µg) in a volume of 2 ml PBS. Two days later, animals were sacrificed, livers harvested, and liver lysates were assayed for both FFLuc and RLuc activity. Normalized RLuc expression in the animals that received the pUC19 negative control plasmid was set as 100% activity or 0% inhibition of the target, and the percent inhibition achieved by each miRNA was compared to the pUC19 control. (A) Inhibitory activity of anti-HCV miRNAs when expressed from HCV-miR Cluster 1+Intron against individual reporter plasmids, the reporter encoding all 5 HCV targets, or a plasmid encoding no HCV targets (psiCheck). (B) Inhibitory activity of anti-HCV miRNAs when expressed from HCV-miR Cluster 2 against individual reporter plasmids, the reporter encoding all 5 HCV targets, or a plasmid encoding no HCV targets (psiCheck).

Figure 1:
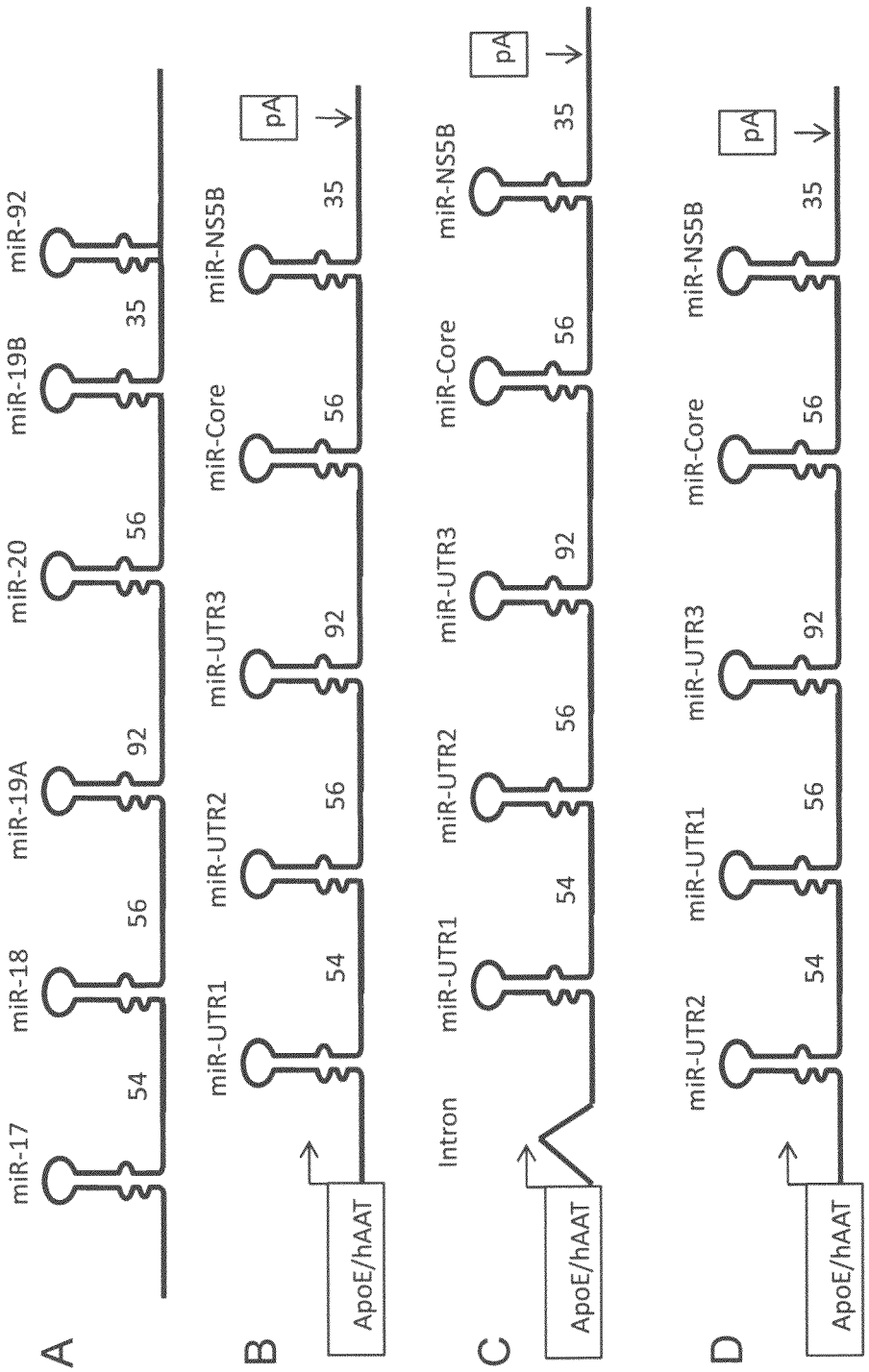
FIG. 1: Schematic of the miR-17-92 primary RNA and the artificial HCV-mRNA clusters. (A) Structure of endogenous miR-17-92 polycistron. (B) Structure of HCV-miR Cluster 1. (C) Structure of HCV-miR Cluster 1+Intron. (D) Structure of HCV-miR Custer 2. Numbers in between pre-miRNAs represent nucleotides. MiRNA stems are not drawn to scale and secondary structures are approximate. ApoE, apolipoprotein E hepatic control region; hAAT, alpha-one antitrypsin promoter; pA, bovine growth hormone polyadenylation signal.

Mice were injected with a plasmid expressing HCV-miRNA Cluster 1 (lane 2), HCV-miRNA Cluster 1+Intron (lane 3) or pUC19 (lane 4). Synthetic siRNAs were used as probe-specific positive controls: 0.4 fmole (lane 5), 2.0 fmole (lane 6), 10.0 fmole (lane 7), 50.0 fmole (lane 8, D only). A radiolabeled RNA marker was included (lane 1). The miRNA transcripts were detected using radiolabeled oligonucleotide probes specific for the anti-sense strand: (A) miR-UTR1, (B) miR-UTR2, (C) miR-UTR3, (D) miR-Core, (E) miR-NS2B. Blots were stripped and reprobed with a U6 snRNA probe to confirm equal sample loading.

Figure 7:
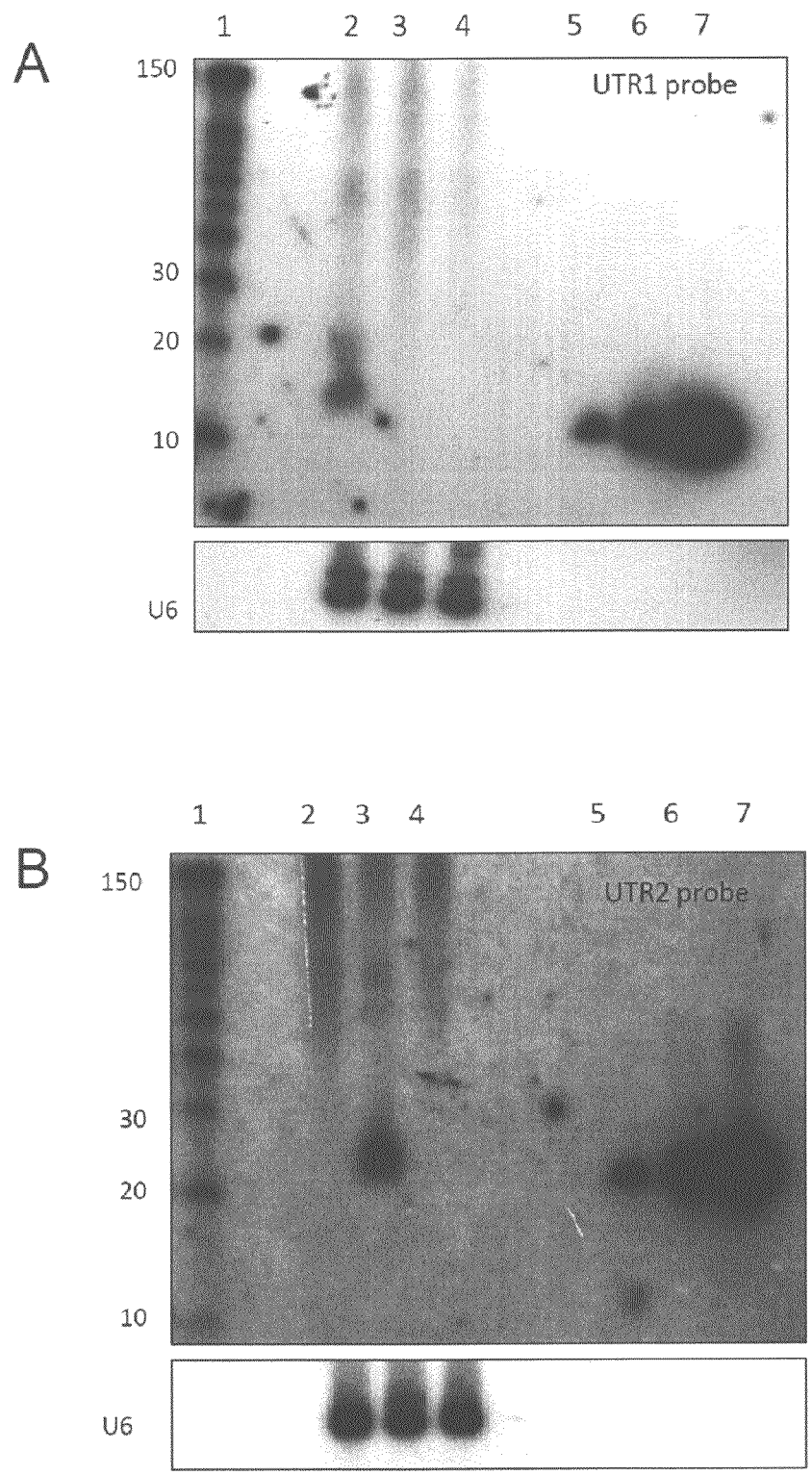

FIG. 7: (A-B) Northern blot analyses of miRNA transcripts in murine liver RNA.

Mice were injected with a plasmid expressing HCV-miRNA Cluster 1+Intron (lane 2), HCV-miRNA Cluster 2 (lane 3) or pUC19 (lane 4). Synthetic siRNAs were used as probe-specific positive controls: 0.4 fmole (lane 5), 2.0 fmole (lane 6), 10.0 fmole (lane 7). A radiolabeled RNA marker was included (lane 1). The miRNA transcripts were detected using radiolabeled oligonucleotide probes specific for the anti-sense strand: (A) miR-UTR1, (B) miR-UTR2.

FIGS. 8A and 8B: FIG. 8A: Sequence information for Cluster 1 (SEQ ID NO: 30) FIG. 8B: Sequence information for Cluster 2(SEQ ID NO: 31 ).

Figure 9:
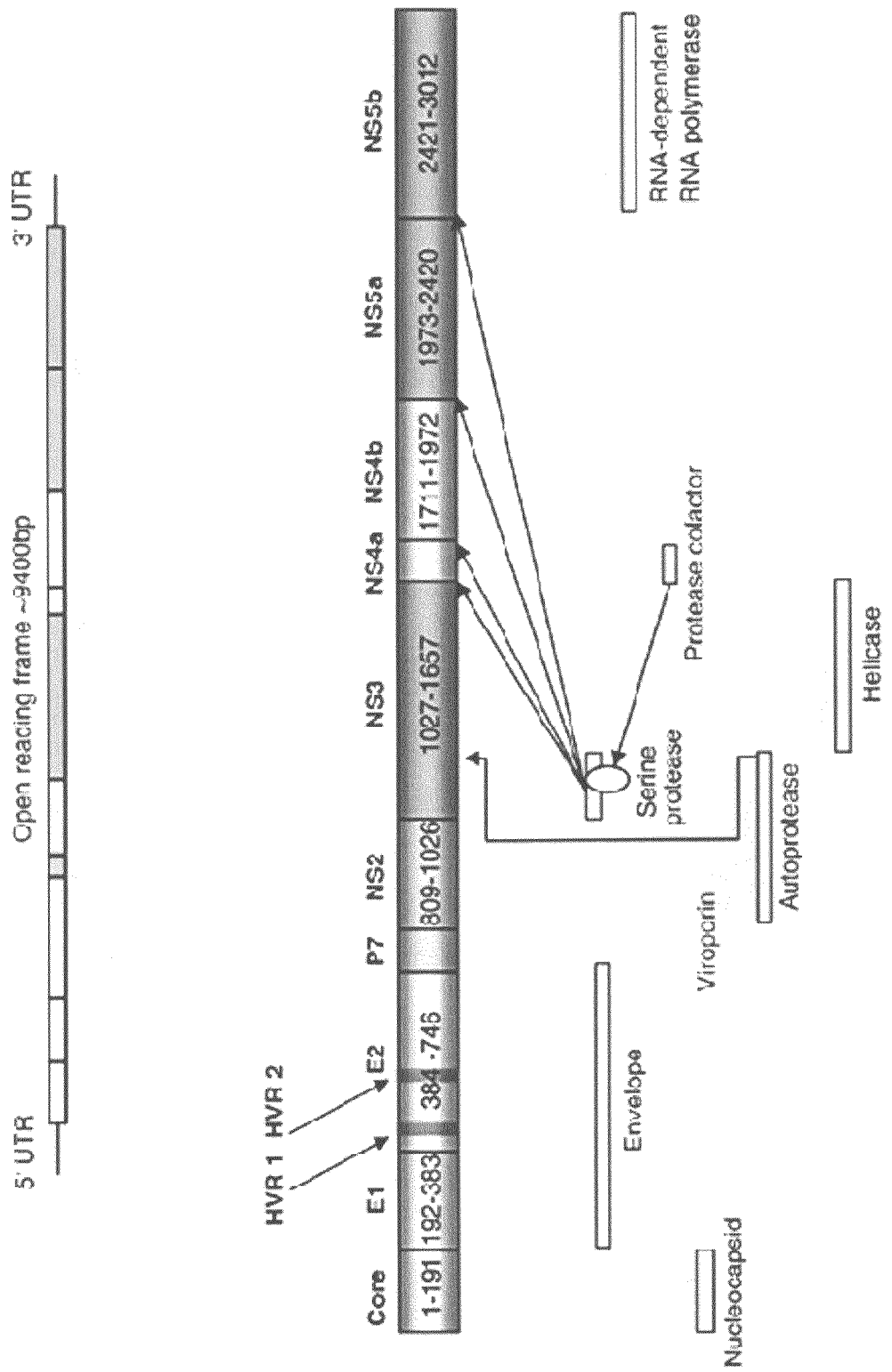

FIG. 9: A schematic diagram of the HCV genome. HCV sequence information is available in GenBank.

Figure 10:
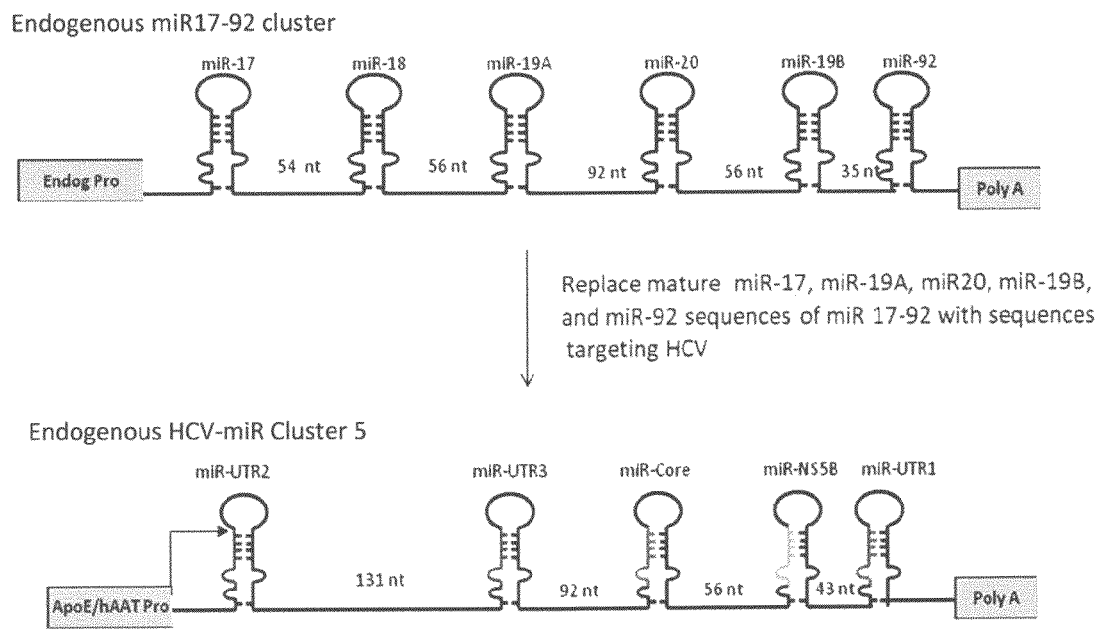

FIG. 10. Construction of HCV-miRNA Cluster 5 encoding five anti-HCV miRNAs. The miRNAs used in Cluster 1 were utilized. The difference is the last miRNA (miR-92) is employed rather than the second miRNA position (miR-18) as a scaffold for miR-UTR-1. Thus this cluster contains miR-UTR2, miR-UTR3, MiR-Core, MiR-NSSB, and miR-UTR1.

Figure 11:
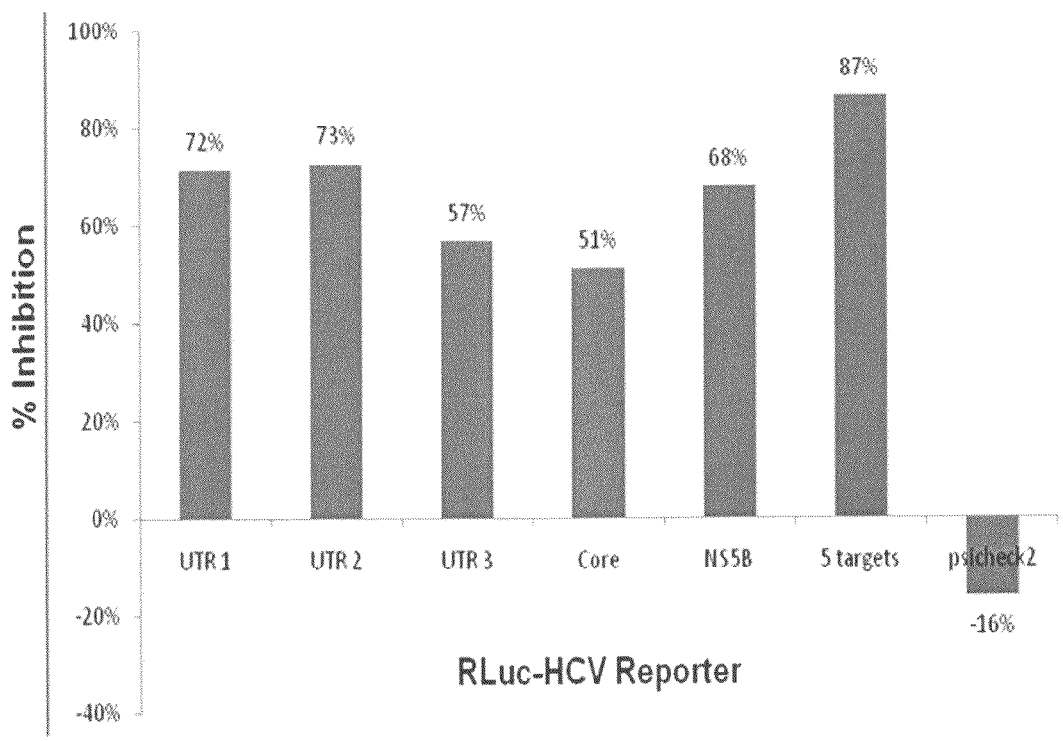

FIG. 11. A graph showing in vitro inhibition of RLuc-HCV reporter plasmids by HCV-miRNA-Cluster 5.

Figure 12:
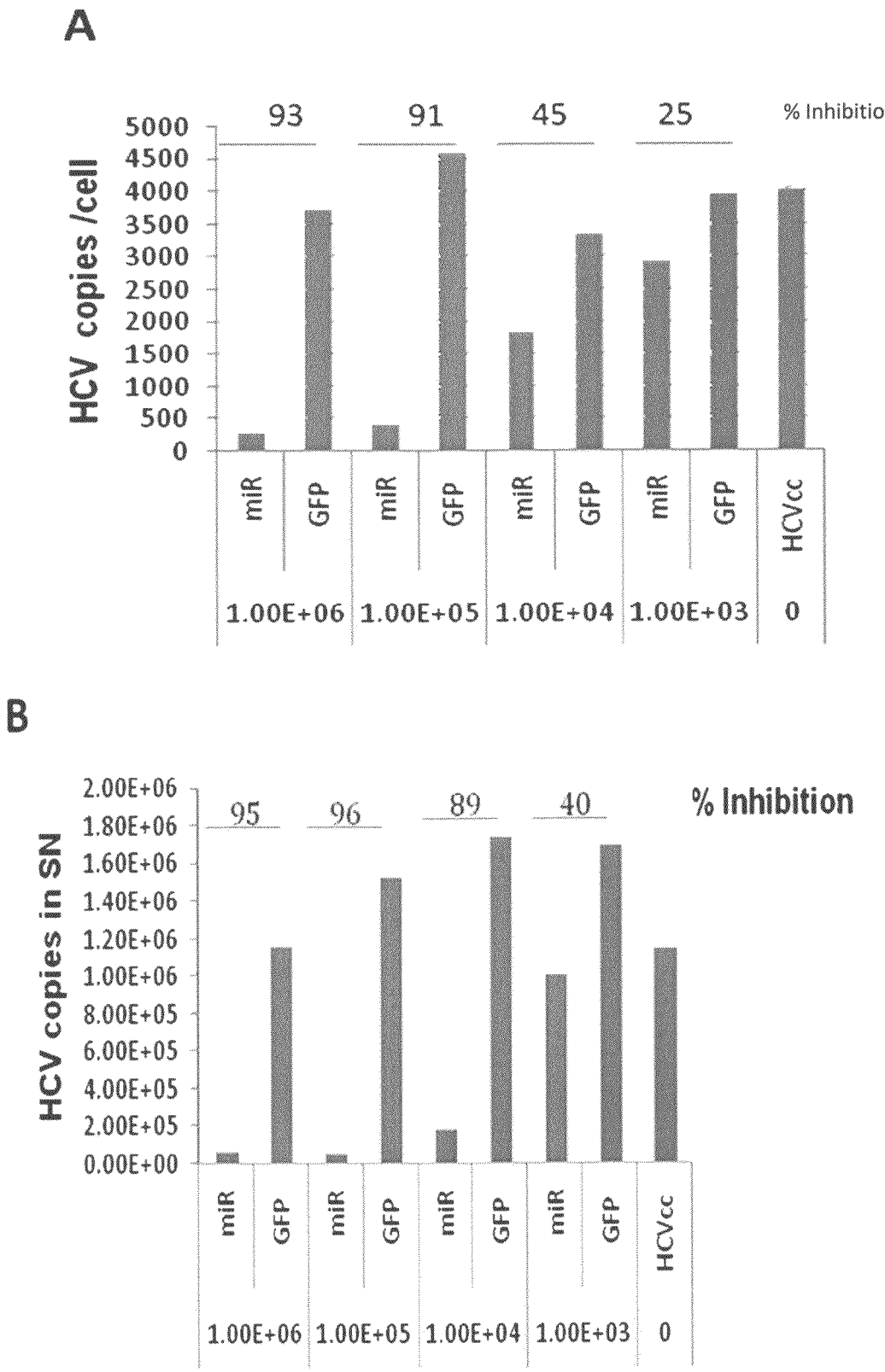

FIG. 12. AAV vectors expressing HCV-mRNA-Cluster 5 are effective to inhibit HCVcc replication.

FIGS. 13A to 13E. Sequence information for AAV vectors (13A-13D) comprising Cluster 5 (FIG. 13E).

Figure 14:
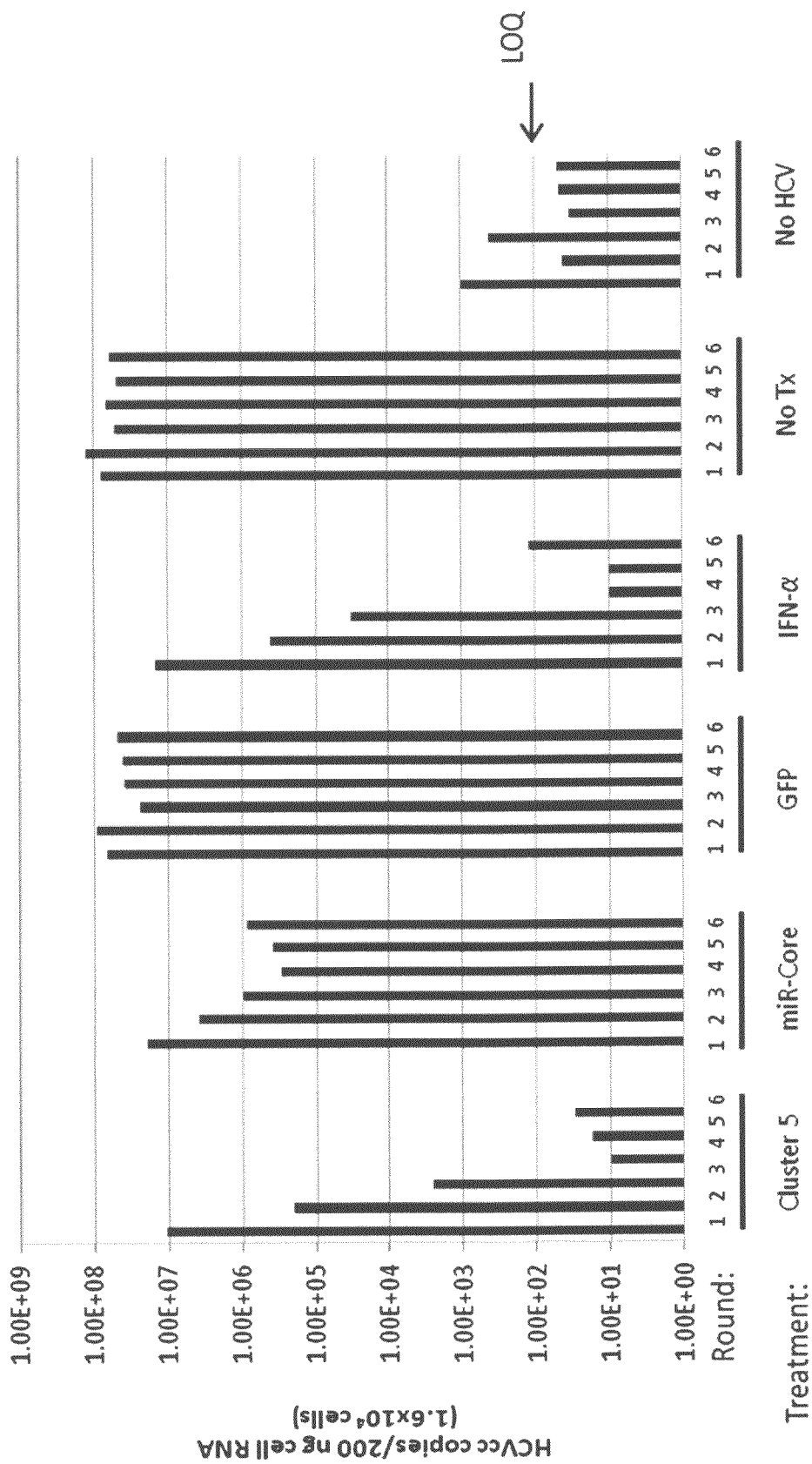

FIG. 14. A graph showing that AAV-vectors expressing HCV-miRNA-Cluster 5 eliminate HCVcc from infected cells.

Figure 15:
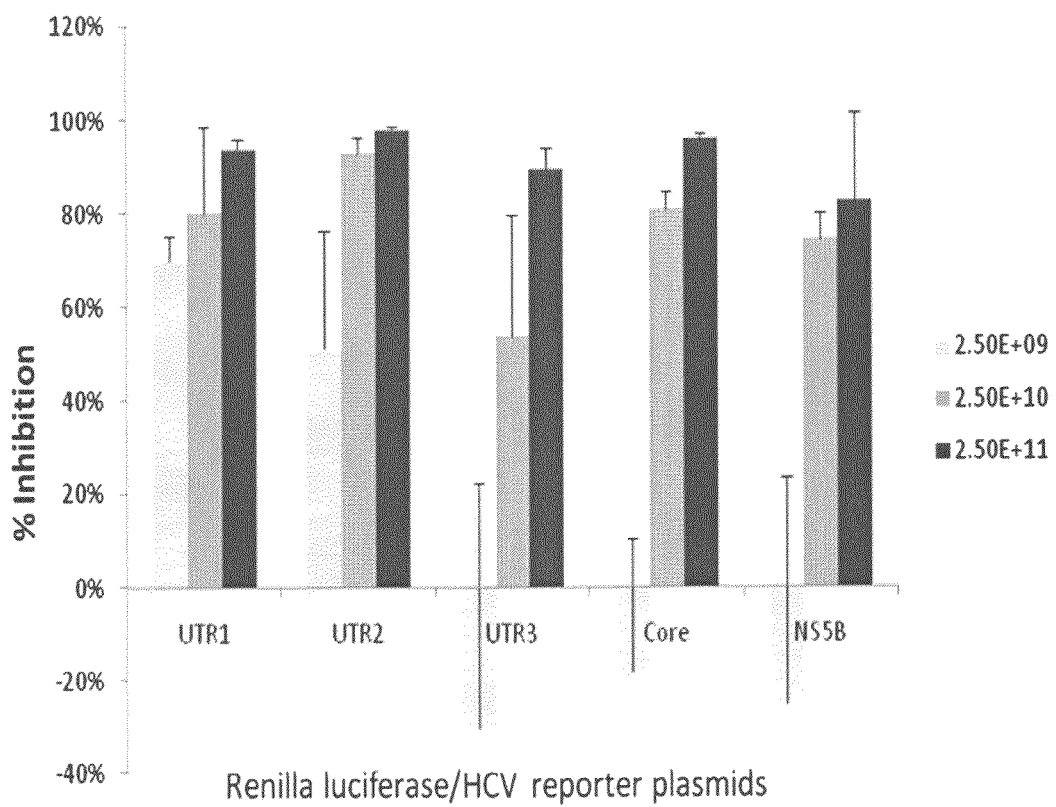

FIG. 15. A graph showing that scAAV8-HCV-miRNA-Cluster 5 silences all 5 target sequences in vivo.

Figure 16:
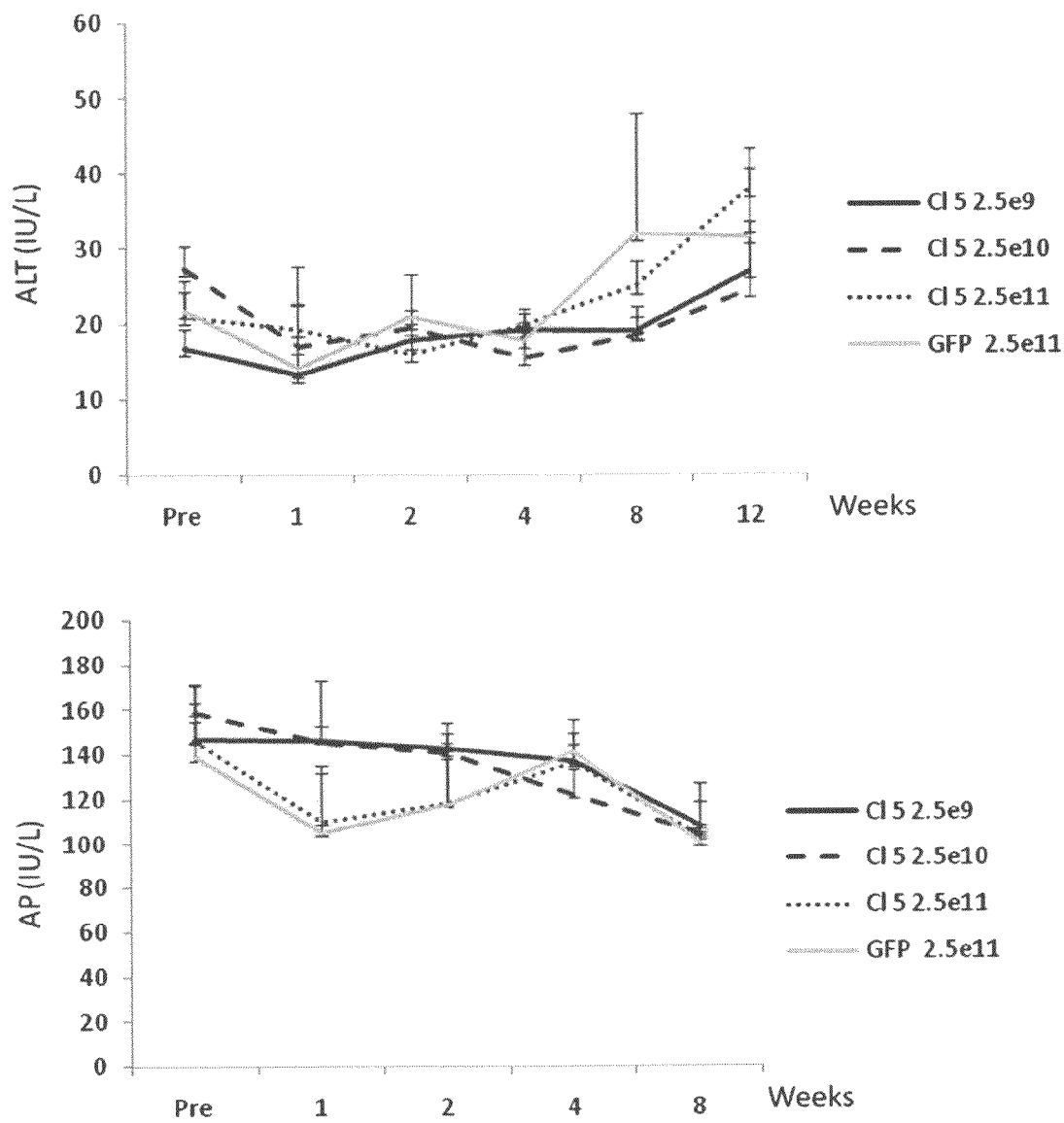

FIG. 16. A pair of graphs showing that scAAV8-HCV-miRNA-Cluster 5 can be safely delivered to the liver. Female C57/B16 mice (6-8 wk) were injected with one of three doses of scAAV8-HCV-miR-Cluster 5: $2.5 \times 10^9$ vg/mouse, $2.5 \times 10^{10}$ vg/mouse, $2.5 \times 10^{11}$ vg/mouse or $2.5 \times 10^{11}$ vg/mouse of scAAV8-eGFP via the tail vein. Blood collected prior to vector injection and at six different time points post-injection (1, 2, 4, 8, 12, and 27 weeks) was analyzed for (a) alanine amino transferase (ALT), (b) aspartate amino transferase (AST)(not shown), (c) alkaline phosphatase (Alk Phos), and (d) albumin (not shown).

Figure 17:
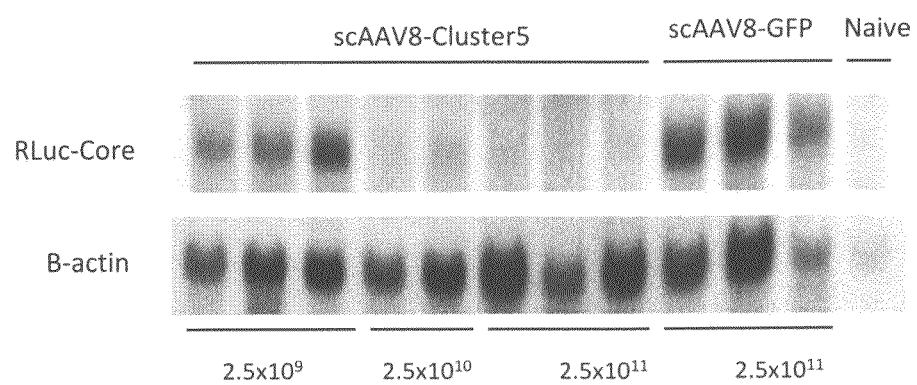

FIG. 17: miRNA and RLuc mRNA analysis of scAAV2-HCV-miR-Cluster 5-injected mice. Analysis of RLuc-Core mRNA. 12 microgram of total cellular RNA was separated on a 1% agarose gel. Millennium RNA markers were used as a molecular weight standard. The RLuc-Core mRNA was detected using an $\alpha$-$P^{32}$-labeled RLuc DNA probe. The membrane was stripped and reprobed with an $\alpha$-$P^{32}$-dCTP labeled $\beta$-actin probe to evaluate equal loading of samples.

Figure 18:
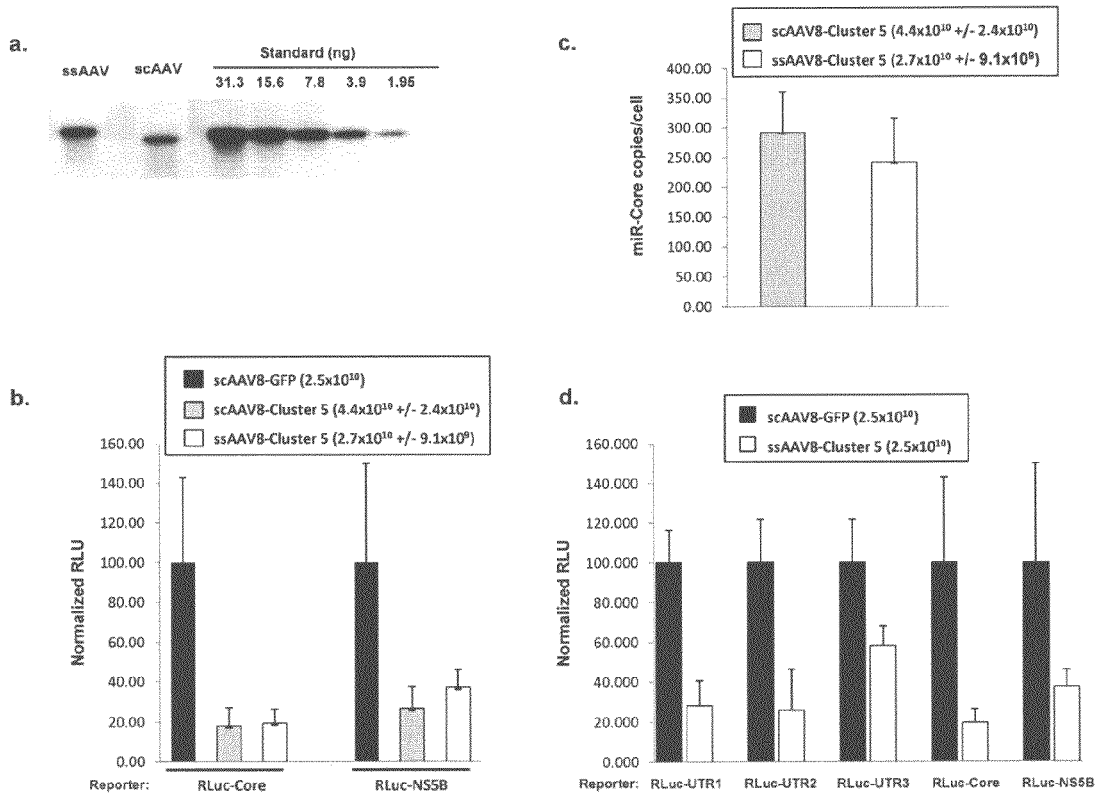

FIG. 18. Comparison of self-complementary and single-stranded AAV-HCV-miR-Cluster 5 vectors in vivo. (a) Quantitative alkaline agarose Southern blot of scAAV8-HCV-miR-Cluster 5 (5 ul of 1:20 dil stock), ssAAV8-HCV-miR-Cluster 5 (5 ul of 1:40 dil stock), and decreasing amounts (31.3-1.95 ng) of a 4175 by DNA fragment containing the HCV-miR-Cluster 5 expression cassette, which were used as copy number standards. This is one of four methods used to quantify the vector titers (b) Female C57/B16 mice (6-8 wk) were injected with AAV- HCV-miR-Cluster 5 vectors whose titers were determined using 4 independent methods and dosed according to the 95% confidence intervals of the results: scAAV8-HCV-miR-Cluster 5 (95% CI=$4.4 \times 1010$+/$2.4 \times 1010$ vg/mouse), ssAAV8-HCV-miR-Cluster 5 (95% CI=$2.7 \times 1010$+/$9.1 \times 109$ vg/mouse), or scAAV-GFP ($2.5 \times 1010$ vg/mouse) via the tail vein. Two weeks later, separate cohorts of mice (n=5) were injected with either the RLuc-Core or RLuc-NSSB reporter plasmid using the HDTV procedure. Mice were sacrificed two days later and liver lysates were analyzed for dual luciferase activity. Two independent liver lysates were prepared and each lysate was analyzed in triplicate; results are reported as the mean and SD. Normalized RLuc expression in mice injected with AAV-GFP was set as 100% activity. (c) Levels of miR-Core in mouse liver quantified using a custom QRT-PCR assay. (d) Female C57/B16 mice (6-8 wk) were injected with of ssAAV8-HCV-miR-Cluster 5 ($2.5 \times 1010$ vg/mouse) or scAAV-GFP ($2.5 \times 1010$ vg/mouse) via the tail vein. Two weeks later, separate cohorts of mice (n=5) were injected with either the RLuc-UTR1, RLuc-UTR2, RLuc-UTR3, RLuc-Core, or RLuc-NSSB reporter plasmid using the HDTV procedure. Mice were sacrificed two days later and liver lysates were analyzed for dual luciferase activity. Two independent liver lysates were prepared and each lysate was analyzed in triplicate; results are reported as the mean and SD. Normalized RLuc expression in mice injected with AAV-GFP was set as 100% activity.

DETAILED DESCRIPTION OF THE INVENTION

The present invention provides compositions and methods for reducing the amount of a viral genome in a target cell, where the target cell may be present in vitro or in vivo. The term "reducing the amount of" indicates that the level or quantity of the viral genome in the target cell is reduced by at least about 2-fold, usually by at least about 5-fold, possibly even 10-fold, 15-fold, 20-fold, 50-fold, or 100-fold or more, as compared to a control (i.e., an untreated target cell). In a preferred embodiment, the viral genome comprises HCV.

As described throughout the application, miRNAs are a class of 15-30 nt non-coding RNAs (ncRNAs) that exist in a variety of organisms, and are conserved throughout evolution. They are processed from hairpin precursors (pre-miRNA) which are derived from primary transcripts (pri-miRNA) through sequential cleavage by RNAse III enzymes. Many miRNAs can be encoded in intergenic regions, hosted within introns of pre-mRNAs or within ncRNA genes. MiRNAs also tend to be clustered and transcribed as polycistrons and often have similar spatial temporal expression patterns. They have been found to have roles in a variety of biological processes including developmental timing, differentiation, apoptosis, cell proliferation, organ development, and metabolism by negatively regulating gene expression by base-pairing to a target sequence in an mRNA. In certain embodiments of the instant invention, this negative regulation is exploited for therapeutic advantage.

Previous data indicate that maximal silencing can be achieved with miRNA-based RNAi effectors without the build-up of excessive precursor and non-processed products that may disrupt miRNA biogenesis and function. Since many miRNAs exist naturally in clusters and are transcribed as polycistronic pri-miRNAs in the nucleus by tissue specific pol II promoters, their genomic organization makes them an attractive system for treating "error-prone" RNA viruses. (33). This allows for the simultaneous expression of multiple miRNAs from a single transcription unit and avoids the use of repetitive promoter sequences. This configuration is ideally suited for targeting many different regions of viral genomes and is more likely to yield a potent treatment for viruses such as HCV, HIV, and poliovirus. Recently, two different endogenous miRNA clusters (miR106b-93-25 and miR17-92) have been manipulated to express multiple anti-HIV miRNAs (34; 35). Inhibition of HIV target sequences ranged from ~0-80% for different anti-HIV-miRNAs, and silencing activity of individual miRNAs improved when the secondary structure of the endogenous pre-miRNA stems were mimicked, as opposed to having fully-paired stem structures (34).

One feature of the present invention comprises the miR17-92 cluster to allow development of an artificial polycistronic miRNA for treating HCV infection. In certain embodiments, the first five pre-miRNAs of the cluster have been replaced with inhibitory RNAs targeting HCV, and four out of the five miRNAs are active, inhibiting their cognate sequences by up to 80% in vitro. The in vivo activity of an artificial polycistronic miRNA cluster was evaluated, and up to 97% inhibition of the HCV targets was observed. The miRNAs are specific for their cognate sequences and fail to inhibit the many non-target sequences tested. In addition, the correct strands of the miRNAs are incorporated into the RISC. In another embodiment, HCV inhibitory RNAs are inserted at miR-17 (UTR-2), miR-19A (UTR-3), miR-20 (Core), miR-19B (NSSB) and miR-92 (UTR-1). In this construct, referred to herein as cluster 5, the miR-18 loop is deleted. However, in an alternative embodiment, this loop may be left intact. In contrast to clusters 1 and 2, all five anti-HCV inhibitory RNAs in cluster 5 were active and inhibited expression of their cognate targets. These findings suggest that the HCV miRNA clusters are active and that off-target effects and toxicity are unlikely using these miRNAs. The findings described herein are exemplified for HCV infection, but can be broadly applied and modified to inhibit other viruses and cellular gene products associated with disease states.

Typically, inhibition of target sequences by RNAi (i.e. miRNAs) requires a high degree of sequence homology between the target sequence and the anti-sense strand of the RNAi molecules. Most important is the seed region 2-8 nt from 5' end. In some embodiments, such homology is higher than 70%, and may be higher than 75%. Preferably, homology is higher than 80%, or 85% or even 90%. More preferably, sequence homology between the target sequence and the sense strand of the RNAi is higher than 90%, 91%, 92%, 93%, 94%, 95%, 96%, 97%, 98% or 99%

Certain embodiments of the invention address a major problem of current anti-viral therapies, which is the emergence of resistant variants, known generally as escape mutants. The high mutation rate of viruses and the use of single drug treatments allow escape mutants to emerge. Thus, one aspect of the present invention neutralizes emergent escape mutants. For example, use of miRNAs targeting multiple regions of the HCV genome can be expressed simultaneously on one polycistronic miRNA construct allowing the targeting of multiple regions within the HCV genome. Thus, expression of multiple miRNA constructs in one transcriptional unit comprises an aspect of the invention. In the HCV context, using the miR-17-92 cluster as a scaffold, multiple constructs can be made based on the hairpin structures. In addition to the miRNA clusters disclosed herein, particular embodiments of the invention feature multiple miRNAs, wherein the pre-miR-18 hairpin is excluded from targeting, and miR-92 is used as a basis for inhibition. See FIG. 10. FIG. 1A shows the natural miRNA-17-92 cluster, which can be modified at one or more of the first, third, fourth, fifth, and sixth hairpin structures. In some embodiments of this invention the selection of multiple RNAi sequences (i.e., miRNAs) to treat viral infections can be chosen based on the emergence of escape mutants from treatment of infected cells single sequence of RNAi. Emergent escape mutants are determined by treatment with an expression construct containing a single sequence of RNAi after the cells have been infected with virus. Cells containing resistant viruses that emerge are harvested and the viral genomes sequenced.

I. Definitions

The following definitions are provided to facilitate an understanding of the present invention. Unless defined otherwise, all technical and scientific terms used herein have the same meaning as commonly understood by one of ordinary skill in the art to which this invention belongs. Generally, conventional methods of molecular biology, microbiology, recombinant DNA techniques, cell biology, and virology within the skill of the art are employed in the present invention. Such techniques are explained fully in the literature, see, e.g., Maniatis, Fritsch & Sambrook, Molecular Cloning: A Laboratory Manual (1982); DNA Cloning: A Practical Approach, Volumes I and II (D. N. Glover, ed. 1985); Oligonucleotide Synthesis (M. J. Gait, ed. 1984); Nucleic Acid Hybridization (B. D. Hames & S. J. Higgins, eds. (1984)); Animal Cell Culture (R. I. Freshney, ed. 1986); and RNA Viruses: A Practical Approach, (Alan, J. Cann, Ed., Oxford University Press, 2000).

For purposes of the invention, "Nucleic acid", "nucleotide sequence" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. Alternatively, this term may refer to a DNA that has been sufficiently separated from (e.g., substantially free of) other cellular components with which it would naturally be associated. "Isolated" is not meant to exclude artificial or synthetic mixtures with other compounds or materials, or the presence of impurities that do not interfere with the fundamental activity, and that may be present, for example, due to incomplete purification. When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

According to the present invention, an isolated or biologically pure molecule or cell is a compound that has been removed from its natural milieu. As such, "isolated" and "biologically pure" do not necessarily reflect the extent to which the compound has been purified. An isolated compound of the present invention can be obtained from its natural source, can be produced using laboratory synthetic techniques or can be produced by any such chemical synthetic route.

The term "promoter" or "promoter region" generally refers to the transcriptional regulatory regions of a gene. The "promoter region" may be found at the 5' or 3' side of the coding region, or within the coding region, or within introns. Typically, the "promoter region" is a nucleic acid sequence which is usually found upstream (5') to a coding sequence and which directs transcription of the nucleic acid sequence into mRNA. The "promoter region" typically provides a recognition site for RNA polymerase and the other factors necessary for proper initiation of transcription. Promoters useful in some embodiments of the present invention may be tissue-specific or cell-specific. The term "tissue-specific" as it applies to a promoter refers to a promoter that is capable of directing selective expression of a nucleotide sequence of interest to a specific type of tissue in the relative absence of expression of the same nucleotide sequence of interest in a different type of tissue (e.g., liver). The term "cell-specific" as applied to a promoter refers to a promoter which is capable of directing selective expression of a nucleotide sequence of interest in a specific type of cell in the relative absence of expression of the same nucleotide sequence of interest in a different type of cell within the same tissue (see, e.g., Higashibata, et al., J. Bone Miner. Res. January 19(1):78-88 (2004); Hoggatt, et al., Circ. Res., Dec. 91(12):1151-59 (2002); Sohal, et al., Circ. Res. July 89(1):20-25 (2001); and Zhang, et al., Genome Res. Jan 14(1):79-89 (2004)). The term "cell-specific" when applied to a promoter also means a promoter capable of promoting selective expression of a nucleotide sequence of interest in a region within a single tissue. Alternatively, promoters may be constitutive or regulatable. Additionally, promoters may be modified so as to possess different specificities.

The term "vector" relates to a single or double stranded circular nucleic acid molecule that can be infected, transfected or transformed into cells and replicate independently or within the host cell genome. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. An "expression vector" is a specialized vector that contains a gene or nucleic acid sequence with the necessary regulatory regions needed for expression in a host cell. The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The terms "miRNA" and "microRNA" refer to about 10-35 nt, preferably about 15-30 nt, and more preferably about 19-26 nt, non-coding RNAs derived from endogenous genes encoded in the genomes of plants and animals. They are processed from longer hairpin-like precursors termed pre-miRNAs that are often hundreds of nucleotides in length. MicroRNAs assemble in complexes termed miRNPs and recognize their targets by antisense complementarity. These highly conserved, endogenously expressed RNAs are believed to regulate the expression of genes by binding to the 3'-untranslated regions (3'-UTR) of specific mRNAs. Without being bound by theory, a possible mechanism of action assumes that if the microRNAs match 100% their target, i.e. the complementarity is complete, the target mRNA is cleaved, and the miRNA acts like a siRNA. However, if the match is incomplete, i.e. the complementarity is partial, then the translation of the target mRNA is blocked. The manner by which a miRNA base-pairs with its mRNA target correlates with its function: if the complementarity between a mRNA and its target is extensive, the RNA target is cleaved; if the complementarity is partial, the stability of the target mRNA in not affected but its translation is repressed.

The term "RNA interference" or "RNAi" refers generally to a process or system in which a RNA molecule changes the expression of a nucleic acid sequence with which RNA molecule shares substantial or total homology. The term "RNAi agent" refers to an RNA sequence that elicits RNAi.

An "siRNA" refers to a molecule involved in the RNA interference process for a sequence-specific post-transcriptional gene silencing or gene knockdown by providing small interfering RNAs (siRNAs) that have homology with the sequence of the targeted gene. Small interfering RNAs (siRNAs) can be synthesized in vitro or generated by ribonuclease III cleavage from longer dsRNA and are the mediators of sequence-specific mRNA degradation. Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Applied Biosystems (Foster City, Calif., USA), Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Specific siRNA constructs for inhibiting HCV may be between 15-35 nucleotides in length.

"Pri-miRNAs" are several hundred to thousands of base pair in size. Pri-miRNA contains at least 1, and up to 6, nucleotide hairpin loop structures when transcribed from polycistronic units. They can be composed of multiple miRNAs, and in a particular arrangement of the invention five miRNAs are processed from one nucleic acid sequence. These sequences can also contain siRNA nucleic acids that repress gene transcription once processed in the RNAi system.

As used herein, "pharmaceutical formulations" include formulations for human and veterinary use which exhibit no significant adverse toxicological effect. The phrase "pharmaceutically acceptable formulation" as used herein refers to a composition or formulation that allows for the effective distribution of the nucleic acid molecules of the instant invention in the physical location most suitable for their desired activity. The phrase "pharmaceutically acceptable" is used to indicate that the carrier can be administered to the subject without exerting significant adverse toxicological effects. The term "therapeutically effective amount" is the amount present that is delivered to a subject to provide the desired physiological response (e.g., viral load reduction). Methods for preparing pharmaceutical compositions are within the skill in the art, for example as described in Remington's Pharmaceutical Science, 18th ed., Mack Publishing Company, Easton, Pa. (1990), and The Science and Practice of Pharmacy, 2003, Gennaro et al.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween 80, Polysorbate 80), emulsifier, buffer (e.g., Tris HCl, acetate, phosphate), bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, 20th Edition, (Lippincott, Williams and Wilkins), 2000; Liberman, et al., Eds., Pharmaceutical Dosage Forms, Marcel Decker, New York, N.Y., 1980; and Kibbe, et al., Eds., Handbook of Pharmaceutical Excipients (3.sup.rd Ed.), American Pharmaceutical Association, Washington, 1999.

The term "treating" or "to treat" as used herein means activity resulting in the prevention, reduction, partial or complete alleviation or cure of a disease or disorder. The term "modulate" means altering (i.e., increasing or decreasing) the biological activity of a system, e.g., viral infection or reduction of viral load. Activity can be modulated by a variety of mechanisms such as modifying expression levels through RNAi.

With respect to single-stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (see Sambrook et al. (2001) *Molecular Cloning. A Laboratory Manual*, Cold Spring Harbor, N.Y.: Cold Spring Harbor Laboratory Press):

$$T_m = 81.5° C. + 16.6 \log [Na+] + 0.41(\% G+C) - 0.63 (\% \text{formamide}) - 600/\#bp \text{ in Duplex}$$

As an illustration of the above formula, using [Na+]=[0.368] and 50% formamide, with GC content of 42% and an average probe size of 200 bases, the $T_m$ is 57° C. Depending upon the specific sequence involved, the $T_m$ of a DNA duplex decreases by 0.5-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5× Denhardt's solution, 0.5% SDS and 100 µg/ml denatured salmon sperm DNA at 42° C., and washed in 2×SSC and 0.5% SDS at 55° C. for 15 minutes. A high-stringency hybridization is defined as hybridization in 6×SSC, 5× Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5× Denhardt's solution, 0.5% SDS and 100 µg/ml denatured salmon sperm DNA at 42° C., and washed in 0.1× SSC and 0.5% SDS at 65° C. for 15 minutes.

"Corresponding" means identical to or complementary to the designated sequence. The sequence may be generated in any manner, including chemical synthesis, DNA replication, reverse transcription or a combination thereof. Being "Complementary" means that a nucleic acid, such as DNA and RNA, encodes the only corresponding base pair that non-covalently connects sequences by two or three hydrogen bonds. There is only one complementary base for any of the bases found in DNA and in RNA, and skilled artisans can reconstruct a complementary strand for any single stranded nucleic acid.

The present invention also includes active portions, fragments, derivatives and functional or non-functional mimetics of the miRNAs of the invention. A "fragment" or "portion" of a sequence means a stretch of residues of at least about five to seven contiguous residues, often at least about seven to nine contiguous residues, typically at least about nine to fifteen contiguous residues and, most preferably, at least about fourteen or more contiguous residues.

For purposes of the present invention, "a" or "an" entity refers to one or more of that entity; for example, "a cDNA" refers to one or more cDNA or at least one cDNA. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the functional and novel characteristics of the sequence.

A "subject" or "patient" includes, but is not limited to animals, including mammalian species such as murine, porcine, ovine, bovine, canine, feline, equine, human, and other primates.

The phrase "viral load" is a measure of the severity of a viral infection, and can be calculated by estimating the amount of virus in a patient. Determination of viral load is part of therapy monitoring during chronic viral infections A "derivative" of a polypeptide, polynucleotide or fragments thereof means a sequence modified by varying the sequence of the construct, e.g. by manipulation of the nucleic acid encoding the protein or by altering the protein itself. Such derivatives of the natural sequence may involve insertion, addition, deletion or substitution of one or more amino acids, and may or may not alter the essential activity of original the polypeptide. "Derivatives" of a gene or nucleotide sequence refers to any isolated nucleic acid molecule that contains significant sequence similarity to the gene or nucleotide sequence or a part thereof. In addition, "derivatives" include such isolated nucleic acids containing modified nucleotides or mimetics of naturally-occurring nucleotides.

The term "functional" as used herein implies that the nucleic or amino acid sequence is functional for the recited assay or purpose.

"Peptide" and "polypeptide" are used interchangeably herein and refer to a compound made up of a chain of amino acid residues linked by peptide bonds. An "active portion" of a polypeptide means a peptide that is less than the full length polypeptide, but which retains measurable biological activity and retains biological detection.

The term "oligonucleotide" as used herein refers to sequences, primers and probes of the present invention, and is defined as a nucleic acid molecule comprised of two or more ribo- or deoxyribonucleotides, preferably more than three. The exact size of the oligonucleotide can depend on various factors and on the particular application and use of the oligonucleotide.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "gene" refers to a nucleic acid comprising an open reading frame encoding a polypeptide, including both exon and (optionally) intron sequences. The nucleic acid may also optionally include non coding sequences such as promoter or enhancer sequences. The term "intron" refers to a DNA sequence present in a given gene that is not translated into protein and is generally found between exons.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, depending on the complexity of the target sequence, the oligonucleotide probe typically contains about 10-50 or more nucleotides, more preferably, about 15-25 nucleotides.

The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The terms "percent similarity", "percent identity" and "percent homology" when referring to a particular sequence are used as set forth in the University of Wisconsin GCG software program.

The term "delivery" as used herein refers to the introduction of foreign molecule (i.e., protein containing nanoparticle) into cells. The term "administration" as used herein means the introduction of a foreign molecule into a cell. The term is intended to be synonymous with the term "delivery". Administration also refers to screening assays of the invention (e.g., routes of administration such as, without limitation, intravenous, intra-arterial, intramuscular, subcutaneous, intrasynovial, infusion, sublingual, transdermal, oral, or topical).

The term "kit" refers to a combination of reagents and other materials.

II. Therapeutic Uses of miRNAs and Polycistronic miRNA Constructs

The polycistronic constructs targeting HCV may be used according to this invention, for example, as therapeutic agents that modulate viral infection. The invention also encompasses use of polycistronic miRNAs expressed from transcriptional units inserted into nucleic acid-based vectors. In a preferred embodiment of the present invention, the polycistronic miRNAs may be administered to a patient via infusion in a biologically compatible carrier. The miRNAs may be administered alone or in combination with other agents known to have anti-viral effects. An appropriate composition in which to deliver miRNAs may be determined by a medical practitioner upon consideration of a variety of physiological variables as contemplated hereinbelow. A variety of compositions well suited for different applications and routes of administration are well known in the art and are described hereinbelow. The preparation containing the polycistronic miRNAs contains a physiologically acceptable matrix and is preferably formulated as a pharmaceutical preparation.

Nucleic acid molecules encoding the miRNAs of the invention may be prepared by using recombinant DNA technology methods. The availability of nucleotide sequence information enables preparation of nucleic acid-based molecules of the invention by a variety of means.

The polycistronic miRNAs may be used for a variety of purposes in accordance with the present invention. In a preferred embodiment of the invention, a nucleic acid delivery vehicle (i.e., an expression vector) for modulating viral infection is provided wherein the expression vector comprises a nucleic acid sequence coding the polycistronic miRNAs, or a functional fragments thereof as described herein. Administration of polycistronic miRNAs or derivatives thereof encoding expression vectors to a patient results in the expression of miRNAs which serve to inhibit viral replication, particularly alleviating HCV infection.

In a preferred embodiment of the invention, the expression vector comprising nucleic acid sequence encoding the polycistronic miRNA constructs for reduction of virus infection, is a viral vector. Viral vectors which may be used in the present invention include, but are not limited to, adenoviral vectors (with or without tissue specific promoters/enhancers), adeno-associated virus (AAV) vectors of multiple serotypes (e.g., AAV-1-9) and recombinant AAV vectors, lentivirus vectors and pseudo-typed lentivirus vectors (e.g., Ebola virus, vesicular stomatitis virus (VSV), and feline immunodeficiency virus (FIV)), herpes simplex virus vectors, vaccinia virus vectors, and retroviral vectors. In preferred embodiments, rAAV-2 will be used in in vitro assays, rAAV-8 will be used in mouse studies and rAAV-6, 8, or 9 will be used as a carrier for in vivo administration of the miRNAs of the invention to primates.

For some applications, an expression construct may further comprise regulatory elements which serve to drive expression in a particular cell or tissue type. Such regulatory elements are known to those of skill in the art and discussed in depth in Sambrook et al. (1989) and Ausubel et al. (1992). The incorporation of tissue specific regulatory elements in the expression constructs of the present invention provides for at least partial tissue tropism for the expression polycistronic miRNAs. For example, the miRNA constructs can be subcloned into a vector downstream of a tissue (i.e., liver) specific promoter/enhancer to treat HCV. A preferred embodiment comprises the ApoE, apolipoprotein E, hepatic control region and the hAAT, alpha-one antitrypsin promoter. Additionally, polyadenylation sequences can be inserted downstream of the miRNA cluster in miRNA and polycistronic miRNA clusters. Preferably, the bovine growth hormone polyadenylation sequence is used in certain constructs of the invention.

III. Pharmaceutical Compositions

The expression vectors of the present invention may be incorporated into pharmaceutical compositions that may be delivered to a subject. In a particular embodiment of the present invention, pharmaceutical compositions comprising isolated nucleic acids which enable the recipient to produce therapeutically effective miRNAs that modulate viral infection (i.e., viral load) in the recipient are provided. The compositions may be administered alone or in combination with at least one other agent, such as a stabilizing compound, which may be administered in any sterile, biocompatible pharmaceutical carrier, including, but not limited to, saline, buffered saline, dextrose, and water. In preferred embodiments, the pharmaceutical compositions also contain a pharmaceutically acceptable excipient. Such excipients include any pharmaceutical agent that does not itself induce an immune response harmful to the individual receiving the composition, and which may be administered without undue toxicity. Pharmaceutically acceptable excipients include, but are not limited to, liquids such as water, saline, glycerol, sugars and ethanol.

Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences (Mack Pub. Co., 18th Edition, Easton, Pa. (1990).

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions. The pharmaceutical compositions of the present invention may be manufactured in any manner known in the art (e.g., by means of conventional mixing, dissolving, granulating, dragee-making, levigating, emulsifying, encapsulating, entrapping, or lyophilizing processes).

The preparation according to the present invention is especially stable, i.e., it can be allowed to stand in dissolved form for a prolonged time prior to application. The preparation according to the present invention can be made available as a pharmaceutical preparation with the nucleic acid encoding the polycistronic miRNAs in the form of a one-component preparation or in combination with other factors in the form of a multi-component preparation.

Expression vectors comprising polycistronic miRNAs sequences may be administered alone, or in combination with other anti-viral agents. According to the present invention, the expression vectors or combination of therapeutic agents may be administered to the patient alone or in a pharmaceutically acceptable or biologically compatible composition.

After pharmaceutical compositions have been prepared, they may be placed in an appropriate container or kit and labeled for treatment. For administration of polycistronic miRNAs-containing vectors, such labeling would include amount, frequency, and method of administration.

Pharmaceutical compositions suitable for use in the invention include compositions wherein the constructs are contained in an effective amount to achieve the intended therapeutic purpose. Determining a therapeutically effective dose is well within the capability of a skilled medical practitioner using the techniques provided hereinbelow. Therapeutic doses will depend on, among other factors, the age and general condition of the subject, the severity of the viral infection, and the strength of the control sequences regulating the expression levels of the polycistronic miRNAs. Thus, a therapeutically effective amount in humans will fall in a relatively broad range that may be determined by a medical practitioner based on the response of an individual patient to vector-based form of polycistronic miRNAs.

IV. Methods of Treatment and Delivery

Nucleic acids encoding the polycistronic miRNAs either in plasmid or viral vector forms alone or in combination with other agents, may be directly infused into a patient in an appropriate biological carrier, preferably by IV administration. One of skill in the art could readily determine specific protocols for using the miRNAs of the present invention for the therapeutic treatment of a particular patient. In this regard, the compositions may be delivered subcutaneously, epidermally, intradermally, intrathecally, intraorbitally, intramucosally, intraperitoneally, intravenously, intraarterially, orally, intrahepatically or intramuscularly. Other modes of administration include oral and pulmonary administration, suppositories, and transdermal applications.

Dosage levels on the order of about 1 µg/kg to 100 mg/kg of body weight per administration are useful in the treatment of a disease or viral infection. In regard to dosage, the vectors encoding the polycistronic miRNAs of the invention can be administered at a unit dose less than about 75 mg per kg of bodyweight, or less than about 70, 60, 50, 40, 30, 20, 10, 5, 2, 1, 0.5, 0.1, 0.05, 0.01, 0.005, 0.001, or 0.0005 mg per kg of bodyweight, and less than 200 nmol of polycistronic miRNA per kg of bodyweight, or less than 1500, 750, 300, 150, 75, 15, 7.5, 1.5, 0.75, 0.15, 0.075, 0.015, 0.0075, 0.0015, 0.00075, 0.00015 nmol of polycistronic miRNA per kg of bodyweight. Alternatively AAV doses can be determined using vectors genomes/kg, which in turn can be converted to µg capsid protein/kg. The unit dose, for example, can be administered by injection for example, intravenous, intramuscular, intrathecally, or directly into an organ such as the liver.

Delivery of the vectors encoding polycistronic miRNAs directly to an organ can be at a dosage on the order of about 0.00001 mg to about 3 mg per organ, or preferably about 0.0001-0.001 mg per organ, about 0.03-3.0 mg per organ, about 0.1-3.0 mg per organ or about 0.3-3.0 mg per organ. The dosage can be an amount effective modulate viral activity or to treat or prevent a disease or disorder.

One skilled in the art can also readily determine an appropriate dosage regimen for administering the vectors of the invention to a given subject. For example, such vectors can be administered to the subject once, e.g., as a single injection or deposition at or near the site of viral replication. Alternatively, the vectors encoding the polycistronic miRNAs can be administered multiple times to a subject. However, this may require the use of alternative AAV vectors to avoid anti-AAV antibodies that may develop upon initial exposure to the rAAV. It may also be desirable to administer such vectors in conjunction with an immunosuppressive agent in order to suppress this undesired immune response. One skilled in the art will appreciate that the exact individual dosages may be adjusted somewhat depending on a variety of factors, including the specific polycistronic miRNAs being administered, the time of administration, the route of administration, the nature of the formulation, the rate of excretion, the particular infection being treated, the severity of the infection, the pharmacodynamics of the oligonucleotide agent, and the age, sex, weight, and general health of the patient. Wide variations in the necessary dosage level are to be expected in view of the differing efficiencies of the various routes of administration. For instance, oral administration generally would be expected to require higher dosage levels than administration by intravenous or intravitreal injection. Variations in these dosage levels can be adjusted using standard empirical routines of optimization, which are well-known in the art. Optimum dosages may vary depending on the relative potency of individual compounds, and can generally be estimated based on $EC_{50}$s found to be effective in in vitro and in vivo animal models.

Changes in dosage may result and become apparent from the results of diagnostic assays. For example, the subject can be monitored after administering polycistronic miRNAs composition. Based on information from the monitoring, an additional amount of the composition can be administered.

V. Kits and Articles of Manufacture

Any of the aforementioned compositions or methods can be incorporated into a kit which may contain at least one miRNA sequence or polycistronic transcript. The kit can also contain a vector containing Cluster 1 or Cluster 5. If the pharmaceutical composition in liquid form is under risk of being subjected to conditions which will compromise the stability of the nucleic acid molecules, it may be preferred to produce the finished product containing the vectors in a solid form, e.g. as a freeze dried material, and store the product is such solid form. The product may then be reconstituted (e.g. dissolved or suspended) in a saline or in a buffered saline ready for use prior to administration.

Hence, the present invention provides a kit comprising (a) a first component containing nucleic acids encoding the miRNAs as defined hereinabove, optionally in solid form, and (b) a second component containing saline or a buffer solution (e.g. buffered saline) adapted for reconstitution (e.g. dissolution or suspension) or delivery of said polycistronic miRNAs.

Preferably said saline or buffered saline has a pH in the range of 4.0-8.5, and a molarity of 20-2000 mM. In a preferred embodiment the saline or buffered saline has a pH of 6.0-8.0 and a molarity of 100-500 mM. In a most preferred embodiment the saline or buffered saline has a pH of 7.0-8.0 and a molarity of 120-250 mM. For one embodiment of a kit, the polycistronic miRNAs preferably comprise at least one, or more preferably at least two nucleotides encoded by SEQ ID NO. 1-SEQ ID NO: 5.

VI. Clinical Applications

As mentioned previously, a preferred embodiment of the invention comprises delivery of a vector encoding at least one miRNA or a polycistronic miRNA transcript to a patient in need thereof. Formulation, dosages and treatment schedules have also been described hereinabove. Phase I clinical trials can be designed to assess the safety, tolerability, pharmacokinetics, and pharmacodynamics of the miRNA constructs of the invention. These trials may be conducted in an inpatient clinic, where the subject suffering from an infection can be observed by full-time medical staff. After the initial safety of the therapy has been performed, Phase II trials can assess clinical efficacy of the therapy; as well as to continue Phase I assessments in a larger group of volunteers and patients. Subsequently, Phase III studies on large patient groups entail definitive assessment of the efficacy of the miRNA constructs for treatment of a viral infection in comparison with current treatments. Finally, Phase IV trials involving the post-launch safety surveillance and ongoing technical support for the polycistronic miRNAs can be completed.

The following examples illustrate certain embodiments of the invention. They are not intended to limit the scope of the invention in any way.

EXAMPLE 1

The following materials and methods are provided to facilitate practice of the invention, and are particularly applicable to the instant example.

DNA Constructs

The miR17-92 polycistronic sequence (NCBI GenBank Accession No.: NT_009952.14) was used as a scaffold to construct a gene capable of expressing an artificial pri-miRNA composed of five miRNAs. Secondary structures of the pre-miRNAs as well as the sequence of the mature miRNAs were obtained from the Internet at (mirbase.org). A 783 by DNA fragment was synthesized (GenScript, Piscataway, N.J.) that encoded five anti-HCV miRNA genes embedded in the first five miRNA genes of the endogenous miR17-92 cluster (i.e., miR-17, miR-18, miR-19A, miR-20, miR-19B). The ~11 by lower stems and loops of each endogenous miRNA was maintained, as well as all the intervening sequences and 91 by of 5' flanking and 18 by of 3' flanking DNA sequences. The endogenous sequence was modified slightly by inserting unique restriction sites at the 5' and 3' ends of each miRNA gene to facilitate subcloning. AgeI and BamHI sites flank miR-UTR1, BamHI and ClaI flank miR-UTR2, ClaI and BclII flank miR-UTR3, BclII and EagI flank miR-Core, and EagI and PmeI flank miR-NSSB. The 783 by fragment contained a SphI site upstream of the first miRNA gene and a PmeI site downstream of the last miRNA gene. In addition, XbaI and BamHI sites were included at the 5' and 3' ends, respectively for bidirectional cloning into pUC57 (GenScript, Piscataway, N.J.) to create pUC57-HCV-miR Cluster 1. The plasmid pUC19 was modified to facilitate sub-cloning of the miRNA-containing fragment by inserting a synthetic fragment encoding the restriction sites EcoRI, SphI, PmeI, and HindIII between the EcoRI and HindIII sites of pUC19, creating plasmid pUC19MCSD. The ApoE enhancer and human alpha-one antitrypsin promoter was amplified from plasmid pAAV-hFIX16 by PCR using forward primer 5'-TAGCGAATTCGCTGTTTGTGTGCTGCCT CTGAAG-3' (SEQ ID NO: 11) and reverse primer 5'-TAGCGCATGCACTGT CCCAGG TCAGTGGTG-GTGC-3' (SEQ ID NO: 12), and the amplified product was digested with EcoRI and SphI. The polyadenylation (polyA) fragment was generated by PCR amplification of pAAV-hFIX16 using forward primer 5'-TAGCGTTTAAACCTGT-GCCTTCTAGT TGCCAGCCAT-3' (SEQ ID NO: 13) and reverse primer 5'-TAGCAA GCTTATAGAGCCCACCG-CATCCCCAGCA-3' (SEQ ID NO: 14), and the product was digested with PmeI+HindIII. After enzyme digestion, the ApoE/hAAT promoter fragment, the polyA fragment, and the SphI-PmeI fragment of pUC57-HCV-miR Cluster 1 were cloned into the EcoRI and HindIII sites of pUC19MCSD, to generate pUC19MCSD-ApoE/hAAT-HCV-miRNA Cluster 1. The human growth hormone intron fragment was generated by PCR amplification of pAAV-LacZ (Stratagene, LaJolla, Calif.) using forward primer 5'-TAGCGCATGCTTCGAA CAGGTAAGCGCC-3' (SEQ ID NO: 15) and reverse 5'-TAGCGC ATGCAACCTGGGGAGAAACCAG-3' (SEQ ID NO: 16) and was digested with SphI and cloned into the SphI site of pUC19MCSD-ApoE/hAAT-HCV-miRNA cluster 1, generating pUC19MCSD-ApoE/hAAT-HCV-miRNA Cluster 1+Intron. For construction of HCV-miRNA Cluster 2, a 273 by DNA fragment was synthesized (GenScript, Piscataway, N.J.) that encoded miR-UTR2 and miR-UTR1 embedded in endogenous miR-17 and miR-18 sequences, respectively, and with an AgeI site at the 5'end and a ClaI site at the 3' end. This fragment was initially cloned into pUC57, and then used to replace the AgeI-ClaI fragment of pUC19MCSD-ApoE/hAAT-HCV-miRNA-Cluster 1, creating pUC19MSCD-ApoE/hAAT-HCV-miRNA Cluster 2. For all single miRNA constructs, the individual miRNA fragments were generated by PCR amplification of pUC19-hAAT/ApoE-HCV-miRNA cluster 1 using different primers. All forward primers had an AgeI site at their 5' ends and the reverse primers had a PmeI site at their 5' ends. The individual miRNA fragments replaced the AgeI-PmeI fragment of pUC19MCSD-ApoE/hAAT-HCV-miRNA Cluster 1, generating pUC19MCSD-ApoE/hAAT-HCV-miR-UTR1, pUC19MCSD-ApoE/hAAT-HCV-miR-UTR2, pUC19MCSD-ApoE/hAAT-HCV-miR-UTR3, pUC19MCSD-ApoE/hAAT-HCV-miR-Core, and pUC19MCSD-ApoE/hAAT-HCV-miR-NS5B.

HCV-miR-Cluster 5 was also generated. This construct encodes five miRNAs by using the last miRNA in the miR17-92 cluster (miR-92), rather than the second miRNA (miR-18), as a scaffold for miR-UTR1. Thus, this cluster contains in order: miR-UTR2, miR-UTR3, miR-Core, miR-NS5B, miR-UTR1 and is shown in FIG. 10. For sequence information for AAV vectors comprising Cluster 5, see FIGS. 13A and 13B.

For construction of pscAAV-HCV-miR Cluster 1, the ApoE HCR/hAAT enhancer/promoter was PCR amplified from pAAV-hFIX16 using forward primer: 5' TAG CGC GAT CGC GCT GTT TGT GTG CTG CCT CTG AAG 3' (SEQ ID NO: 28)and reverse primer: 5' TAG CGC ATG CAC TGT CCC AGG TCA GTG GTG GTG C 3', (SEQ ID NO: 29),to generate a fragment flanked by AsiSI and SphI sites. This fragment was co-ligated with the SphI-PmeI fragment of HCV-miR Cluster 1 (containing the 5 miRNAs) into the backbone of pscAAV-FIX100 that had first been digested with AsiSI and PmeI. The salient features of the latter fragment are: a wild-type AAV ITR at the 5' end, the bGH pA sequence, a deleted AAV4 ITR at the 3' end, and an ampicillin resistance marker.

RLuc-HCV reporter plasmids were generated using the psiCheck-2 plasmid (Promega, Madison, Wis.). HCV target sequences (wild-type, seed mutation, and reverse complement) were synthesized as duplex primer pairs (40 bp) (IDT, Coralville, Iowa), and were annealed and ligated between the XhoI and a NotI sites of psiCheck-2, which lie 7-37 nucleotides downstream of the translational stop codon of the RLuc gene. The wild-type reporter primer pairs are as follows: HCV-UTR1 primer pairs: contain HCV1b sequence from 128 to 166 nt, HCV-UTR2 primer pairs: contain HCV1b sequence from 264-304nt, HCV-UTR3 primer pairs: contain HCV1b sequence from 311-349nt, HCV-Core primer pairs: contain HCV1b sequence from 348-387, HCV-NS5B primer pairs contain HCV1b sequence from 7973-8012. The seed mutation reporter plasmids contain a 3 by substitution at positions 4-6 of the guide strand target region. The reverse complement reporter plasmids contain the anti-sense sequence relative to the wild-type reporters. The 5 Target reporter contains the five wild-type 40 by target sequences of the miRNAs arranged in tandem.

Transfection and Luciferase Analysis

The human hepatoma-7 (Huh-7) cell line was maintained in RPMI supplemented with 10% fetal calf serum, 2 mM glutamine and 100 U/ml penicillin/streptomycin. Huh-7 cells were seeded in 24-well tissue culture plates at $4 \times 10^4$ cells/well two days prior to transfection. The cells were co-transfected in triplicate with a miRNA-expressing plasmid (125 ng) or pUC19 (125 ng) and a RLuc-HCV reporter plasmid (125ng). The transfections were performed with Arrest-in (Open Biosystems, Huntsville, Ala.) according to the manufacturer's instructions. Twenty-four hours after transfection, cells were washed with PBS and lysed using Passive Lysis Buffer (Promega, Madison Wis.). Firefly and RLuc activities were assessed using the Dual-luciferase assay system (Promega Madison, Wis.). Luminescence readings were acquired using an automated Veritas luminometer (Turner Biosystems, Sunnyvale, Calif.). Relative light units (RLUs) of RLuc were normalized by dividing by the amount of FFLuc light units. Percent inhibition was calculated by comparing RLUs of the miRNA plasmid-transfected cells to cells transfected with the pUC19 plasmid. Each condition was tested with n=9 independent transfections, unless otherwise specified, and the results are reported as the mean and SD of these values.

Cell Viability Assay

Cell viability was assessed following transfection of Huh-7 cells with plasmids expressing the miRNAs using the AlamarBlue assay system according to manufacturer's instructions (Invitrogen Carlsbad, Calif.) Huh-7 cells were plated in 24 well tissue culture plates at $4 \times 10^4$ cells/well in 500 μl media. Forty eight hours later the cells were transfected using Arrest-In (Open Biosystems, Huntsville, Ala.) according to the manufacturer's instructions with increasing amounts of the HCV miR Cluster 1 plasmid (0, 2.5, 10, 50, or 125 ng) and one of the five RLuc reporters (125 ng) or no reporter. The total amount of plasmid DNA added to cells was adjusted to 250 ng using pUC19. Cells were incubated at 37° C. for 24 hours and then 50 μl AlamarBlue reagent was added directly to the cells and they were incubated at 37° C. for an additional 4 hours. The oxidized form of this dye is converted to the reduced form by mitochondrial enzyme activity in viable cells, and a shift in fluorescence is measured by excitation at 570 nm and emission at 585 nm using a Molecular Devices Spectra Max M2 plate reader (Sunnyvale, Calif.). Percent survival was calculated by comparing the amount of fluorescence emitted from cells transfected with HCV-miR Cluster 1 relative to cells that did not receive this plasmid DNA.

In Vitro HCVcc Inhibition Assays

In Vitro HCVcc Inhibition Assays. HCVcc was produced according to Cai et al., (2005) J. of Virol. 79: 13963-13973 and the physical and infectious titers were determined by quantitative real-time reverse transcription polymerase chain reaction (QRT-PCR) and according to Kato et al., (2006) Nat. Prot. 1: 2334-2339, respectively. For inhibition experiments, Huh-7.5 cells (Apath, Brooklyn, N.Y.) were plated in six-well plates at $2 \times 10^5$ cells/well. Twenty-four hours later, cells were infected with either scAAV2-HCV-miR-Cluster 5 or scAAV2-enhanced green fluorescent protein (eGFP), at one of four multiplicities of infection (MOIs; $1 \times 10^3$, $1 \times 10^4$, $1 \times 10^5$, $1 \times 10^6$ vector genomes [vg]/cell), and HCVcc (~0.2 focus-forming unit [FFU]/cell). The media was replaced two hrs later and the cells were incubated for an additional 72 hours. Supernatants were collected from wells for viral RNA isolation and cells were lysed in TRIzol reagent (Invitrogen, Carlsbad, Calif.) for total cellular RNA purification.

HCV RNA Quantitation.

HCV RNA was quantified by QRT-PCR using in vitro-transcribed JFH-1 (Japanese fulminant hepatitis 1) RNA as a standard.

Animal Procedures

All animal studies were conducted at the Children's Hospital of Philadelphia with approval from the CHOP Institutional Animal Care and Use Committee. Balb/c mice were purchased from Charles River Labs (Wilmington, Mass.). HDTV injections of mice (n=4 or 5) were performed as described elsewhere (41) using 12 μg of a miRNA-expressing plasmid or pUC19 DNA, and 12 μg of a RLuc-HCV fusion plasmid in a total volume of 2.0 ml PBS. Two days later, the animals were sacrificed, livers were harvested and stored at −80° C. until processing.

Biochemical Analysis

Whole mouse livers were ground using a freezer/mill (Spex CertiPrep, Metuchen, N.J.) in liquid nitrogen using three, one minute grinding cycles spaced by three, one minute cooling cycles. Ground livers were stored at −80° C. Lysates of the ground liver were prepared by adding 200 μl of ×Passive Lysis Buffer (Promega, Madison, Wis.) to ~100 mg liver. The activity of Luc in 10 μl lysate was determined using the Dual Luciferase Assay (Promega, Madison, Wis.) on a Veritas luminometer (Turner Biosystems, Sunnyvale, Calif.). Relative light units (RLUs) of RLuc were normalized by dividing by the amount of FFLuc light units. Percent inhibition was calculated by comparing RLUs in the miRNA plasmid-injected mice to animals injected with the pUC19 plasmid. Three independent liver lysates were prepared and analyzed for each liver and the results are reported as the mean and SD of these values.

Northern Blot Analyses.

Ground liver tissue was removed from the −80° C. freezer and ~200 mg was added to 2 ml of TRIzol reagent (Invitrogen, Carlsbad, Calif.), and total RNA was extracted according to the manufacturer's protocol (yield ~0.9 μg RNA/mg ground liver tissue). Twenty five μg of total RNA was resolved on 15% denaturing polyacrylamide TBE-urea gels (Invitrogen, Carlsbad, Calif.) . Decade RNA molecular weight markers (Ambion, Austin, Tex.) were labeled with $\gamma P^{32}$-ATP according to manufacturer's instructions, and were run adjacent to liver RNA samples. RNA was transferred to Bright Star Plus positively charged nylon membranes (Ambion, Austin, Tex.) at 200 mA for 1 hour and UV-crosslinked using the auto-crosslink function on a Stratlinker 1800 (Stratagene, La Jolla, Calif.). Blots were prehybridized using UltraHyb-Oligo buffer (Ambion, Austin, Tex.) for 1 hr at 65° C. and subsequently probed with $\gamma$-$P^{32}$-ATP at room temperature overnight. The blots were washed three times at room temperature and once at 42° C. for 30 min with 6×SSC/0.2% SDS, exposed to film, and developed using a Kodak processor. The DNA oligonucleotide sequences used as probes were as follows: miR-UTR1 guide: 5'-CCATAGTGGTCTGCGGAAC-3' (SEQ ID NO: 17), miR-UTR2 guide: 5'-AAAGGCCT-TGTGGTACTGCCT-3' (SEQ ID NO: 18), miR-UTR3 guide: 5'-AGGTCTCGTAGACCGTGCA-3' (SEQ ID NO: 19), miR-Core guide:5'-AACCTCAAAGAAAAACCAAAC-3' (SEQ ID NO: 20), miR-NSSB guide:5'-GACACTGAGA-CACCAATTGAC-3' (SEQ ID NO: 21), U6 snRNA: 5'-TATGGAACGCTTCACGAATTTGC-3' (SEQ ID NO: 22). The RNA oligonucleotides used as positive controls were as follows: miR UTR1 (guide strand): 5'-GUUCCGCAGAC-CACUAUGG-3' (SEQ ID NO: 23), miR UTR2 (guide strand) 5'-AGGCAGUACCACAAGGCCUUU-3' (SEQ ID NO: 24), miR UTR3 (guide strand) 5'-UGCACGGUCUAC-GAGACCU-3' (SEQ ID NO: 25), miR Core (guide strand) 5'-GUUUGGUUUUUCUUUGAGGUU-3' (SEQ ID NO: 26), miR NS5B (guide strand) 5'-GUCAAUGGUGUCU-CAGUGUC-3' (SEQ ID NO: 27).

Statistical Analysis

Two tailed Student's t tests were performed. P values of 0.05 or 0.01 were used to assess statistical significance.

RESULTS

Construction of Polycistronic Anti-HCV miRNA Vector

To enhance the probability of creating functional miRNAs targeting the HCV genome, the literature was surveyed for siRNAs and shRNAs that had previously been shown to inhibit autonomously replicating full genomic and subgenomic replicons by greater than 80% (7;8). Without being bound by theory, incorporation of these sequences into miRNAs should result in RNAi molecules effective in inhibiting HCV replication. Three of the five siRNAs chosen target the 5'UTR of HCV (UTR1, UTR2, UTR3), and the two others target sequences in one structural (Core) and one non-structural (NS5B) gene. Four of the five targets (UTR1, UTR2, UTR3, and Core) are highly conserved among the six HCV genotypes. The endogenous miR17-92 cluster was utilized to develop a multiplexed platform for inhibiting HCV. This cluster is composed of six genes (36), which are transcribed as a single transcriptional polycistron. The pri-RNA is processed in the nucleus to produce six pre-miRNAs (miR-17, miR-18, miR-19A, miR-20, miR-19B, and miR-92) (FIG. 1), and these are further processed in the cytoplasm to produce seven mature miRNAs. In our first approach, the first five miRNAs of the miR17-92 cluster were replaced with the previously validated anti-HCV siRNAs and shRNAs. siRNA compositions for use in the invention are provided in Tables I and II. The sequences in Table I include several siRNA (i.e., sense sequences for a HCV target region), and Table II provides several sequences of 'anti-sense' strand alone (SEQ ID NOs: 6-10). Those of skill in the art can determine the sequence of an antisense siRNA strand based on the disclosure of the sense strand or target sequence, and will appreciate the difference between "U" and "T" designations in the sequences which correspond to RNA and DNA molecules, respectively. The target sequences, their location in HCV1b, the names of the miRNAs designed to cleave them, and the miRNAs they replace in the endogenous miR-17-92 cluster are shown Table 1.

TABLE 1

| HCV miRNA | HCV Target sequence | Location in HCV 1b | Replaces |
|---|---|---|---|
| miR-UTR1 (SEQ ID NO: 1) | 5'-CCAUAGUGGUCUGCGGAAC-3' | 138-156 | miR-17, miR-18 miR-92 |
| miR-UTR2 (SEQ ID NO: 2) | 5'-AAAGGCCUUGUGGUACUGCCU-3' | 274-294 | miR-17, miR-18, miR-92 |
| miR-UTR3 (SEQ ID NO: 3) | 5'-AGGUCUCGUAGACCGUGCA-3' | 321-339 | miR-19A |
| miR-Core (SEQ ID NO: 4) | 5'-AACCUCAAAGAAAAACCAAAC-3' | 358-378 | miR-20 |

TABLE 1-continued

| HCV miRNA | HCV Target sequence | Location in HCV 1b | Replaces |
|---|---|---|---|
| miR-NS5B (SEQ ID NO: 5) | 5'-GACACUGAGACACCAAUUGAC-3' | 7983-8003 | miR-19B |

Table 1: Names and target sequences for the five anti-HCV miRNAs and their location within the HCV 1b genome. Also shown are the endogenous miRNAs within the miR-17-92 cluster that the anti-HCV miRNAs replace.

Table 2 provides the miRNA sequences (i.e, miRNA) that are incorporated into the pri-miRNAs to inhibit HCV.

TABLE 2

| HCV miRNA | miRNA antisense sequence |
|---|---|
| miR-UTR1 | 5'-GUUCCGCAGACCACUAUGG-3' (SEQ ID NO: 6) |
| miR-UTR2 | 5'-AGGCAGUACCACAAGGCCUUU-3' (SEQ ID NO: 7) |
| miR-UTR3 | 5'-UGCACGGUCUACGAGACCU-3' (SEQ ID NO: 8) |
| miR-Core | 5'-GUUUGGUUUUUCUUUGAGGUU-3' (SEQ ID NO: 9) |
| miR-NS5B | 5'-GUCAAUUGGUGUCUCAGUGUC-3' (SEQ ID NO: 10) |

Table 2: Sequences useful for targeting regions of the HCV genome which can be incorporated into a polycistronic transcript for therapeutic benefit.

A 783 by DNA fragment was synthesized that encoded the five HCV miRNAs embedded in endogenous miR17-19B genomic DNA (FIG. 1; FIG. 8A). The ~11 by lower stems and loops of each endogenous miRNA was maintained, as well as all the intervening sequences and 91 by of 5' flanking and 18 by of 3' flanking DNA sequences. Unique restriction sites were engineered around each of the five miRNAs to facilitate assembly of different miRNA clusters and to create plasmids expressing individual miRNAs. Since the HCV miRNAs are 2-4 nt shorter than the endogenous miRNAs they replaced, it was possible to insert them at the 5' or 3' end of the original miRNA sequence. They were inserted at the 5' end because it has been demonstrated that this orientation results in the generation of more efficient miRNAs (35), and because it is important that the miRNA seed region (2-8 nt from the 5' end) contains HCV antisense sequences rather than endogenous miRNA sequences. The Sfold algorithm (37) was then used to create miRNAs with low internal stability at the 5' ends of the intended mature miRNA (i.e., guide stand). This feature promotes efficient entry of the antisense or guide strand of the mature miRNAs into RISC (4;5). In some cases this involved creating wobble or mismatches by changing the sequence of the sense or passenger strand in the miRNA hairpin structures to manipulate the internal stability of the hairpin. The secondary structure of the endogenous miRNAs were also mimicked by introducing mismatches and bulges into the stem of the HCV miRNAs, as this has been shown to increase the probability that the guide strand will be incorporated into the RISC (34). Unlike the endogenous miRNAs, the anti-HCV miRNAs were designed to be entirely complementary to their targets, and thus are predicted to mediate site-specific cleavage of their cognate targets.

In order to minimize any potential off-target effects by ectopic expression of miRNAs, the synthesized DNA fragment was subcloned into a vector downstream of a liver-specific enhancer/promoter, the ApoE hepatic control region and the alpha-one antitrypsin promoter. This regulatory element has been previously used to drive high level liver-specific expression of coagulation factor IX in rodents, dogs, non-human primates, and humans (38). The bovine growth hormone polyadenylation sequence was inserted downstream of the miRNA cluster, and some constructs contained an intron, which was cloned just upstream of the miRNA sequences.

Figure 3:
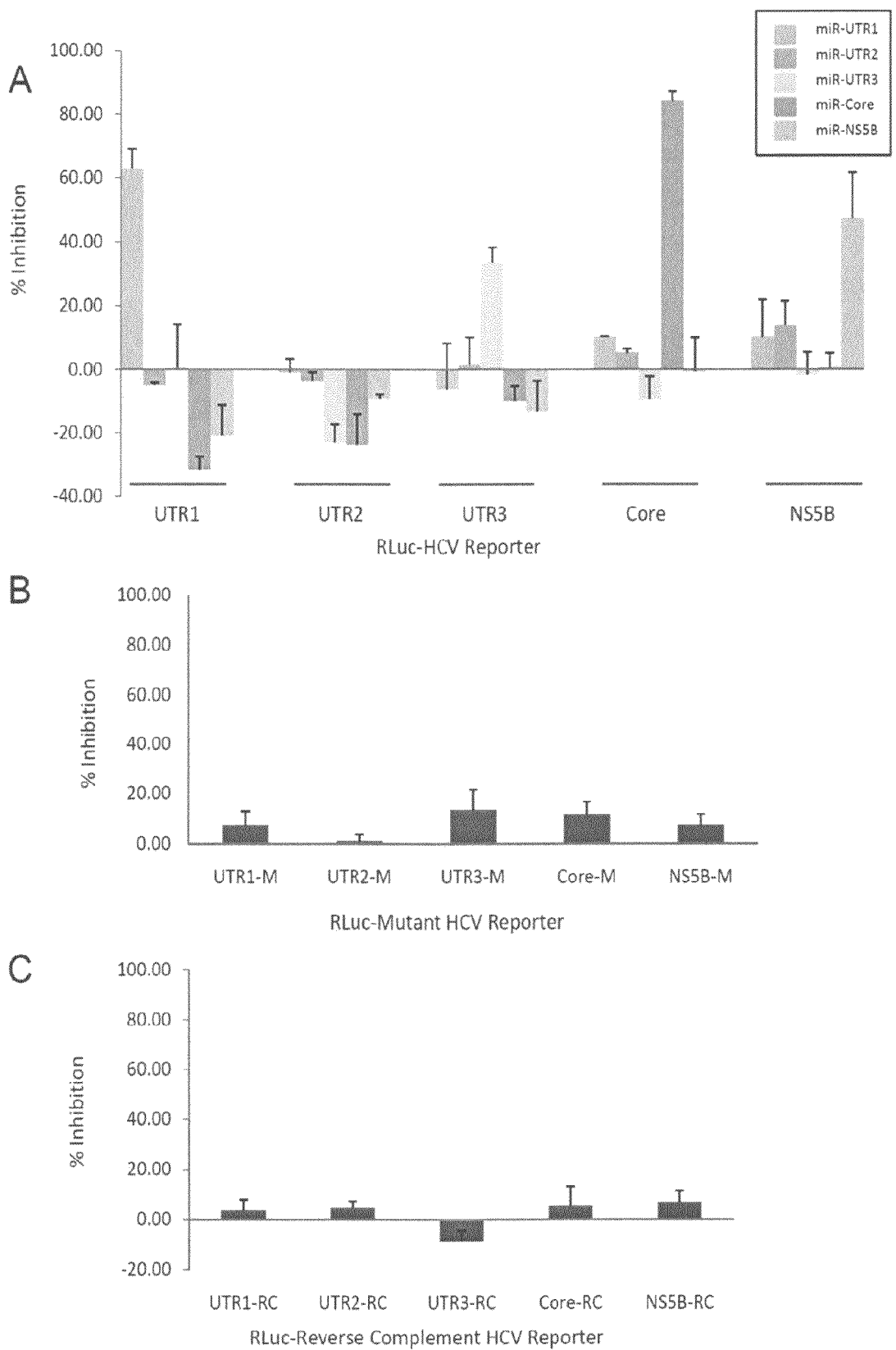
FIG. 3: Specificity of miRNAs targeting HCV. Huh-7 cells were co-transfected with a RLuc-HCV reporter plasmid (125 ng) and a plasmid expressing a single anti-HCV miRNA (125ng), HCV-miR Cluster 1 (125 ng), or pUC19 (125ng). Twenty four hours post-transfection, cell lysates were prepared and dual luciferase (FFLuc and RLuc) assays were performed. Normalized RLuc expression the presence of pUC19 was set as 100% activity or 0% inhibition of the target, and the % inhibition achieved by each miRNA was compared to the pUC19 control. Mean values from triplicate replicates of at least 3 independent experiments are shown (+SD). (A) Inhibitory activity of single anti-HCV miRNAs against WT reporter plasmids (UTR1, UTR2, UTR3, Core, NSSB). (B) Inhibitory activity of HCV-miR Cluster 1 against RLuc-HCV reporters that contained 3 by mutations in the miRNA target sequences (UTR1-M, UTR2-M, UTR3-M, Core-M, NSSB-M). (C) Inhibitory activity of HCV-miR Cluster 1 against RLuc-HCV reporters that contained the reverse complement of the miRNA target sequences (UTR1-RC, UTR2-RC, UTR3-RC, Core-RC, NSSB-RC).

Four HCV miRNA clusters were constructed. Cluster 1 contains in order: miR-UTR1, miR-UTR2, miR-UTR3, miR-Core, and miR-NSSB (with or without an intron), and Cluster 2 contains in order: miR-UTR2, miR-UTR1, miR-UTR3, miR-Core, and miR-NS5B (FIG. 1; FIGS. 8A and 8B). Cluster 5 contains in order, miR-UTR-2, miR-UTR-3, miR-Core, miR-NS5B and miR-UTR-1. In cluster 5, miR-18 is deleted. In addition, plasmids expressing the individual miRNAs were constructed by removing four out of five miRNAs from Cluster 1. It should be noted that other miRNA sequences targeting different sequences within the HCV genome can be used in accordance with the teachings herein. See FIG. 9. The full length sequence of HCV is known as are the sequences encoding each of the structural and functional proteins of the virus. Accordingly, other regions of the genome may be targeted and clusters designed to incorporate this sequence information. Varying the regions targeted by the cluster is particularly desirable in certain situations, particularly to treat escape mutants that may emerge following administration of the constructs described herein.

In Vitro Activity of Anti-HCV miRNAs

A series of renilla luciferase (RLuc)-HCV reporter plasmids were constructed by fusing HCV target sequences downstream of the RLuc gene in plasmid psiCHECK. These were used to evaluate the ability of the miRNAs to cleave their target sequences. In addition, a reporter plasmid that contained all five HCV target sequences was constructed. Each plasmid also contained a firefly luciferase (FFLuc) gene to normalize for transfection efficiency. To evaluate the individually expressed miRNAs, Huh-7 cells were co-transfected with an RLuc-HCV reporter plasmid and a miRNA-expressing plasmid, and were compared to cells that were co-transfected with the same reporter plasmid and pUC19. Twenty four hours later, dual luciferase assays were performed on cell lysates. Normalized RLuc expression (RLuc/FFLuc) in the presence of pUC19 was set as 100% activity or 0% inhibition of the reporter plasmid. The normalized RLuc activity in cells transfected with the miRNA-expressing plasmid was then divided by the activity measured in the cells transfected with pUC19 to obtain the % inhibition of the target. FIG. 2A demonstrates that four out of five of the miRNAs were able to inhibit their cognate HCV sequence when they were expressed individually. Expression of miR-UTR1 inhibited its target by 63+/−6%, miR-UTR3 by 34+/−4.7%, miR-core by 84+/−3.1%, and miR-NS5B by 47+/−14% ($P<0.01$ for these four miRNAs). However, expression of miR-UTR2 resulted in no silencing of its cognate target. Similar results were observed when a reporter encoding all five targets was used. Specifically, miR-UTR1, miR-UTR3, miR-Core, and miR-NS5B silenced this reporter by 71+/−2%, 49.8+/−7.4%, 77.6+/−0.7%, and 57+/−2% ($P<0.01$ for these four miRNAs), respectively, while miR-UTR2 had low level activity (27+/−5.6%; $P<0.01$), indicating the potential for non-specific activity by the miRNA that showed no activity against its cognate target (FIG. 2A).

A plasmid expressing the HCV miR Cluster 1, which encodes in order, miR UTR-1, miR-UTR2, miR UTR-3, miR-Core, and miR-NS5B was simultaneously evaluated. When this Cluster was evaluated for silencing of the individual RLuc reporters, a 61+/−5%, 1+/−9%, 64+/−13%, 68+/−7%, and 68 +/−9% inhibition of the corresponding targets was observed, respectively (FIG. 2B). Four of five of these values were statistically significant relative to their controls ($P<0.01$). In addition, 79+/−5% ($P<0.01$) inhibition of the reporter containing all five targets was observed. These results demonstrate that expression of miRNAs as part of a polycistronic mRNA does not negatively affect their activity, and in some cases improves their efficacy. For example, expression of miR-UTR3 and miR-NS5B from Cluster 1 resulted in statistically more inhibition of their cognate targets compared to expression of these miRNAs alone. This observation is significant because others have shown that competition exists between shRNAs when they are simultaneously expressed from a single vector (30). This competition is not observed using the constructs described herein.

In order to determine whether incorporation of an intron in the primary miRNA transcript would improve the efficacy of the miRNA cluster, a 278 by intron was inserted downstream of the promoter and upstream of the miRNA cluster. As shown in FIG. 2B, similar levels of inhibition were observed using this construct, including the lack of activity by miR-UTR2.

In HCV miR Cluster 1, mir-UTR2 was inserted into endogenous miR-18. Interestingly, the incorporation of a miRNA targeting the polymerase region of HIV was also inactive when it replaced endogenous miR-18 (35). It was suggested that because the hairpin structure of the endogenous miRNA is relatively unstable, misfolding of the hairpin RNA may result, negatively impacting its function. Since the predicted mature miR-UTR2 should have the same sequence as a siRNA that has previously been demonstrated to inhibit an HCV replicon, one explanation was that the mature miRNA was not properly processed from the pri-miRNA or pre-miRNA. By moving it to another position in the miRNA cluster, it may be possible to rescue its activity. Therefore, a second cluster (HCV Cluster 2) was constructed which contained the same five miRNAs but in a different order: miR-UTR2, miR-UTR1, miR-UTR3, miR-Core, and miR-NSSB. Thus, in this cluster miR-UTR2 replaces endogenous miR-17, and miR-UTR1 replaces endogenous miR-18. In this orientation, miR-UTR2 was active and was able to inhibit its target by 72+/−0.5% (FIG. 2C). In contrast, this change resulted in a loss of activity for miR-UTR1. The other three miRNAs maintained their activity with miR-UTR3 demonstrating 44.5+/−9 inhibition, miR-Core demonstrating 62+/−2% silencing, and NSSB showing 56+/−11% inhibition. There was no significant difference between expression of miR-UTR3, miR-Core, and miR-NSSB when expressed from Cluster 1 or Cluster 2. These results indicate that mature miRNAs are not processed correctly from the miR-18 scaffold. When they are inserted into another endogenous miRNA, they can be processed to their mature forms and their activity can be restored. The new cluster, Cluster 2, was also able to silence a reporter that contains all five miRNA targets by ~80+/−2% ($P<0.01$).

Safety Evaluation of Anti-HCV miRNAs

Off-targeting, or the inappropriate cleavage of unintentional targets, represents a potentially serious risk for RNAi-based agents. It is triggered by downregulation of targets when pairing between the seed region (positions ~2-8 nt from the 5' end of the miRNA) of the miRNA guide strand and complementary sequences in the 3' UTR of off-targeted transcripts occurs (39).

The relative sequence specificity of the individually expressed miRNAs for their targets was evaluated by determining their ability to inhibit non-cognate reporter plasmids. As shown in FIG. 3A, miR-UTR1 inhibited its cognate target, but did not inhibit the RLuc-UTR2 or RLuc-UTR3 reporters, and only low levels of inhibition (<10%) were observed against the RLuc-Core and RLuc-NSSB reporters. As shown above, miR-UTR2 was unable to inhibit its cognate reporter and the data in FIG. 3A indicate that it was also ineffective against non-target reporters, with the exception of the NSSB reporter where 14+/−7.6% inhibition was observed. Again, this indicates that this miRNA may induce low levels of non-specific silencing. The miR-UTR3, miR-Core, and NSSB miRNAs were only able to inhibit their cognate reporters, and no inhibition of non-specific reporters was detected. Thus, the four active miRNAs show good specificity in inhibiting the target sequences that they were designed to silence.

Figure 2:
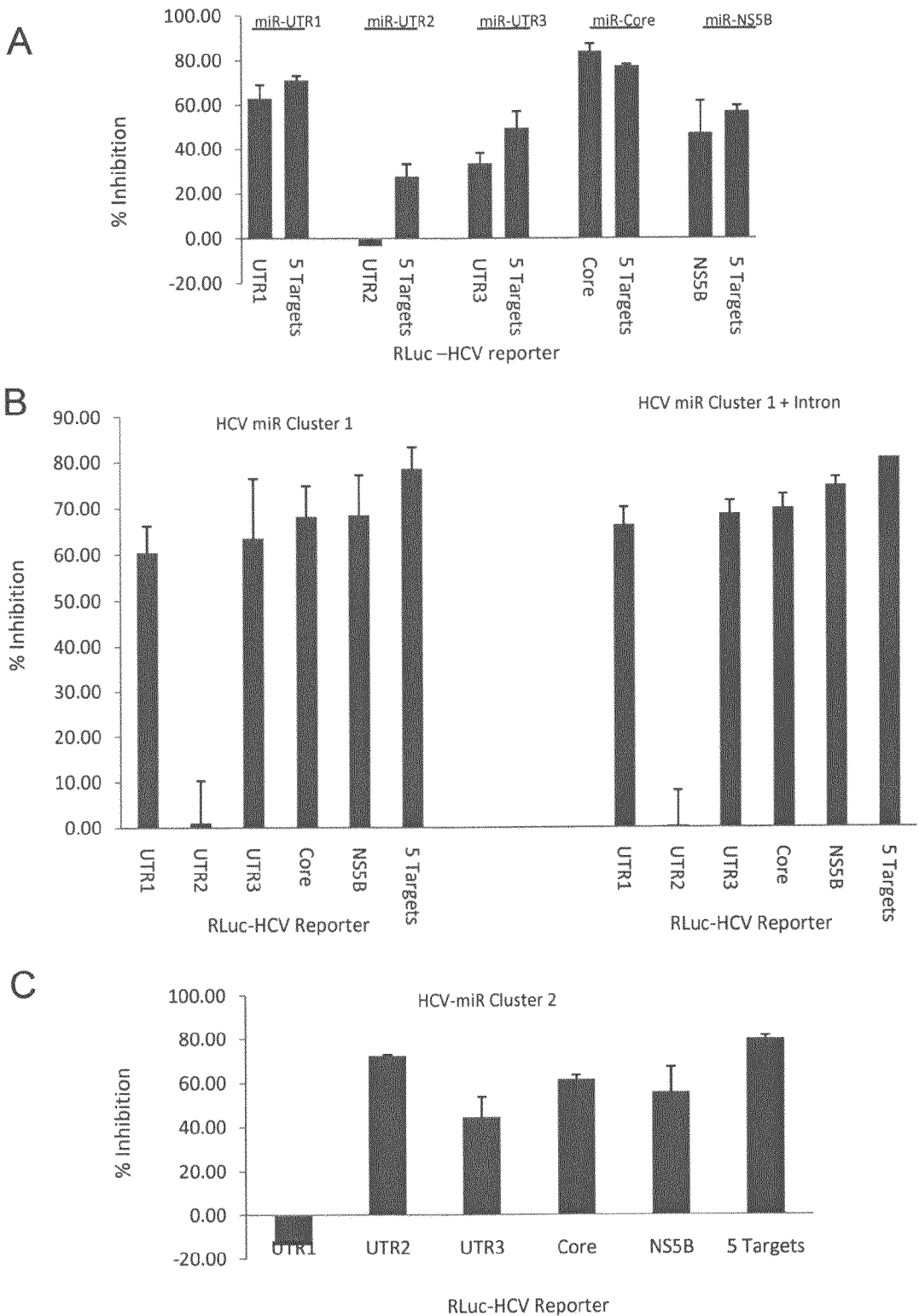
FIG. 2: In vitro inhibition of luciferase reporters by miRNAs targeting HCV. Huh-7 cells were co-transfected with a RLuc-HCV reporter plasmid (125 ng) and a plasmid expressing one of five anti-HCV miRNAs (125 ng), a plasmid expressing all five anti-HCV miRNAs (125 ng), or pUC19 (125 ng). RLuc reporter plasmids encoded either an individual HCV target (UTR1, UTR2, UTR3, Core, NSSB) or all 5 HCV target sequences (5 Targets). Twenty four hours post-transfection, cell lysates were prepared and dual luciferase (FFLuc and RLuc) assays were performed. Normalized RLuc expression in cells transfected with pUC19 was set as 100% activity or 0% inhibition of the target, and the percent inhibition achieved by each miRNA was compared to the pUC19 control. Mean values of triplicate samples from at least 3 independent experiments (unless stated otherwise) are shown (+/−SD). (A) Inhibitory activity of individually expressed anti-HCV miRNAs (miR-UTR1, miR-UTR2, MiR-UTR3, miR-Core, miR-NSSB) against individual reporters or the reporter encoding all 5 targets. (B) Inhibitory activity of anti-HCV miRNAs when expressed from HCV-miR Cluster 1 or HCV-miR-Cluster 1 +Intron against individual cognate targets or the reporter encoding all 5 targets. (C) Inhibitory activity of anti-HCV miRNAs when expressed from HCV-miR Cluster 2 against individual cognate targets or the reporter encoding all 5 targets (data is from triplicate replicates of 2 independent experiments).

Additional evaluation of the sequence specificity of miRNAs was assessed using RLuc-HCV reporter plasmids that contained three by mutations in the area corresponding to the seed region of the miRNA. In these experiments, the HCV-miRNA Cluster 1 plasmid was used. As shown in FIG. 3B, co-transfection of this plasmid with the RLuc-UTR1 mutant reporter resulted in 7+/−6% inhibition. When it was co-transfected with the UTR2, UTR3, Core, and NS5B mutant RLuc reporters, 1+/−2%, 13+/−9%, 12+/−5%, and 7+/−5% inhibition of the target was observed. This is in contrast to the 60-80% inhibition of wild-type reporters observed in FIG. 2B, demonstrating that the HCV miRNAs have good specificity for the wild-type HCV genome, minimizing the potential for off-target effects.

Another potential concern with the generation of artificial miRNAs is that the wrong strand of the miRNA duplex will be incorporated into the RISC, resulting in passenger strand-mediated off-target effects. Strand selection by the RISC is governed by strand asymmetry (4;5) with the 5' end of the guide strand having lower base-pairing stability than the passenger strand. This results in preferential assembly of the guide strand into the RISC, which is accompanied by destruction of the passenger strand. It has been shown that in order to obtain good discrimination between strands in the RISC incorporation, it is important to mimic the secondary structure of the endogenous miRNA closely (34). Close attention was paid to this in the design of the pre-miRNAs by introducing mutations in the passenger strand to create bulges, while retaining the guide strand sequence. To evaluate how successful the design of the HCV miRNAs was in ensuring guide strand assembly into the RISC, five RLuc-HCV reporter plasmids that contained the reverse complement HCV target sequences were generated. Inhibition of RLuc activity would represent incorporation of the passenger strand into the RISC and would be a concern for passenger strand-mediated off-target effects and low potency of miRNAs. As evidenced by FIG. 3C, very low levels of inhibition of the reverse complement targets was observed (ranging from 0-7%). These data, coupled with the data from FIG. 2B using the wild type RLuc reporters, demonstrate that the proper strand (i.e. guide) of the miRNAs was loaded into the RISC.

Figure 4:
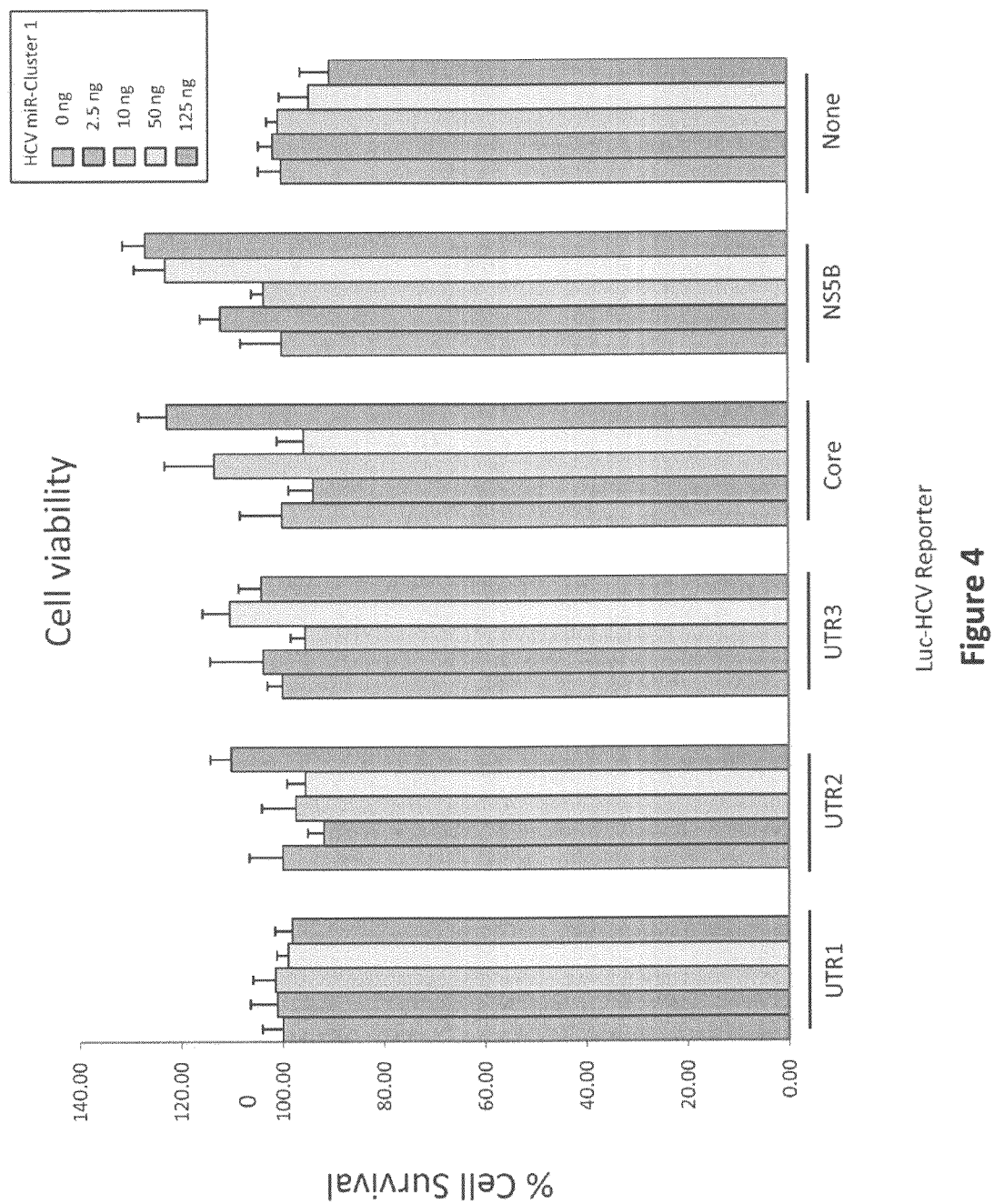
FIG. 4: Cell viability. Huh-7 cells were co-transfected with increasing amounts of the HCV-miR Cluster 1 plasmid (0, 2.5, 10, 50, 125 ng) in the presence or absence of one of the RLuc-HCV reporter plasmids. The total amount of plasmid DNA added to cells was adjusted to 250 ng using pUC19. Twenty four hours post-transfection, 50 µl of AlamarBlue reagent (Invitrogen Carlsbad, Calif.) was added directly to the cells and the cells were incubated at 37° C. for 4 hours, and fluorescence was measured according to the manufacturer's instructions. Percent survival was calculated relative to cells not transfected with HCV-miR Cluster 1 plasmid DNA. Mean values from triplicate measurements of two independent experiments are shown (+SD).
Figure 6:
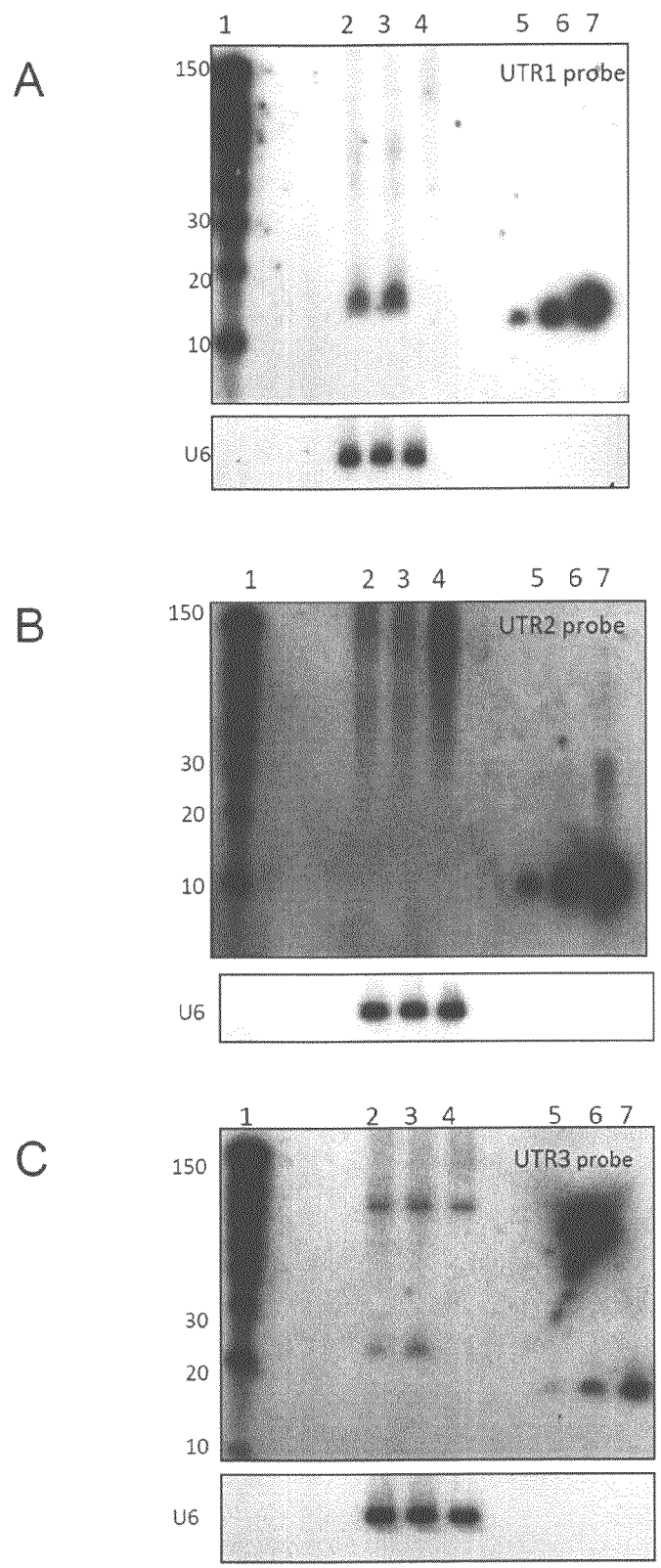
FIG. 6: Northern blot analyses of miRNA transcripts in murine liver RNA. (A-E)

Further evaluation of off-targeting was evaluated by determining proliferation of Huh-7 cells after transfection of miRNA expressing plasmids. Fedorov et al. (40) demonstrated that off-target effects induced by siRNAs can be manifested as strong quantifiable phenotypes, such as an inhibition of cell growth. To evaluate the potential toxic effect of the HCV miRNAs, Huh-7 cells were transfected with increasing amounts of HCV miR Cluster 1 and one of the five RLuc reporters or no reporter. Twenty-four hours later, cell proliferation was analyzed. FIG. 4 demonstrates that in the presence of a reporter plasmid, expression of miRNAs from HCV miRNA Cluster 1 does not affect cell proliferation. In addition, in the absence of a reporter plasmid, a situation which might enhance off-target effects, no effect on cell viability was seen. The combined data demonstrate that the HCV miRNAs are specific for their targets, incorporate the proper strand into the RISC, and do not affect cell viability. Thus, expression of these miRNAs from a polycistronic transcript appears to be safe in vitro and the likelihood of off-target effects is minimal.

In Vivo Activity of Anti-HCV miRNAs

The efficacy of an artificial polycistronic miRNA has not been previously evaluated in vivo. The efficacy of the five HCV miRNAs was evaluated in mouse liver by co-injecting the HCV miRNA plasmids (Cluster 1, Cluster 1+Intron, and Cluster 2) with the RLuc-HCV reporter plasmids via hydrodynamic tail vein injection (41). Two days following the injection, mice were sacrificed, livers were harvested, and dual luciferase assays were performed on liver lysates. The efficacy of miR-UTR1 to target its reporter when expressed from miR Cluster 1 with and without an intron was compared, and similar levels of inhibition (~90%), with no statistical difference, were observed. Subsequently, miR Cluster 1+Intron was chosen for all analyses. As shown in FIG. 5A , four of the five miRNAs expressed from HCV Cluster 1+ Intron were highly active in inhibiting their cognate reporters. For example, miR-UTR1 inhibited its reporter by 89+/−1.4%, and miR-UTR3, miR-Core, and miR-NSSb silenced their cognate RLuc reporters by 65.5+/10.5%, 95%+/3.5%, and 93+/−1.7%, respectively (P<0.01 for these four miRNAs). Similar to what was found in Huh-7 cells, miR-UTR2 was completely inactive. HCV-miR Cluster 1+Intron was also evaluated against the RLuc reporter containing all five HCV targets and saw 94+/−2% (P<0.01) inhibition of this target. In all cases, higher silencing activity by the four active miRNAs was observed in vivo as compared to that seen in vitro. The higher activity was not due to non-specific silencing as demonstrated by the failure of HCV-miR Cluster 1 +Intron to inhibit a reporter lacking HCV sequences (psiCHECK) (FIG. 5A). In addition, the lack of inhibition of the RLuc-HCV UTR1 reporter by HCV-miR-Core alone, also demonstrated that the higher levels of inhibition observed in vivo are not due to non-specific targeting.

As mentioned above, a second miRNA cluster (HCV-miR Cluster 2) was constructed to evaluate the activity of miR-UTR2 when inserted into endogenous miR-17, rather than miR-18. This change in position resulted in a highly active miR-UTR2, capable of inhibiting it's target by 97+/−0.5% (P<0.01) (FIG. 5B). As was the case in vitro, the reciprocal placement of miR-UTR1 into endogenous miR-18 from miR-17, completely abolished its activity, again suggesting that mature miRNAs are not processed correctly from a pre-miR-18 scaffold. The three other miRNAs (UTR3, Core, NSSB) were able to inhibit their targets by 79+/−4.3%, 97+/−0.9%, and 92+/−1.4% (P<0.01 for these three miRNAs), respectively. Similar to Cluster 1, Cluster 2 was also able to silence the HCV reporter containing all five targets by 92+/−2.7% (P<0.01) (FIG. 5B). Thus, two separate HCV-miR Clusters are able to express four potent miRNAs that target HCV sequences.

Active miRNAs Are Properly Processed From Pri-RNAs

The data hereinabove indicate that four out of five miRNAs expressed from HCV miR Cluster 1 and 2 are properly processed from the pri-miRNA and that their guide strands are selectively incorporated into the RISC, where they mediate inhibition of their cognate HCV targets. To confirm this, Northern blot analyses of total RNA from the livers of mice that had been injected with HCV-miR Cluster 1 and HCV-miR Cluster 1+Intron was performed. Using sense strand RNA probes to detect the guide strand, mature forms of the four active miRNAs were observed (FIG. 6A, 6C-6E). Very little pre-miRNA, which is expected to range from 70-87 nucleotides, was observed, indicating that efficient processing of miR-UTR1, miR-UTR3, miR-Core and miR-NSSB from the pre-miRNA was achieved. Synthetic siRNA standards were included on the blots to estimate the amount of each miRNA that was produced. Approximately equal amounts (~1 fmole) of the four active miRNAs are present in 25 µg of liver RNA. This indicates that these four miRNAs are processed from the pri-miRNA with similar efficiencies. In contrast, no mature miR-UTR2 was observed following transfection of mouse liver with HCV-miR Cluster 1 or HCV-miR Cluster 1+Intron (FIG. 6B), consistent with the lack of inhibition of the RLuc-HCV UTR2 reporter plasmid, that was observed in the dual luciferase assays. Overexposure of this blot failed to detect the miR-UTR2 transcript.

When the orientation of miR-UTR1 and miR-UTR2 were reversed in HCV-miR Cluster 2, a highly active miR-UTR2 was produced, while miR-UTR1 was inactive, as measured by RLuc activity. This correlated with the production of mature miRNAs as Northern blot analyses demonstrated that RNA isolated from mice injected with HCV-miR Cluster 2 contained mature miR-UTR2 and very little pre-miRNA (FIG. 7B). As was predicted by the silencing data, no mature miR-UTR1 was produced from HCV miRNA Cluster 2 (FIG. 7A). These data indicate that miRNAs are not efficiently processed from the miR-18 scaffold and that the use of this scaffold for the generation of artificial miRNAs requires further optimization. However, the other four miRNA scaffolds can be used successfully to produce highly active miRNAs.

A Northern blot was also probed with the miR-UTR3 antisense strand probe to assess the amount of passenger strand present in the liver. Consistent with what was found using the reverse complement RLuc HCV reporter, no evidence of the passenger strand was detected, supporting the idea that the guide strand of the mature miR-UTR3 is stable and active, while passenger strand is degraded.

Given the problems with expressing an HCV inhibitory RNA from the miR-18 loop, we generated another HCV-miRNA cluster (HCV-miR-Cluster 5) that encodes five miRNAs by using the last miRNA in the miR17-92 cluster (miR-92), rather than the second miRNA (miR-18), as a scaffold for miR-UTR1. Thus, this cluster contains in order: miR-UTR2, miR-UTR3, miR-Core, miR-NSSB, miR-UTR1 (FIG. 10).

The plasmid encoding HCV-miRNA-Cluster 5 was evaluated for the ability to silence six different RLuc-HCV reporter plasmids in Huh-7 cells. Huh-7 cells were co-transfected with 125 µg of an RLuc-HCV reporter plasmid (UTR1, UTR2, UTR3, Core, NSSB, or 5 Targets) and 125 µg of a plasmid expressing HCV-miR-Cluster 5, or pUC19. Twenty four hours post-transfection, cell lysates were prepared and dual luciferase (Firefly Luc and Renilla Luc) assays were performed. Normalized RLuc expression in cells co-transfected with pUC19 was set as 100% activity or 0% inhibition of the target, and the percent inhibition achieved by each miRNA was compared to the pUC19 control. In contrast to the previous clusters, all five anti-HCV miRNAs were active and inhibited their cognate targets by up to 73% and inhibited expression from the 5 Target reporter by 87% (FIG. 11).

To evaluate the inhibitory potential of scAAV2-HCV-miRNA-Cluster 5 on HCVcc replication, Huh7-5 cells were plated at $2 \times 10^5$ cells per well in a 6 well plate. Twenty-four hours later, cells were infected with HCVcc and either scAAV2-HCV-miRNA-Cluster 5 or the control vector, scAAV2-eGFP, at one of four MOIs ($1 \times 10^3$, $1 \times 10^4$, $1 \times 10^5$, $1 \times 10^6$ vg/cell). Media was changed after 2 hrs and the cells were incubated for 72 hrs, at which time cell supernatants and cell lysates were harvested. Viral RNA and total cellular RNA was purified from supernatants and cell lysates, respectively. Two independent experiments were performed, and average % inhibition is shown. A negative control included wells of Huh 7.5 cells that were not transduced by AAV vectors, but were treated with HCVcc. As shown in FIG. 12A, the amount of HCV sequences observed in the total cellular RNA, as determined by quantitative real-time RT-PCR (QRT-PCR), decreased in a dose-dependent manner. Using $10^3$, $10^4$, $10^5$, and $10^6$ vg/cell of scAAV2-HCV-miR-Cluster 5, 25, 45, 91, and 93% inhibition of HCVcc was achieved, respectively. The decrease in cellular HCV RNA levels correlated with a decrease in the levels of HCV RNA observed in the supernatants (FIG. 12B). These data demonstrate that that scAAV2-HCV-miR-Cluster 5 has the ability to inhibit bona fide HCV replication by up to 96%.

AAV Vectors Expressing HCV-miRNA-Cluster 5 Eliminate HCVcc From Infected Cells

Previously, we demonstrated that scAAV2-HCV-miRNA-Cluster 5 was able to inhibit HCVcc replication by up to 96% when added to Huh7.5 cells at the time of HCVcc infection. We now show that the Cluster 5 vector can completely eliminate an HCVcc infection. In order to model how the AAV-Cluster 5 vector would perform in an in vivo setting, where hepatocytes do not divide and the vector is stably maintained, Huh7.5 cells were first infected with both HCVcc and scAAV2-HCV-miRNA-Cluster 5. Forty eight hours later, a portion of the supernatant was transferred to Huh7.5 cells that had previously been transduced with scAAV2-HCV-miRNA-Cluster 5. Another portion of the supernatant, as well as the cells, was analyzed for HCVcc copies by quantitative RT-PCR. This process was repeated for a total of six rounds. Another set of cells was first infected with HCVcc and an AAV vector that expresses just a single miRNA (i.e., miR-Core). Controls in this experiment included cells that were infected with HCVcc and transduced with AAV-GFP, cells that were infected with HCVcc and treated with IFN-α, HCVcc only-infected cells, and cells that were not treated with either HCVcc or AAV. The data in FIG. 14 demonstrate that by the fourth round of HCVcc propagation in AAV-Cluster 5-transduced cells, HCVcc was eliminated from the culture (blue bars). This represents at least a 5 log decrease in HCVcc levels (assay limit of quantitation (LOQ)=100 copies). In contrast, HCVcc was not eliminated from un-treated cells (red bars) or cells transduced with AAV-GFP (green bars). Although a 96% decrease in HCVcc levels were observed in cells repeatedly transduced with AAV-miR-Core, HCVcc was not eliminated from the culture (purple bars). IFN-α was also able to clear the HCV infection over time (orange bars). These data suggest that in an infected liver, the stable expression of miRNAs from scAAV2-HCV-miRNA-Cluster 5 will result in the elimination of HCV from transduced hepatocytes.

scAAV8-HCV-miRNA-Cluster 5 Silences All 5 Target Sequences In Vivo

We have previously shown that plasmid DNA encoding HCV-miRNA-Cluster 5 was capable of silencing the five cognate miRNA target sequences. We have now cloned this expression cassette into an AAV vector backbone and packaged it into scAAV8 vector particles for efficient gene transfer to the liver. The scAAV8-HCV-miRNA-Cluster 5 vector was evaluated for its ability to express the five anti-HCV miRNAs and to silence their cognate HCV target sequences in vivo.

Mice were injected with one of three doses of the vector ($2.5\times10^9$, $2.5\times10^{10}$, and $2.5\times10^{11}$ vector genomes/mouse; n=5). In addition, a cohort of animals was injected with $2.5\times10^{11}$ vector genomes of the control vector, scAAV8-GFP. Two weeks later, one of five Renilla luciferase /HCV reporter plasmids was injected. Animals were sacrificed two days later and liver lysates were analyzed for dual luciferase activity. The percent inhibition of the targets was determined relative to the scAAV8-GFP-treated control animals. The data in FIG. 15 demonstrates that at the low vector dose, gene silencing of the UTR1 and UTR2 target sequences was observed, but no silencing of the other three targets was seen. However, at the middle dose, all five HCV target sequences were inhibited by 54-93%, and at the high vector dose, silencing of up to 98% was observed. Northern blot data (not shown) confirmed a dose response in the expression of the miRNAs, with no or low expression of the miRNAs seen at the low dose, and clearly detectable miRNAs observed at the two higher doses.

scAAV8-HCV-miRNA-Cluster 5 Can Be Safely Delivered to the Liver

A study was performed to evaluate potential hepatotoxicity following administration of scAAV8-HCV-miRNA-Cluster 5 to mouse liver. It has been reported that the administration of AAV-vectors expressing short hairpin RNAs results in toxicity and lethality at high doses, whereas delivery of miRNA mimics has been reported to be safe. Thus, to evaluate this novel AAV vector, mice were injected with three different doses of scAAV8-HCV-miRNA-Cluster 5 ($2.5\times10^9$, $2.5\times10^{10}$, and $2.5\times10^{11}$ vector genomes/mouse; n=5), and serum was collected at 4-5 different time points for liver enzyme analyses. As shown in FIG. 16, no differences in the levels of the two major indicators of hepatotoxicity, alanine amino transferase (ALT) and alkaline phosphatase (AP), were observed between the negative control cohort (scAAV8-GFP) and the three scAAV8-HCV-miRNA-Cluster 5 -treated animal cohorts, indicating that the miRNA-expressing vector can be safely delivered to mouse liver. Further studies demonstrate that no elevations or decreases in aspartate aminotransferase (AST) or albumin and were observed at any time point following administration of scAAV8-HCV-miR-Cluster 5. The same was true for the four other serum proteins monitored (gamma-glutamyl transferase, bilirubin, total protein, creatine phosphokinase; data not shown). In addition, no elevations of any serum proteins were observed following administration of similar doses of the ssAAV8-HCV-miR-Cluster 5 vector (discussed below).

To investigate the mechanism by which in vivo gene silencing occurs, the fate of one of the reporter plasmid transcripts (RLuc-HCV-Core mRNA) was evaluated by Northern blot. Because the miRNAs were designed to be completely complementary to their HCV target sequences, it is predicted that the RLuc-HCV-Core mRNA expressed from the reporter plasmid will be cleaved, rather than translationally repressed. In order to evaluate this, total cellular liver RNA from mice injected with increasing doses of scAAV8-HCV-miR-Cluster 5 and the RLuc-HCV-Core reporter plasmid was analyzed by Northern blot for the presence of the RLuc-HCV-Core mRNA transcript. As seen in FIG. 17, as the dose of AAV increased, the level of this transcript decreased and became undetectable, consistent with an RNAi mechanism (mRNA cleavage or destabilization), rather than a non-specific gene silencing mechanism, such as innate immune response induction.

Self-complementary AAV-miR-Cluster 5 and Single-Stranded AAV-miR-Cluster 5 Vectors Induce Similar Levels of Gene Silencing The initial in vivo studies were performed using scAAV vectors because they have been reported to transduce mouse liver approximately 10 times more efficiently than traditional single-stranded (ss) AAV vectors. In our hands, scAAV vectors are more challenging to produce, as they result in lower yields and contain more impurities (unpublished data). Therefore, ssAAV vectors are preferable for clinical development, if they are equally effective as scAAV vectors. To directly compare these two types of vectors, the identical HCV-miR-Cluster 5 expression cassette was inserted into either scAAV or ssAAV backbone plasmids and vectors were produced. Since the physical titer of scAAV vectors is often underestimated using QPCR, three additional methods were employed: quantitative PAGE/silver stain, optical density, and quantitative alkaline agarose gel electrophoresis followed by Southern blot hybridization (FIG. 18a). Based on the results of the four assays, the 95% confidence intervals for the doses of scAAV8-HCV-miR-Cluster 5 and ssAAV8-HCV-miR-Cluster 5 used in this study were $4.4+/-2.4\times10^{10}$ vg/mouse and $2.7\times10^{10}+/-9.1\times10^9$ vg/mouse, respectively. Control mice were injected with scAAV-eGFP ($2.5\times10^{10}$). Two weeks following vector administration, either the RLuc-Core or RLuc-NSSB reporter plasmid was injected into the mice via HDTV. Livers were harvested two days later for analysis of dual luciferase activity. As shown in FIG. 18b, the scAAV8-HCV-miR-Cluster 5 and ssAAV8-HCV-miR-Cluster 5 vectors inhibited the expression of the RLuc-Core reporter plasmid by 82% and 80% respectively, relative to the control mice, and inhibited the RLuc-NSSB reporter plasmid by 72% and 63%, respectively. No statistically significant differences in gene silencing activity were observed between the two types of vectors. In addition, the levels of miR-Core in mouse liver, as determined by QRT-PCR, were similar (FIG. 18c). An additional study was performed to determine the level of gene silencing of the other three RLuc-HCV reporter plasmids (RLuc-UTR1, RLuc-UTR2, RLuc-UTR3) by the ssAAV8-HCV-miR-Cluster 5 vector (FIG. 18d). The data in FIG. 18b-d indicate that the ssAAV8-HCV-miR-Cluster 5 vector and the scAAV8-HCV-miR-Cluster 5 vector have similar potencies. The cumulative data demonstrate that, at least for this expression cassette, the self-complementary configuration of AAV does not provide any advantage over the traditional single-stranded vector.

The combined data shown above demonstrate that the scAAV8-HCV-miRNA-Cluster 5 vector and the ssAAV8-HCV-miR-Cluster 5 vector are effective at inhibiting HCV replication and completely eliminating it from cell culture systems. In addition, it expresses five biologically active anti-HCV miRNAs in mouse liver without inducing hepatotoxicity. Thus, these AAV vectors provide viable clinical candidate for use in the treatment of chronic HCV infection.

DISCUSSION

In this example, four miRNA clusters were generated to express five miRNAs targeting different regions of the HCV genome. Three of the miRNAs target the 5'UTR of HCV, one is specific to the Core region, and one targets the NSSB transcript. The pre-miRNAs were constructed by incorporating validated siRNA and shRNA sequences into the endogenous miR-17-92 cluster. The mature miRNAs were designed to mimic the secondary structure of their endogenous counterparts and to have low internal stability at their 5' ends. These characteristics have been associated with preferential incorporation of the guide strand into the RISC (4;5). The miRNAs are expressed from a liver specific promoter so they can ultimately be evaluated for inhibition of HCV replication in hepatocytes. Using RLuc reporter plasmids, the data indicates that four of the five miRNAs inhibit their cognate sequence by approximately 35-80% in vitro, when expressed individually. Co-expression of the miRNAs from a polycistronic pri-miRNA led to ~60-70% knockdown of cognate targets in vitro, demonstrating that simultaneous expression of the miRNAs does not sacrifice their activity, and in some cases enhances it. The miRNAs that were active in vitro (i.e., miR-UTR1, miR-UTR3, miR-Core, miR-NSSB) showed even higher levels of inhibition in vivo, achieving 65-95% silencing from HCV-miR Cluster 1+Intron and 79-97% inhibition from HCV-miR Cluster 2. In both in vitro and in vivo settings, one of the miRNAs in HCV-miR Cluster 1 (miR-UTR2) was completely inactive. This miRNA was incorporated into the endogenous miR-18 scaffold. When it was instead incorporated into the endogenous miR-17 scaffold (HCV-miR Cluster 2), it became highly active, inhibiting its cognate target by 72% and 97% in vitro and in vivo, respectively. Interestingly, the reciprocal change, that is, moving miR-UTR1 from the miR-17 scaffold to the miR-18 scaffold, resulted in the loss of activity of this miRNA. These data indicate that mature miRNAs are not processed from the miR-18 scaffold. This was confirmed by Northern blot analyses which demonstrated that miR-UTR2 was not produced from HCV-miR Cluster 1, but was expressed at high levels from HCV-miR cluster 2. Conversely, miR-UTR1 was expressed from HCV-miR Cluster 1, but was not produced from HCV-miR Cluster 2. Although the endogenous miR18 is not expressed at lower levels than the other miRNAs in this cluster in all tissues, it appears to be expressed at lower levels in the liver (43). Thus, it might not be possible to manipulate this miRNA scaffold to achieve high level expression of mature miRNAs in the liver, and the use of the last miRNA in the cluster (i.e., miR-92) as an artificial miRNA scaffold may be a better choice. In view of these data, Cluster 5 was constructed wherein the use of the miR-18 loop was avoided and instead miR-92 was employed to expression an HCV inhibitory RNA targeting UTR-1. This construct, when expressed from an AAV2 vector, scAAV2-HCV-miR-Cluster 5, has the ability to inhibit bona fide HCV replication by up to 96% as it demonstrates effective inhibition of all 5 HCV targeted sequences.

The Northern blots demonstrate that slightly more of the miRNAs are expressed from HCV-miR Cluster 1 +Intron as compared to HCV-miR Cluster 1. This is consistent with data suggesting that it is important to include introns in gene therapy vectors so transcripts can be efficiently assembled into spliceosome complexes and be protected from degradation in the nucleus (44). However, at least for miR-UTR1, which was the only miRNA analyzed from both of these two clusters, no difference in silencing activity was observed between the two plasmids. Using the synthetic siRNA controls to estimate the levels of the miRNAs in liver tissue, the amount of the four active miRNAs expressed from HCV-miR Cluster 1+Intron is ~1.0 fmole (or $6 \times 10^8$ miRNAs) in 25 µg total liver RNA (or ~28 mg tissue, based on yields). This is in the same range as Real-Time PCR measurements for several artificial miRNAs that were expressed from the EF1α promoter and delivered to cells by lentiviral vectors (27). Equivalent levels of miRNAs from a cluster are not necessarily expected for miRNAs expressed from a polycistronic transcript, but the data indicate that the four active miRNAs are present in roughly equal amounts. Using the hepatocelluarity number that has been reported for mice of $1.38 \times 10^8$ cells/g liver tissue (45), 155 miRNAs were calculated to be expressed per cell. Since only ~20-40% of the hepatocytes can be expected to be transfected using the HDTV procedure (41), the transduced hepatocytes can be estimated to express ~400-800 miRNAs/cell. It has been reported that the copy number of HCV in hepatocytes is less than 10 copies/cell (46), and thus expression of miRNAs from HCV-miR Cluster 1+Intron would be expected to be sufficient for inhibiting HCV replication.

There have been a number of reports indicating that siRNAs can result in alterations in mRNA expression (47) and in toxicity in vitro (40). In addition, serious toxicity and fatalities have been observed following sustained expression of shRNAs in mouse liver (31) and brain (29;32). However, the use of artificial miRNAs, as opposed to shRNAs, prevented competition between exogenous and endogenous shRNA and miRNAs (30), and eliminated the CNS toxicity seen in mouse brains (29;32). For these reasons the miRNA platform was utilized to design a therapeutic strategy for HCV. The anti-HCV-miRNAs used in the present example resulted in no toxicity in Huh-7 cells, as measured by cell viability, supporting the notion that the miRNAs do not induce off-target effects (40). In addition, the anti-HCV miRNAs are specific for their targets and the guide strands of the miRNA hairpin structures are preferentially loaded into the RISC. A correlation has been found between toxicity and the presence of a four by motif (UGGC) in the siRNA strand entering the RISC (40), and other motifs, such as GUCCUUCAA and UGUGU have been implicated in the induction of an immune response. None of these sequences are present in the anti-HCV miRNAs. Thus, the combined data strongly indicate that the anti-HCV miRNAs are safe.

For therapeutic purposes, it will be necessary to incorporate this cluster into a clinically relevant delivery system that allows for efficient delivery to the liver. Viral vectors are being developed for delivery of many RNAi-mediated therapies. Although individual miRNAs have been evaluated previously in vivo (17;18;29;32), artificial polycistronic pri-miRNAs have been evaluated in in vitro studies only (34;35). Four of the anti-HCV miRNAs expressed from the clusters described hereinabove target conserved regions in all six HCV genotypes and the combination of all five miRNAs has the potential to prevent the emergence of escape mutants (10). The use of a liver-specific promoter ensures expression in hepatocytes, the site of HCV replication, while minimizing off-target effects in non-target tissues. Thus, the ability to express multiple RNAi effectors simultaneously from a single tissue-specific promoter has the potential to provide both enhanced efficacy and safety. Recombinant adeno-associated viral vectors (rAAV) of serotype 8 are particularly effective in transducing mouse liver (50) and this serotype may prevent some of the immune complications associated with the use of rAAV2 vectors (51). Recombinant AAV vectors encoding HCV-miR Cluster 1 or 2 can be used to test the efficacy of the individual miRNAs against a bonafide HCV infection. Other AAV vectors suitable for delivering exogenous nucleic acids to cells are described in U.S. Pat. No.s 7,351,813 (wherein the miRNA cassette described herein can be substituted for the FIX encoding nucleic acid); 7,282,199; 7,261,544; 7,259,151; 7,241,447; 6,936,243 and 6,156,303 In addition to HCV, the miRNA clusters could be generated to inhibit other viruses and cellular gene products associated with disease and will also be useful for basic research applications.

REFERENCES

1. Castanotto, D. and Rossi, J. J. (2009) The promises and pitfalls of RNA-interference-based therapeutics. *Nature*, 457, 426-433.
2. Zamore, P. D. and Haley, B. (2005) Ribo-gnome: the big world of small RNAs. *Science*, 309, 1519-1524.

3. Brummelkamp, T. R., Bernards, R. and Agami, R. (2002) A system for stable expression of short interfering RNAs in mammalian cells. *Science,* 296, 550-553.

4. Schwarz, D. S., Hutvagner, G., Du, T., Xu, Z., Aronin, N. and Zamore, P. D. (2003) Asymmetry in the assembly of the RNAi enzyme complex. *Cell,* 115, 199-208.

5. Khvorova, A., Reynolds, A. and Jayasena, S. D. (2003) Functional siRNAs and miRNAs exhibit strand bias. *Cell,* 115, 209-216.

6. Birmingham, A., Anderson, E., Sullivan, K., Reynolds, A., Boese, Q., Leake, D., Karpilow, J. and Khvorova, A. (2007) A protocol for designing siRNAs with high functionality and specificity. *Nat. Protoc.,* 2, 2068-2078.

7. Watanabe, T., Umehara, T. and Kohara, M. (2007) Therapeutic application of RNA interference for hepatitis C virus. *Adv. Drug Deliv. Rev.,* 59, 1263-1276.

8. Wilson, J. A. and Richardson, C. D. (2006) Future promise of siRNA and other nucleic acid based therapeutics for the treatment of chronic HCV. *Infect. Disord. Drug Targets.,* 6, 43-56.

9. McCaffrey, A. P., Meuse,L., Pham, T. T., Conklin, D. S., Hannon, G. J. and Kay, M. A. (2002) RNA interference in adult mice. *Nature,* 418, 38-9.

10. Leonard, J. N. and Schaffer, D. V. (2005) Computational design of antiviral RNA interference strategies that resist human immunodeficiency virus escape. *J Virol,* 79, 1645-54.

11. Berkhout, B. (2004) RNA interference as an antiviral approach: targeting HIV-1. *Curr. Opin. Mol. Ther.,* 6, 141-145.

12. Wilson, J. A. and Richardson, C. D. (2005) Hepatitis C virus replicons escape RNA interference induced by a short interfering RNA directed against the NS5b coding region. *J Virol,* 79, 7050-8.

13. Henry, S. D., van der Wegen, P., Metselaar, H. J., Tilanus, H. W., Scholte, B. J. and van der Laan, L. J. (2006) Simultaneous targeting of HCV replication and viral binding with a single lentiviral vector containing multiple RNA interference expression cassettes. *Mol Ther.*

14. ter, B. O., 't, H. K., Liu, Y. P., Centlivre, M., von Eije, K. J. and Berkhout, B. (2008) Lentiviral vector design for multiple shRNA expression and durable HIV-1 inhibition. *Mol. Ther.,* 16, 557-564.

15. Zeng, Y., Wagner, E. J. and Cullen, B. R. (2002) Both natural and designed micro RNAs can inhibit the expression of cognate mRNAs when expressed in human cells. *Mol. Cell,* 9, 1327-1333.

16. Du, G., Yonekubo, J., Zeng, Y., Osisami, M. and Frohman, M. A. (2006) Design of expression vectors for RNA interference based on miRNAs and RNA splicing. *FEBS 1,* 273, 5421-5427.

17. Ely, A., Naidoo, T., Mufamadi, S., Crowther, C. and Arbuthnot, P. (2008) Expressed anti-HBV primary microRNA shuttles inhibit viral replication efficiently in vitro and in vivo. *Mol. Ther.,* 16, 1105-1112.

18. Xia, X. G., Zhou, H., Samper, E., Melov, S. and Xu, Z. (2006) Pol II-expressed shRNA knocks down Sod2 gene expression and causes phenotypes of the gene knockout in mice. PLoS. *Genet.,* 2, e10.

19. Boden, D., Pusch, O., Silbermann, R., Lee, F., Tucker, L. and Ramratnam, B. (2004) Enhanced gene silencing of HIV-1 specific siRNA using microRNA designed hairpins. *Nucleic Acids Res,* 32, 1154-8.

20. Keck, K., Volper, E. M., Spengler, R. M., Long, D. D., Chan, C. Y., Ding, Y. and McCaffrey, A. P. (2009) Rational design leads to more potent RNA interference against hepatitis B virus: factors effecting silencing efficiency. *Mol. Ther.,* 17, 538-547.

21. Stegmeier, F., Hu, G., Rickles, R. J., Hannon, G. J. and Elledge, S. J. (2005) A lentiviral microRNA-based system for single-copy polymerase II-regulated RNA interference in mammalian cells. *Proc. Natl. Acad. Sci. U.S.A,* 102, 13212-13217.

22. Snyder, L. L., Esser, J. M., Pachuk, C. J. and Steel, L. F. (2008) Vector design for liver-specific expression of multiple interfering RNAs that target hepatitis B virus transcripts. *Antiviral Res.,* 80, 36-44.

23. Zhou, H., Huang, C. and Xia, X. G. (2008) A tightly regulated Pol III promoter for synthesis of miRNA genes in tandem. Biochim. Biophys. *Acta,* 1779, 773-779.

24. Chung, K. H., Hart, C. C., Al-Bassam, S., Avery, A., Taylor, J., Patel, P. D., Vojtek, A. B. and Turner, D. L. (2006) Polycistronic RNA polymerase II expression vectors for RNA interference based on BIC/miR-155. *Nucleic Acids Res.,* 34, e53.

25. Zhu, X., Santat, L. A., Chang, M. S., Liu, J., Zavzavadjian, J. R., Wall, E. A., Kivork, C., Simon, M. I. and Fraser, I. D. (2007) A versatile approach to multiple gene RNA interference using microRNA-based short hairpin RNAs. *BMC. Mol. Biol.,* 8, 98.

26. Sun, D., Melegari, M., Sridhar, S., Rogler, C. E. and Zhu, L. (2006) Multi-miRNA hairpin method that improves gene knockdown efficiency and provides linked multi-gene knockdown. *Biotechniques,* 41, 59-63.

27. Amendola, M., Passerini, L., Pucci, F., Gentner, B., Bacchetta, R. and Naldini, L. (2009) Regulated and multiple miRNA and siRNA delivery into primary cells by a lentiviral platform. *Mol. Ther.,* 17, 1039-1052.

28. Boudreau, R. L., Monteys, A. M. and Davidson, B. L. (2008) Minimizing variables among hairpin-based RNAi vectors reveals the potency of shRNAs. *RNA.,* 14, 1834-1844.

29. McBride, J. L., Boudreau, R. L., Harper, S. Q., Staber, P. D., Monteys, A. M., Martins, I., Gilmore, B. L., Burstein, H., Peluso, R. W., Polisky, B. et al. (2008) Artificial miRNAs mitigate shRNA-mediated toxicity in the brain: implications for the therapeutic development of RNAi. *Proc. Natl. Acad. Sci. U.S.A,* 105, 5868-5873.

30. Castanotto, D., Sakurai, K., Lingeman, R., Li, H., Shively, L., Aagaard, L., Soifer, H., Gatignol, A., Riggs, A. and Rossi, J. J. (2007) Combinatorial delivery of small interfering RNAs reduces RNAi efficacy by selective incorporation into RISC. *Nucleic Acids Res.,* 35, 5154-5164.

31. Grimm, D., Streetz, K. L., Jopling, C. L., Storm, T. A., Pandey, K., Davis, C. R., Marion, P., Salazar, F. and Kay, M. A. (2006) Fatality in mice due to oversaturation of cellular microRNA/short hairpin RNA pathways. *Nature,* 441, 537-41.

32. Boudreau, R. L., Martins, I. and Davidson, B. L. (2009) Artificial microRNAs as siRNA shuttles: improved safety as compared to shRNAs in vitro and in vivo. *Mol. Ther.,* 17, 169-175.

33. Cai, X., Hagedorn, C. H. and Cullen, B. R. (2004) Human microRNAs are processed from capped, polyadenylated transcripts that can also function as mRNAs. *RNA.,* 10, 1957-1966.

34. Aagaard, L. A., Zhang, J., von Eije, K. J., Li, H., Saetrom, P., Amarzguioui, M. and Rossi, J. J. (2008) Engineering and optimization of the miR-106b cluster for ectopic expression of multiplexed anti-HIV RNAs. *Gene Ther.,* 15, 1536-1549.

35. Liu, Y. P., Haasnoot, J., ter, B. O., Berkhout, B. and Konstantinova, P. (2008) Inhibition of HIV-1 by multiple siRNAs expressed from a single microRNA polycistron. *Nucleic Acids Res.,* 36, 2811-2824.

36. Lagos-Quintana, M., Rauhut, R., Lendeckel, W. and Tuschl, T. (2001) Identification of novel genes coding for small expressed RNAs. *Science,* 294, 853-858.

37. Ding, Y., Chan, C. Y. and Lawrence, C. E. (2004) Sfold web server for statistical folding and rational design of nucleic acids. *Nucleic Acids Res.,* 32, W135-W141.

38. Couto, L. B. (2004) Preclinical gene therapy studies for hemophilia using adeno-associated virus (AAV) vectors. *Semin. Thromb. Hemost.,* 30, 161-171.

39. Birmingham, A., Anderson, E. M., Reynolds, A., Ilsley-Tyree, D., Leake, D., Fedorov, Y., Baskerville, S., Maksimova, E., Robinson, K., Karpilow, J. et al. (2006) 3' UTR seed matches, but not overall identity, are associated with RNAi off-targets. *Nat. Methods,* 3, 199-204.

40. Fedorov, Y., Anderson, E. M., Birmingham, A., Reynolds, A., Karpilow, J., Robinson, K., Leake, D., Marshall, W. S. and Khvorova, A. (2006) Off-target effects by siRNA can induce toxic phenotype. *RNA.,* 12, 1188-1196.

41. Liu, F., Song, Y. and Liu, D. (1999) Hydrodynamics-based transfection in animals by systemic administration of plasmid DNA. *Gene Ther,* 6, 1258-66.

42. Sempere, L. F., Freemantle, S., Pitha-Rowe, I., Moss, E., Dmitrovsky, E. and Ambros, V. (2004) Expression profiling of mammalian microRNAs uncovers a subset of brain-expressed microRNAs with possible roles in murine and human neuronal differentiation. *Genome Biol.,* 5, R13.

43. Boggs, R. M., Moody, J. A., Long, C. R., Tsai, K. L. and Murphy, K. E. (2007) Identification, amplification and characterization of miR-17-92 from canine tissue. *Gene,* 404, 25-30.

44. Miao, C. H., Ohashi, K., Patijn, G. A., Meuse, L., Ye, X., Thompson, A. R. and Kay, M. A. (2000) Inclusion of the hepatic locus control region, an intron, and untranslated region increases and stabilizes hepatic factor IX gene expression in vivo but not in vitro. *Mol Ther,* 1, 522-32.

45. Sohlenius-Stembeck, A. K. (2006) Determination of the hepatocellularity number for human, dog, rabbit, rat and mouse livers from protein concentration measurements. *Toxicol. In Vitro,* 20, 1582-1586.

46. White, P. A., Pan, Y., Freeman, A. J., Marinos, G., Ffrench, R. A., Lloyd, A. R. and Rawlinson, W. D. (2002) Quantification of hepatitis C virus in human liver and serum samples by using LightCycler reverse transcriptase PCR. *J Clin Microbiol,* 40, 4346-8.

47. Jackson, A. L., Bartz, S. R., Schelter, J., Kobayashi, S. V., Burchard, J., Mao, M., Li, B., Cavet, G. and Linsley, P. S. (2003) Expression profiling reveals off-target gene regulation by RNAi. *Nat. Biotechnol.,* 21, 635-637.

48. Matzke, M. A. and Birchler, J. A. (2005) RNAi-mediated pathways in the nucleus. *Nat. Rev. Genet.,* 6, 24-35.

49. Takigawa, Y., Nagano-Fujii, M., Deng, L., Hidajat, R., Tanaka, M., Mizuta, H. and Hotta, H. (2004) Suppression of hepatitis C virus replicon by RNA interference directed against the NS3 and NS5B regions of the viral genome. *Microbiol Immunol,* 48, 591-8.

50. Gao, G. P., Alvira, M. R., Wang, L., Calcedo, R., Johnston, J. and Wilson, J. M. (2002) Novel adeno-associated viruses from rhesus monkeys as vectors for human gene therapy. *Proc Natl Acad Sci USA,* 99, 11854-9.

51. Mingozzi, F., Maus, M. V., Hui, D. J., Sabatino, D. E., Murphy, S. L., Rasko, J. E., Ragni, M. V., Manno, C. S., Sommer, J., Jiang, H. et al. (2007) CD8(+) T-cell responses to adeno-associated virus capsid in humans. *Nat. Med.,* 13, 419-422.

While certain of the preferred embodiments of the present invention have been described and specifically exemplified above, it is not intended that the invention be limited to such embodiments. Various modifications may be made thereto without departing from the scope of the present invention, as set forth in the following claims.

What is claimed is:

1. A composition comprising a miRNA expression cassette comprising a cluster sequence selected from the group of consisting of cluster 1, cluster 2 and cluster 5.

2. The composition of claim 1, wherein said cluster sequence is cluster 5.

3. The composition of claim 1 or claim 2, wherein said cluster sequence is contained in a vector.

4. The composition of claim 3, wherein said vector is selected from the group consisting of AAV vectors, lentiviral vectors, retroviral vectors and AV vectors.

5. The composition of claim 4, wherein said vector is an recombinant AAV vector having a serotype selected from the group consisting of AAV-2, AAV-6 and AAV 8.

6. The composition of claim 3, wherein the expression of nucleotides is under the control of a single promoter.

7. The composition of claim 6, wherein said promoter is a tissue-specific promoter.

8. The composition of claim 7, wherein said promoter is a liver-specific alpha-one antitrypsin promoter, said composition additionally comprising a liver-specific enhancer and a polyadenylation signal.

9. The composition of claim 8, wherein said enhancer is the apolipoprotein E hepatic control region.

10. The composition of claim 8, wherein said polyadenylation signal is the bovine growth hormone polyadenylation signal.

11. The composition of claim 3, wherein said composition comprises an intron.

12. The composition of claim 11, wherein said intron is downstream of said promoter and upstream of said cluster.

13. The composition of claim 12, wherein said intron is derived from human growth hormone.

14. A method of reducing HCV viral load in a patient comprising administering to the liver of said patient a therapeutically effective amount of the composition of claim 3 which directs cleavage of target HCV mRNA sequences present in said patient, thereby reducing HCV viral load.

15. The method of claim 14, wherein said composition is introduced directly into said patient.

16. The method of claim 15, wherein said introduction is via intravenous infusion.

17. The method of claim 14, wherein said method results in inhibition of HCV replication in said patient.

18. The method of claim 12, wherein introducing the vector to a cell, tissue, or organ of interest comprises: ligating the miRNA cassette into a viral delivery vector to form a viral miRNA expression construct; packaging the viral miRNA expression construct into viral particles; and delivering the viral particles to the cell, tissue, or organ of interest.

19. The method of claim 18, wherein the miRNA cassette comprising nucleic acids which target multiple regions of a HCV genome.

20. The method of claim 19, wherein said vector is an AAV vector and the miRNA cassette is cluster 5.

* * * * *

SEQUENCE LISTING

```
<160> NUMBER OF SEQ ID NOS: 33

<210> SEQ ID NO 1
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 1
ccauaguggu cugcggaac                                                    19

<210> SEQ ID NO 2
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 2
aaaggccuug ugguacugcc u                                                 21

<210> SEQ ID NO 3
<211> LENGTH: 19
<212> TYPE: RNA
<213> ORGANISM: Artificial Sequence
<220> FEATURE:
<223> OTHER INFORMATION: Synthetic Sequence
```

```
<400> SEQUENCE: 3
aggucucgua gaccgugca                                              19

<210> SEQ ID NO 4
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 4
aaccucaaag aaaaaccaaa c                                           21

<210> SEQ ID NO 5
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 5
gacacugaga caccaauuga c                                           21

<210> SEQ ID NO 6
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 6
guuccgcaga ccacuaugg                                              19

<210> SEQ ID NO 7
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 7
aggcaguacc acaaggccuu u                                           21

<210> SEQ ID NO 8
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 8
ugcacggucu acgagaccu                                              19

<210> SEQ ID NO 9
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 9
guuugguuuu ucuuugaggu u                                           21

<210> SEQ ID NO 10
```

```
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 10
gucaauuggu gucucagugu c                                              21

<210> SEQ ID NO 11
<211> LENGTH: 34
<212> TYPE: DNA
<213> ORGANISM: Artificial Sequence
<220> FEATURE:
<223> OTHER INFORMATION: Primer

<400> SEQUENCE: 11
tagcgaattc gctgtttgtg tgctgcctct gaag                                34

<210> SEQ ID NO 12
<211> LENGTH: 34
<212> TYPE: DNA
<213> ORGANISM: Artificial Sequence
<220> FEATURE:
<223> OTHER INFORMATION: Primer

<400> SEQUENCE: 12
tagcgcatgc actgtcccag gtcagtggtg gtgc                                34

<210> SEQ ID NO 13
<211> LENGTH: 36
<212> TYPE: DNA
<213> ORGANISM: Artificial Sequence
<220> FEATURE:
<223> OTHER INFORMATION: Primer

<400> SEQUENCE: 13
tagcgtttaa acctgtgcct tctagttgcc agccat                              36

<210> SEQ ID NO 14
<211> LENGTH: 34
<212> TYPE: DNA
<213> ORGANISM: Artificial Sequence
<220> FEATURE:
<223> OTHER INFORMATION: Primer

<400> SEQUENCE: 14
tagcaagctt atagagccca ccgcatcccc agca                                34

<210> SEQ ID NO 15
<211> LENGTH: 28
<212> TYPE: DNA
<213> ORGANISM: Artificial Sequence
<220> FEATURE:
<223> OTHER INFORMATION: Primer

<400> SEQUENCE: 15
tagcgcatgc ttcgaacagg taagcgcc                                       28

<210> SEQ ID NO 16
<211> LENGTH: 28
<212> TYPE: DNA
<213> ORGANISM: Artificial Sequence
<220> FEATURE:
<223> OTHER INFORMATION: Primer

<400> SEQUENCE: 16
```
tagcgcatgc aacctgggga gaaaccag                                    28

<210> SEQ ID NO 17
<211> LENGTH: 19
<212> TYPE: DNA
<213> ORGANISM: Artificial Sequence
<220> FEATURE:
<223> OTHER INFORMATION: Probe

<400> SEQUENCE: 17
ccatagtggt ctgcggaac                                              19

<210> SEQ ID NO 18
<211> LENGTH: 21
<212> TYPE: DNA
<213> ORGANISM: Artificial Sequence
<220> FEATURE:
<223> OTHER INFORMATION: Probe

<400> SEQUENCE: 18
aaaggccttg tggtactgcc t                                           21

<210> SEQ ID NO 19
<211> LENGTH: 19
<212> TYPE: DNA
<213> ORGANISM: Artificial Sequence
<220> FEATURE:
<223> OTHER INFORMATION: Probe

<400> SEQUENCE: 19
aggtctcgta gaccgtgca                                              19

<210> SEQ ID NO 20
<211> LENGTH: 21
<212> TYPE: DNA
<213> ORGANISM: Artificial Sequence
<220> FEATURE:
<223> OTHER INFORMATION: Probe

<400> SEQUENCE: 20
aacctcaaag aaaaaccaaa c                                           21

<210> SEQ ID NO 21
<211> LENGTH: 21
<212> TYPE: DNA
<213> ORGANISM: Artificial Sequence
<220> FEATURE:
<223> OTHER INFORMATION: Probe

<400> SEQUENCE: 21
gacactgaga caccaattga c                                           21

<210> SEQ ID NO 22
<211> LENGTH: 23
<212> TYPE: DNA
<213> ORGANISM: Artificial Sequence
<220> FEATURE:
<223> OTHER INFORMATION: Probe

<400> SEQUENCE: 22
tatggaacgc ttcacgaatt tgc                                         23

<210> SEQ ID NO 23
<211> LENGTH: 19
<212> TYPE: RNA

```
<213> ORGANISM: Artificial Sequence
<220> FEATURE:
<223> OTHER INFORMATION: Synthetic Sequence

<400> SEQUENCE: 23
guuccgcaga ccacuaugg                                                    19

<210> SEQ ID NO 24
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 24
aggcaguacc acaaggccuu u                                                 21

<210> SEQ ID NO 25
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 25
ugcacggucu acgagaccu                                                    19

<210> SEQ ID NO 26
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 26
guuugguuuu ucuuugaggu u                                                 21

<210> SEQ ID NO 27
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 27
gucaauuggu gucucagugu c                                                 21

<210> SEQ ID NO 28
<211> LENGTH: 36
<212> TYPE: DNA
<213> ORGANISM: Artificial Sequence
<220> FEATURE:
<223> OTHER INFORMATION: Primer

<400> SEQUENCE: 28
tagcgcgatc gcgctgtttg tgtgctgcct ctgaag                                 36

<210> SEQ ID NO 29
<211> LENGTH: 34
<212> TYPE: DNA
<213> ORGANISM: Artificial Sequence
<220> FEATURE:
<223> OTHER INFORMATION: Primer

<400> SEQUENCE: 29
tagcgcatgc actgtcccag gtcagtggtg gtgc                                   34
```

<210> SEQ ID NO 30
<211> LENGTH: 1669
<212> TYPE: DNA
<213> ORGANISM: Artificial Sequence
<220> FEATURE:
<223> OTHER INFORMATION: Cluster 1

<400> SEQUENCE: 30

| | | | | | |
|---|---|---|---|---|---|
| gctgtttgtg | tgctgcctct | gaagtccaca | ctgaacaaac | ttcagcctac | tcatgtccct | 60 |
| aaaatgggca | acattgcaa | gcagcaaaca | gcaaacacac | agccctccct | gcctgctgac | 120 |
| cttggagctg | gggcagaggt | cagagacctc | tctgggccca | tgccacctcc | aacatccact | 180 |
| cgaccccttg | gaatttcggt | ggagaggagc | agaggttgtc | ctggcgtggt | ttaggtagtg | 240 |
| tgagaggggt | acccggggat | cttgctacca | gtggaacagc | cactaaggat | tctgcagtga | 300 |
| gagcagaggg | ccagctaagt | ggtactctcc | cagagactgt | ctgactcacg | ccaccccctc | 360 |
| caccttggac | acaggacgct | gtggtttctg | agccaggtac | aatgactcct | ttcggtaagt | 420 |
| gcagtggaag | ctgtacactg | cccaggcaaa | gcgtccgggc | agcgtaggcg | ggcgactcag | 480 |
| atcccagcca | gtggacttag | cccctgtttg | ctcctccgat | aactggggtg | accttggtta | 540 |
| atattcacca | gcagcctccc | ccgttgcccc | tctggatcca | ctgcttaaat | acggacgagg | 600 |
| acagggccct | gtctcctcag | cttcaggcac | caccactgac | ctgggacagt | gcatgcgtta | 660 |
| gagtttgagg | tgttaattct | aattatctat | ttcaaattta | gcaggaaaaa | agagaacatc | 720 |
| accggttaaa | actgaagatt | gtgaccagtc | agaataatgt | gttccgcaga | ccactatggg | 780 |
| tagtgatatg | tgcatctacc | atactgcttt | gcggattggc | attatggtga | cagctgcctc | 840 |
| gggaagccaa | gttggatcct | aaagtgcagg | gcctgctgat | gttgagtgct | ttttgttcag | 900 |
| gcagtaccac | aaggccttta | gtgaagtaga | ttagcatcta | aggcgttgca | gtagtgtcct | 960 |
| ggcataagaa | gttatgtatt | catccaataa | tcgatgccaa | gcaagtatat | aggtgtttta | 1020 |
| atagtttttg | tttgcagtcc | tctgttagag | gtctcgtacc | gtgttacaag | aagaatgtag | 1080 |
| ttgcacggtc | tacgagacct | ctgatggtgg | cctgctattt | ccttcaaatg | aatgattttt | 1140 |
| actaattttg | tgtactttta | ttgatcagat | gtagaatctg | cctggtctat | ctgatgtgac | 1200 |
| agcttctgta | gcacgtttgg | ttttctttg | aggttagtgt | ttagttatct | acctcagaga | 1260 |
| gaaactaatt | cgtactgcta | gctgtagaac | tccagcttcg | gccggtcgcc | caatcaaact | 1320 |
| gtcctgttac | tgaacactgt | tctatggttg | acactgagca | caattgtcat | gctgtgtgat | 1380 |
| attctgcgtc | aattggtgtc | tcagtgtcga | ctgtggtagt | gaaaagtctg | tagaaaagtg | 1440 |
| tttaaactgt | gccttctagt | tgccagccat | ctgttgtttg | ccctccccc | gtgccttcct | 1500 |
| tgaccctgga | aggtgccact | cccactgtcc | tttcctaata | aaatgaggaa | attgcatcgc | 1560 |
| attgtctgag | taggtgtcat | tctattctgg | ggggtggggt | ggggcaggac | agcaagggg | 1620 |
| aggattggga | agacaatagc | aggcatgctg | gggatgcggt | gggctctat | | 1669 |

<210> SEQ ID NO 31
<211> LENGTH: 1670
<212> TYPE: DNA
<213> ORGANISM: Artificial Sequence
<220> FEATURE:
<223> OTHER INFORMATION: Cluster 2

<400> SEQUENCE: 31
gctgtttgtg tgctgcctct gaagtccaca ctgaacaaac ttcagcctac tcatgtccct    60

-continued

```
aaaatgggca acattgcaa gcagcaaaca gcaaacacac agccctccct gcctgctgac      120
cttggagctg ggcagaggt cagagacctc tctgggccca tgccacctcc aacatccact      180
cgaccccttg gaatttcggt ggagaggagc agaggttgtc ctggcgtggt ttaggtagtg      240 tgagagggt acccggggat cttgctacca gtggaacagc cactaaggat tctgcagtga      300
gagcagaggg ccagctaagt ggtactctcc cagagactgt ctgactcacg ccacccctc      360 caccttggac acaggacgct gtggtttctg agccaggtac aatgactcct ttcggtaagt      420
gcagtggaag ctgtacactg cccaggcaaa gcgtccgggc agcgtaggcg ggcgactcag      480
atcccagcca gtggacttag cccctgtttg ctcctccgat aactgggtg accttggtta      540 atattcacca gcagcctccc ccgttgcccc tctggatcca ctgcttaaat acggacgagg      600
acagggccct gtctcctcag cttcaggcac caccactgac ctgggacagt gcatgcgtta      660
gagtttgagg tgttaattct aattatctat ttcaaattta gcaggaaaaa agagaacatc      720
accggttaaa actgaagatt gtgaccagtc agaataatgt aggcagtacc acaaggcctt      780
tagtgatatg tgcatctaag gccatgagat actgcgaagc attatggtga cagctgcctc      840
gggaagccaa gttggatcct aaagtgcagg gcctgctgat gttgagtgct ttttgttcgt      900
tccgcagacc actatggata gtgaagtaga ttagcatcta ccatcgtgag ctggggaagt      960
ggcataagaa gttatgtatt catccaataa tcgatgccaa gcaagtatat aggtgtttta    1020 atagttttg tttgcagtcc tctgttagag gtctcgtacc gtgttacaag aagaatgtag    1080
ttgcacggtc tacgagacct ctgatggtgg cctgctattt ccttcaaatg aatgattttt    1140
actaattttg tgtactttta ttgatcagat gtagaatctg cctggtctat ctgatgtgac    1200
agcttctgta gcacgtttgg ttttctttg aggttagtgt ttagttatct acctcagaga    1260
gaaactaatt cgtactgcta gctgtagaac tccagcttcg gccggtcgcc caatcaaact    1320
gtcctgttac tgaacactgt tctatggttg acactgagca caattgtcat gctgtgtgat    1380
attctgcgtc aattggtgtc tcagtgtcga ctgtggtagt gaaagtctg tagaaaagtg    1440 tttaaacctg tgccttctag ttgccagcca tctgttgttt gccctcccc cgtgccttcc    1500 ttgaccctgg aagtgccac tcccactgtc ctttcctaat aaaatgagga aattgcatcg    1560
cattgtctga gtaggtgtca ttctattctg ggggtggg tgggcagga cagcaagggg    1620 gaggattggg aagacaatag caggcatgct ggggatgcgg tgggctctat              1670
```

<210> SEQ ID NO 32
<211> LENGTH: 9024
<212> TYPE: DNA
<213> ORGANISM: Artificial Sequence
<220> FEATURE:
<223> OTHER INFORMATION: Synthetic Sequence

<400> SEQUENCE: 32

```
cctgcaggga gatctgccac tccctctctg cgcgctcgct cgctcactga ggccgggcga       60
ccaaaggtcg cccgacgccc gggctttgcc cgggcggcct cagtgagcga gcgagcgcgc      120
agagagggag tggccaactc catcactagg ggttcctgcg atcgcgctgt tgtgtgctg      180 cctctgaagt ccacactgaa caaacttcag cctactcatg tccctaaaat gggcaaacat      240
tgcaagcagc aaacagcaaa cacacagccc tccctgcctg ctgaccttgg agctggggca      300
gaggtcagag acctctctgg gcccatgcca cctccaacat ccactcgacc ccttggaatt      360
tcggtggaga ggagcagagg ttgtcctggc gtggtttagg tagtgtgaga ggggtacccg      420 ggatcttgc taccagtgga acagccacta aggattctgc agtgagagca gagggccagc      480
```

```
taagtggtac tctcccagag actgtctgac tcacgccacc ccctccacct tggacacagg        540
acgctgtggt ttctgagcca ggtacaatga ctcctttcgg taagtgcagt ggaagctgta        600
cactgcccag gcaaagcgtc cgggcagcgt aggcgggcga ctcagatccc agccagtgga        660
cttagcccct gtttgctcct ccgataactg gggtgacctt ggttaatatt caccagcagc        720
ctcccccgtt gcccctctgg atccactgct taaatacgga cgaggacagg gccctgtctc        780
ctcagcttca ggcaccacca ctgacctggg acagtgcatg cgttagagtt tgaggtgtta        840
attctaatta tctatttcaa atttagcagg aaaaagaga acatcaccgg ttaaaactga         900
agattgtgac cagtcagaat aatgtaggca gtaccacaag gcctttagtg atatgtgcat        960
ctaaggccat gagatactgc gaagcattat ggtgacagct gcctcgggaa gccaagttgg       1020
atcctaaagt gcagggcctg ctgatgttga gtgcttttta agaagttatg tattcatcca       1080
ataatcgatg ccaagcaagt atataggtgt tttaatagtt tttgtttgca gtcctctgtt       1140
agaggtctcg taccgtgtta caagaagaat gtagttgcac ggtctacgag acctctgatg       1200
gtggcctgct atttccttca aatgaatgat ttttactaat tttgtgtact tttattgatc       1260
agatgtagaa tctgcctggt ctatctgatg tgacagcttc tgtagcacgt ttggtttttc       1320
tttgaggtta gtgtttagtt atctacctca gagagaaact aattcgtact gctagctgta       1380
gaactccagc ttcggccggt cgcccaatca aactgtcctg ttactgaaca ctgttctatg       1440
gttgacactg agcacaattg tcatgctgtg tgatattctg cgtcaattgg tgtctcagtg       1500
tcgactgtgg tagtgaaaag tctgtagaaa agtgtttaaa caagggaaac tcaaaccccct      1560
ttctacacac catagtgact tgtcggaatc tgtgtttctg tatgggttcc gcagaccact       1620
atggtgttga gttggtggg gattgtgacc agaagatttt gaaaattaaa tattactgaa        1680
gatttcgttt aaactgtgcc ttctagttgc cagccatctg ttgtttgccc ctccccgtg        1740
ccttccttga ccctggaagg tgccactccc actgtccttt cctaataaaa tgaggaaatt       1800
gcatcgcatt gtctgagtag gtgtcattct attctggggg gtggggtggg gcaggacagc       1860
aaggggagg attgggaaga caatagcagg catgctgggg atgcggtggg ctctatgggg        1920
ccggccccac tccctctatg cgcgctcgct cactcactcg gccctgccgg ccagaggccg       1980
gcagtctgga gacctttggt ctccagggcc gagtgagtga gcgagcgcgc atagagggag       2040
tggcatatgt cctgcagggg cagcttgaag gaaatactaa ggcaaaggta ctgcaagtgc       2100
tcgcaacatt cgcttatgcg gattattgcc gtagtgccgc gacgccgggg gcaagatgca       2160
gagattgcca tggtacaggc cgtgcggttg atattgccaa aacagagctg tgggggagag       2220
ttgtcgagaa agagtgcgga agatgcaaag gcgtcggcta ttcaaggatg ccagcaagcg       2280
cagcatatcg cgctgtgacg atgctaatcc caaaccttac ccaacccacc tggtcacgca       2340
ctgttaagcc gctgtatgac gctctggtgg tgcaatgcca caaagaagag tcaatcgcag       2400
acaacatttt gaatgcggtc acacgttagc agcatgattg ccacgatgg caacatatta        2460
acggcatgat attgacttat tgaataaaat tgggtaaatt tgactcaacg atgggttaat       2520
tcgctcgttg tggtagtgag atgaaaagag gcggcgctta ctaccgattc cgcctagttg       2580
gtcacttcga cgtatcgtct ggaactccaa ccatcgcagg cagagaggtc tgcaaaatgc       2640
aatcccgaaa cagttcgcag gtaatagtta gagcctgcat aacggtttcg ggattttta       2700
tatctgcaca acaggtaaga gcattgagtc gataatcgtg aagagtcggc gagcctggtt      2760
agccagtgct ctttccgttg tgctgaatta agcgaatacc ggaagcagaa ccggatcacc      2820
```

```
aaatgcgtac aggcgtcatc gccgcccagc aacagcacaa cccaaactga gccgtagcca    2880
ctgtctgtcc tgaattcatt agtaatagtt acgctgcggc ttttacaca tgaccttcgt    2940 gaaagcgggt ggcaggaggt cgcgctaaca acctcctgcc gttttgcccg tgcatatcgg    3000
tcacgaacaa atctgattac taaacacagt agcctggatt tgttctatca gtaatcgacc    3060
ttattcctaa ttaaatagag caaatcccct tattgggggt aagacatgaa gatgccagaa    3120
aaacatgacc tgttggccgc cattctcgcg gcaaaggaac aaggcatcgg ggcaatcctt    3180
gcgtttgcaa tggcgtacct tcgcggcaga tataatggcg gtgcgtttac aaaaacagta    3240
atcgacgcaa cgatgtgcgc cattatcgcc tggttcattc gtgaccttct cgacttcgcc    3300
ggactaagta gcaatctcgc ttatataacg agcgtgttta tcggctacat cggtactgac    3360
tcgattggtt cgcttatcaa acgcttcgct gctaaaaaag ccggagtaga agatggtaga    3420
aatcaataat caacgtaagg cgttcctcga tatgctggcg tggtcggagg gaactgataa    3480
cggacgtcag aaaaccagaa atcatggtta tgacgtcatt gtaggcggag agctatttac    3540
tgattactcc gatcaccctc gcaaacttgt cacgctaaac ccaaaactca aatcaacagg    3600
cgccggacgc taccagcttc tttcccgttg gtgggatgcc taccgcaagc agcttggcct    3660
gaaagacttc tctccgaaaa gtcaggacgc tgtggcattg cagcagatta aggagcgtgg    3720
cgctttacct atgattgatc gtggtgatat ccgtcaggca atcgaccgtt gcagcaatat    3780
ctgggcttca ctgccgggcg ctggttatgg tcagttcgag cataaggctg acagcctgat    3840
tgcaaaattc aaagaagcgg cggaacggt cagagagatt gatgtatgag cagagtcacc    3900
gcgattatct ccgctctggt tatctgcatc atcgtctgcc tgtcatgggc tgttaatcat    3960
taccgtgata acgccattac ctacaaagcc cagcgcgaca aaaatgccag agaactgaag    4020
ctggcgaacg cggcaattac tgacatgcag atgcgtcagc gtgatgttgc tgcgctcgat    4080
gcaaaataca cgaaggagtt agctgatgct aaagctgaaa atgatgctct cgtgatgat    4140 gttgccgctg tcgtcgtcg gttgcacatc aaagcagtct gtcagtcagt gcgtgaagcc    4200
accaccgcct ccggcgtgga taatgcagcc tcccccgac tggcagacac cgctgaacgg    4260
gattatttca ccctcagaga gaggctgatc actatgcaaa aacaactgga aggaacccag    4320
aagtatatta tgagcagtg cagatagagt tgcccatatc gatgggcaac tcatgcaatt    4380
attgtgagca atacacacgc gcttccagcg gagtataaat gcctaaagta ataaaaccga    4440
gcaatccatt tacgaatgtt tgctgggttt ctgttttaac aacattttct gcgccgccac    4500
aaattttggc tgcatcgaca gttttcttct gcccaattcc agaaacgaag aaatgatggg    4560 tgatggttc ctttggtgct actgctgccg gtttgttttg aacagtaaac gtctgttgag    4620
cacatcctgt aataagcagg gccagcgcag tagcgagtag cattttttc atggtgttat    4680 tcccgatgct ttttgaagtt cgcagaatcg tatgtgtaga aaattaaaca aaccctaaac    4740
aatgagttga aatttcatat tgttaatatt tattaatgta tgtcaggtgc gatgaatcgt    4800
cattgtattc ccggattaac tatgtccaca gccctgacgg ggaacttctc tgcgggagtg    4860
tccgggaata attaaaacga tgcacacagg gtttagcgcg tacacgtatt gcattatgcc    4920
aacgccccgg tgctgacacg gaagaaaccg gacgttatga tttagcgtgg aaagatttgt    4980
gtagtgttct gaatgctctc agtaaatagt aatgaattat caaaggtata gtaatatctt    5040
ttatgttcat ggatatttgt aacccatcgg aaaactcctg ctttagcaag attttccctg    5100
tattgctgaa atgtgatttc tcttgatttc aacctatcat aggacgtttc tataagatgc    5160
gtgtttcttg agaatttaac atttacaacc tttttaagtc cttttattaa cacggtgtta    5220
```

```
tcgttttcta acacgatgtg aatattatct gtggctagat agtaaatata atgtgagacg   5280
ttgtgacgtt ttagttcaga ataaaacaat tcacagtcta aatcttttcg cacttgatcg   5340
aatatttctt taaaaatggc aacctgagcc attggtaaaa ccttccatgt gatacgaggg   5400
cgcgtagttt gcattatcgt ttttatcgtt tcaatctggt ctgacctcct tgtgttttgt   5460
tgatgattta tgtcaaatat taggaatgtt ttcacttaat agtattggtt gcgtaacaaa   5520
gtgcggtcct gctggcattc tggagggaaa tacaaccgac agatgtatgt aaggccaacg   5580
tgctcaaatc ttcatacaga aagatttgaa gtaatatttt aaccgctaga tgaagagcaa   5640
gcgcatggag cgacaaaatg aataaagaac aatctgctga tgatccctcc gtggatctga   5700
ttcgtgtaaa aaatatgctt aatagcacca tttctatgag ttaccctgat gttgtaattg   5760
catgtataga acataaggtg tctctggaag cattcagagc aattgaggca gcgttggtga   5820
agcacgataa taatatgaag gattattccc tggtggttga ctgatcacca taactgctaa   5880
tcattcaaac tatttagtct gtgacagagc caacacgcag tctgtcactg tcaggaaagt   5940
ggtaaaactg caactcaatt actgcaatgc cctcgtaatt aagtgaattt acaatatcgt   6000
cctgttcgga gggaagaacg cgggatgttc attcttcatc acttttaatt gatgtatatg   6060
ctctcttttc tgacgttagt ctccgacggc aggcttcaat gacccaggct gagaaattcc   6120
cggacccttt ttgctcaaga gcgatgttaa tttgttcaat catttggtta ggaaagcgga   6180
tgttgcgggt tgttgttctg cgggttctgt tcttcgttga catgaggttg ccccgtattc   6240
agtgtcgctg atttgtattg tctgaagttg ttttacgtt aagttgatgc agatcaatta   6300
atacgatacc tgcgtcataa ttgattattt gacgtggttt gatggcctcc acgcacgttg   6360
tgatatgtag atgataatca ttatcacttt acgggtcctt tccggtgatc cgacaggtta   6420
cggcctgatg cggtattttc tccttacgca tctgtgcggt atttcacacc gcatacgtca   6480
aagcaaccat agtacgcgcc ctgtagcggc gcattaagcg cggcgggtgt ggtggttacg   6540
cgcagcgtga ccgctacact tgccagcgcc ctagcgcccg ctcctttcgc tttcttccct   6600
tcctttctcg ccacgttcgc cggctttccc cgtcaagctc taaatcgggg gctccctttta   6660 gggttccgat ttagtgcttt acggcacctc gaccccaaaa aacttgattt gggtgatggt   6720
tcacgtagtg ggccatcgcc ctgatagacg gttttttcgcc ctttgacgtt ggagtccacg   6780
ttctttaata gtggactctt gttccaaact ggaacaacac tcaacccatt ctcgggctat   6840
tcttttgatt tataagggat tttgccgatt tcggcctatt ggttaaaaaa tgagctgatt   6900
taacaaaaat ttaacgcgaa ttttaacaaa atattaacgt ttacaatttt atggtgcact   6960
ctcagtacaa tctgctctga tgccgcatag ttaagccagc cccgacaccc gccaacaccc   7020
gctgacgcgc cctgacgggc ttgtctgctc ccggcatccg cttacagaca agctgtgacc   7080
gtctccggga gctgcatgtg tcagaggttt tcaccgtcat caccgaaacg cgcgagacga   7140
aagggcctcg tgatacgcct atttttatag gttaatgtca tgataataat ggtttcttag   7200
acgtcaggtg gcacttttcg gggaaatgtg cgcggaaccc ctatttgttt attttttctaa   7260 atacattcaa atatgtatcc gctcatgaga caataaccct gataaatgct tcaataatat   7320
tgaaaaagga agagtatgag tattcaacat ttccgtgtcg cccttattcc cttttttgcg   7380
gcattttgcc ttcctgtttt tgctcaccca gaaacgctgg tgaaagtaaa agatgctgaa   7440
gatcagttgg gtgcacgagt gggttacatc gaactggatc tcaacagcgg taagatcctt   7500
gagagttttc gccccgaaga acgttttcca atgatgagca cttttaaagt tctgctatgt   7560
```

```
ggcgcggtat tatcccgtat tgacgccggg caagagcaac tcggtcgccg catacactat    7620
tctcagaatg acttggttga gtactcacca gtcacagaaa agcatcttac ggatggcatg    7680
acagtaagag aattatgcag tgctgccata accatgagtg ataacactgc ggccaactta    7740
cttctgacaa cgatcggagg accgaaggag ctaaccgctt ttttgcacaa catgggggat    7800
catgtaactc gccttgatcg ttgggaaccg gagctgaatg aagccatacc aaacgacgag    7860
cgtgacacca cgatgcctgt agcaatggca acaacgttgc gcaaactatt aactggcgaa    7920
ctacttactc tagcttcccg gcaacaatta atagactgga tggaggcgga taaagttgca    7980
ggaccacttc tgcgctcggc ccttccggct ggctggttta ttgctgataa atctggagcc    8040
ggtgagcgtg gtctcgcgg tatcattgca gcactggggc cagatggtaa gccctcccgt     8100
atcgtagtta tctacacgac ggggagtcag gcaactatgg atgaacgaaa tagacagatc    8160
gctgagatag gtgcctcact gattaagcat tggtaactgt cagaccaagt ttactcatat    8220
atactttaga ttgatttaaa acttcatttt taatttaaaa ggatctaggt gaagatcctt    8280
tttgataatc tcatgaccaa aatcccttaa cgtgagtttt cgttccactg agcgtcagac    8340
cccgtagaaa agatcaaagg atcttcttga gatccttttt ttctgcgcgt aatctgctgc    8400
ttgcaaacaa aaaaaccacc gctaccagcg gtggtttgtt tgccggatca agagctacca    8460 actcttttc cgaaggtaac tggcttcagc agagcgcaga taccaaatac tgtccttcta    8520
gtgtagccgt agttaggcca ccacttcaag aactctgtag caccgcctac atacctcgct    8580
ctgctaatcc tgttaccagt ggctgctgcc agtggcgata agtcgtgtct taccgggttg    8640
gactcaagac gatagttacc ggataaggcg cagcggtcgg gctgaacggg gggttcgtgc    8700
acacagccca gcttggagcg aacgacctac accgaactga gatacctaca gcgtgagcta    8760
tgagaaagcg ccacgcttcc cgaagggaga aaggcggaca ggtatccggt aagcggcagg    8820
gtcggaacag gagagcgcac gagggagctt ccagggggaa acgcctggta tctttatagt    8880
cctgtcgggt ttcgccacct ctgacttgag cgtcgatttt tgtgatgctc gtcaggggg     8940 cggagcctat ggaaaaacgc cagcaacgcg gcctttttac ggttcctggc cttttgctgg    9000
ccttttgctc acatgtcctg cagg                                           9024
```

<210> SEQ ID NO 33
<211> LENGTH: 795
<212> TYPE: DNA
<213> ORGANISM: Artificial Sequence
<220> FEATURE:
<223> OTHER INFORMATION: Cluster 5

<400> SEQUENCE: 33

```
taaaactgaa gattgtgacc agtcagaata atgtaggcag taccacaagg cctttagtga     60
tatgtgcatc taaggccatg agatactgcg aagcattatg gtgacagctg cctcgggaag    120
ccaagttgga tcctaaagtg cagggcctgc tgatgttgag tgcttttaa gaagttatgt     180 attcatccaa taatcgatgc caagcaagta tataggtgtt ttaatagttt ttgtttgcag    240
tcctctgtta gaggtctcgt accgtgttac aagaagaatg tagttgcacg gtctacgaga    300
cctctgatgg tggcctgcta tttccttcaa atgaatgatt tttactaatt ttgtgtactt    360
ttattgatca gatgtagaat ctgcctggtc tatctgatgt acagcttct gtagcacgtt     420 tggttttct ttgaggttag tgtttagtta tctacctcag agagaaacta attcgtactg     480
ctagctgtag aactccagct tcggccggtc gcccaatcaa actgtcctgt tactgaacac    540
tgttctatgg ttgacactga gcacaattgt catgctgtgt gatattctgc gtcaattggt    600
```

```
gtctcagtgt cgactgtggt agtgaaaagt ctgtagaaaa gtgtttaaac aagggaaact      660
caaacccctt tctacacacc atagtgactt gtcggaatct gtgtttctgt atgggttccg      720
cagaccacta tggtgttgag tttggtgggg attgtgacca gaagattttg aaaattaaat     780
attactgaag atttc                                                      795
```